US007851433B2

(12) United States Patent
Reifsnyder et al.

(10) Patent No.: US 7,851,433 B2
(45) Date of Patent: Dec. 14, 2010

(54) METHOD OF PURIFYING TFPI AND TFPI ANALOGS

(75) Inventors: David H. Reifsnyder, El Cerrito, CA (US); Duane Inlow, Alamo, CA (US); Glenn Dorin, San Rafael, CA (US); Patricio T. Riquelme, Walnut Creek, CA (US); Cynthia A. Cowgill, Berkeley, CA (US); Douglas G. Bolesch, Berkeley, CA (US); Mark E. Gustafson, St. Charles, MO (US)

(73) Assignees: Novartis Vaccines and Diagnostics, Inc., Emeryville, CA (US); Pharmacia & Upjohn Company, Kalamazoo, MI (US)

( * ) Notice: Subject to any disclaimer, the term of this patent is extended or adjusted under 35 U.S.C. 154(b) by 23 days.

(21) Appl. No.: 10/753,078

(22) Filed: Jan. 8, 2004

(65) Prior Publication Data

US 2005/0037475 A1 Feb. 17, 2005

Related U.S. Application Data

(60) Provisional application No. 60/512,199, filed on Oct. 20, 2003, provisional application No. 60/509,277, filed on Oct. 8, 2003, provisional application No. 60/494,546, filed on Aug. 13, 2003.

(51) Int. Cl.
 *C07K 14/00* (2006.01)
(52) U.S. Cl. ........................................... 514/2; 530/350
(58) Field of Classification Search ....................... None
 See application file for complete search history.

(56) References Cited

U.S. PATENT DOCUMENTS

| | | | |
|---|---|---|---|
| 4,637,834 A | 1/1987 | Thurow | |
| 4,966,852 A | 10/1990 | Wun et al. | |
| 5,051,497 A | 9/1991 | Fanning et al. | |
| 5,212,091 A | 5/1993 | Diaz-Collier et al. | |
| 5,276,015 A | 1/1994 | Khouri et al. | |
| 5,358,708 A | 10/1994 | Patel | |
| 5,466,783 A | 11/1995 | Wun et al. | |
| 5,503,827 A | 4/1996 | Woog et al. | |
| 5,563,123 A | 10/1996 | Innis et al. | |
| 5,589,359 A | 12/1996 | Innis et al. | |
| 5,824,644 A | 10/1998 | Abendschein | |
| 5,885,781 A | 3/1999 | Johnson et al. | |
| 5,902,582 A | 5/1999 | Hung | |
| 6,063,764 A | 5/2000 | Creasey et al. | |
| 6,103,500 A | 8/2000 | Innis et al. | |
| 6,242,414 B1 | 6/2001 | Johnson | |
| 6,319,896 B1 | 11/2001 | Arve et al. | |
| 6,323,326 B1 | 11/2001 | Arve et al. | |
| 6,525,102 B1 * | 2/2003 | Chen et al. .................. 424/85.2 |

2002/0137884 A1 9/2002 Arve et al.

FOREIGN PATENT DOCUMENTS

| | | | |
|---|---|---|---|
| EP | 0 473 564 A1 | | 3/1992 |
| EP | 0 559 632 | * | 9/1993 |
| EP | 0 559 632 A2 | | 9/1993 |
| EP | 0 414 374 B1 | | 10/1997 |
| EP | 0 755 438 B1 | | 2/2001 |
| WO | WO 93/18150 A1 | | 9/1993 |
| WO | WO 93/24143 | | 12/1993 |
| WO | WO 93/25230 A1 | | 12/1993 |
| WO | WO 96/01272 A1 | | 1/1996 |
| WO | WO 96/01273 A1 | | 1/1996 |
| WO | WO 96/01649 | | 1/1996 |
| WO | WO 96/04378 | | 2/1996 |
| WO | WO 96/40224 | | 12/1996 |
| WO | WO 97/09063 | | 3/1997 |
| WO | WO 99/57280 | | 11/1999 |
| WO | WO 01/64922 A2 | | 9/2001 |
| WO | WO 03/032904 | | 4/2003 |
| WO | 2005/019265 | * | 3/2005 |

OTHER PUBLICATIONS

Hwang et al., "Co-Expression of glutathione S-transferase with methionine aminopeptidase: A system of producing enriched N-terminal processed proteins in *Escherichia coli*", Biochemical Journal, vol. 338, No. 2, Mar. 1, 1999, pp. 335-342.
Ben-Bassat et al., "Processing of the initiation methionine from proteins: properties of the *Escherichia coli* methionine aminopeptidase and its gene structure", Journal of Bacteriology, vol. 169, No. 2, Feb. 1987, pp. 751-757.
Rainer Rudolph, "Successful Protein Folding on an Industrial Scale", Protein Engineering: Principles and Practice, Chapter 10, pp. 283-298 (1996).
Dabora et al., "Effect of Polyanions on the Refolding of Human Acidic Fibroblast Growth Factor", The Journal of Biological Chemistry, vol. 266, No. 35, pp. 23637-23640 (1991).
Bernhard Fisher et al., "Isolation, Renaturation, and Formation of Disulfide Bonds of Eukaryotic Proteins Expressed in *Escherichia coli* as Inclusion Bodies", Biotechnology and Bioengineering, vol. 41, pp. 3-13 (1993).
J. Harenberg, et al., Tissue Factor Pathway Inhibitor: Proposed Heparin Recognition Region, Blood Coagulation and Fibrinolysis, vol. 6, Supp. No. 1, pp. S50-S56 (1995).

(Continued)

*Primary Examiner*—Karen Cochrane Carlson
(74) *Attorney, Agent, or Firm*—Banner & Witcoff, Ltd.

(57) ABSTRACT

Highly purified preparations of TFPI or TFPI analogs can be prepared using a method that generally involves the following steps: (1) expression of TFPI or TFPI analog in *E. coli*, (2) isolation of refractile bodies, (3) dissolution of the refractile bodies and refolding of the expressed TFPI or TFPI analog, (4) SP-Sepharose fast flow (FF) chromatography, (5) a first concentration and diafiltration step, (6) Q-Sepharose high (HP) performance chromatography, (7) butyl hydrophobic interaction chromatography (HIC), (8) SP-Sepharose HP chromatography, and (9) a second concentration/diafiltration step. Less than about 12% of the TFPI or TFPI analog molecules in such preparations are modified TFPI or TFPI analog species (i.e., oxidized, carbamylated, acetylated, deamidated, aggregated, or misfolded species).

62 Claims, 18 Drawing Sheets

OTHER PUBLICATIONS

Mark E. Gustafson et al., "Renaturation and Purification of Human Tissue Factor Pathway Inhibitor Expressed in Recombinant *E. coli*, Protein Expression and Purification", vol. 5, pp. 233-241 (1994).

Curless et al., "Phosphate Glass as a Phosphate Source in High Cell Density *Escherichia coli* Fermentations", *Biotechnology Progress*, vol. 12, pp. 22-25 (1996) XP002238061.

Malaoui et al., "Influence of Glucose on Glycerol Metabolism by Wild-Type and Mutant Strains of *Colostridium butyricum* E5 grown in Chemostat Culture", *Applied Microbiology and Biotechnology*, vol. 55, Dec. 2000, pp. 226-233, XP002237996.

Vagabov et al., "Dependence of Inorganic Polyphosphate Chain Length on the Orthophosphate Content in the Culture Medium of the Yeast *Saccharomyces Cerevisiae*", *Biochemistry* (Moscow), vol. 65, 2000, pp. 349-354, XP002237997.

Albertson et al., "Growth and Survival of *Helicobacter pylori* in Defined Medium and Susceptibility to Brij 78", *Journal of Clinical Microbiology*, vol. 36, 1998, pp. 1232-1235, XP002238062.

Bauer et al., "Improved Expression of Human Interleukin-2 in High-Cell-Density-Density Fermentor Cultures of *Escherichia coli* K-12 by a Phosphotransacetylase Mutant", 1990, *Appl. Environ. Microbiol.I*, 56: 1296-1302.

Bonsignore et al., "Development of a Chemically Defined Medium for Bacterial Biotin Production", 1989, *Abstr. Pap. Am. Chem. Soc.* 198 Meet, MBTD 199.

Box & Wilson, "On the Experimental Attainment of Optimum Conditions", 1951, *J. Roy. Statist. Soc.*, B13: 1-45.

Chalmers et al., "Effects of Temperature on *Escherichia coli* Overproducing β-Lactamase or Human Epidermal Growth Factor", 1990, *Appl. Environ. Microbiol.*, 56: 104-111.

Evans, D.J. et al., "Identification of Four New Prokaryotic Bacterioferritins, from *Helicobacter pylori, Anabaena variabilis, Bacillus subtilis* and *Treponema pallidum*, by Analysis of Gene Sequence", 1995, Gene, 153: 123-127.

De Vuyst, L., "Nutritional Factors Affecting Nisin Production by *Lactococcus lactis* Subsp. *Lactis NIZO 22186* in a Synthetic Medium", 1995, *J. Appl. Bacteriol.*, 78: 28-33.

Galindo et al., "Maximizing the Expression of Recombinant Proteins in *Escherichia coli* by Manipulation of Culture Conditions", 1990, *J. Ferm. Bioeng.*, 69: 159-165.

Konstantinov et al., "Physiologically Motivated Strategies for Control of the Fed-Batch Cultivation of Recombinant *Escherichia coli* for Phenylalanine Production", 1991, *J. Ferm. Bioeng.*, 71: 350-355.

Kopetzki et al., "Control of Formation of Active Soluble or Inactive Insoluble Baker's Yeast α-Glucosidase PI in *Escherichia coli* by Induction and Growth Conditions", 1989, *Mol. Gen. Genet.*, 216: 149-155.

Lee & Lee, "Enhanced Production of Poly(3-hydroxybutyrate) by Filamentation-Suppressed Recombinant *Escherichia coli* in a Defined Medium", 1996, *Journal of Environmental Polymer Degradation*, 4(2): 131-134.

Luli & Strohl., "Comparison of Growth, Acetate Production, and Acetate Inhibition of *Escherichia coli* Strains in Batch and Fed-Batch Fermentations", 1990, *Appl. Environ. Microbiol.*, 56: 640-645.

MacDonald & Neway, "Effects of Medium Quality on the Expression of Human Interleukin-2 at High Cell Density in Fermentor Cultures of *Escherichia coli* K-12", 1990, *Appl. Environ. Microbiol.*, 56: 640-645.

Manetti, R. et al., "*Helicobacter pylori* Cytotoxin: Importance of Native Conformation for Induction of Neutralizing Antibodies", 1995, *Infect. Immun.*, 63: 4476-4480.

Okita et al., "Effect of Induction Temperature on the Production of Malaria Antigens in Recombinant *E. coli*", 1989, *Biotechnol. Bioeng.*, 34: 854-862.

Park & Ryu, "Effect of Operating Parameters on Specific Production Rate of a Cloned-Gene Product and Performance of Recombinant Fermentation Process" 1990, *Biotechnol. Bioeng.*, 35: 287-295.

Rappuoli et al., "Development of a Vaccine Against *Helicobacter Pylori*: A Short Overview", 1993, *European Journal of Gastroenterology and Hepatology of Helicobacter Pylori Infection*, Proceedings of an Interdisciplinary Meeting (Geneva, Jun. 18-19, 1993) J.J. Misiewicz, Ed. (CS Current Science) pp. S76-S78.

Rappuoli, R., "Toxin Inactivation and antigen Stabilization: Two Different Uses of Formaldehyde", 1994, *Vaccine*, 12(7): 579-581.

Rinas et al., "Glucose as a Ssubstrate in Recombinant Strain Fermentation Technology", 1989, *Appl. Microbiol. Biotechnol.*, 31: 163-167.

Stephenne, J., "Development and Production Aspects of a Recombinant Yeast-Derived Hepatitis B Vaccine", 1990, *Vaccine*, 8: S69-S73.

Stratakalaitis et al., "Development of an *Escherichia coli* Culture and Fermentation Process for $P_L$-Regulated Expression of HIV-1 Protease," 1991, *Abstr. Gen. Meet. Am. Soc. Microbiol.*, 91 Meet, 190.

Zhang et al., "Process Characterization Studies to Facilitate Validation of a Recombinant Protein Fermentation," 1998, in: Kelley & Ramelmeier (eds) *ACS Symposium Ser* 698: 12-27.

Zhang & Greasham, "Chemically Defined Media for Commercial Fermentations," 1999, *Appl. Microbiol. Biotechnol.*, 51:407-421.

Moser, A. (1985) Chapters 14-16 of *Fundamentals of Biochemical Engineering* (ed. Brauer).

Carr et al., Circulatory Shock, 44(3): 126-37 (1994).

Abraham et al., "Efficacy and Safety of Tifacogin (Recombinant Tissue Factor Pathway Inhibitor) in Severe Sepsis; A Randomized Controlled Trial," JAMA, Jul. 9, 2003, pp. 238-247, vol. 290, No. 2, American Medical Association.

Angus et al., "Unraveling Severe Sepsis; Why did OPTIMIST Fail and What's Next?" JAMA, Jul. 9, 2003, pp. 256-258, vol. 290, No. 2, American Medical Association.

\* cited by examiner

FIG. 15

```
                    → tac promoter
   BamHI    SacII            -35 region of              -10 region of
     |       |                 promoter                  lac promoter
       GGATCCCGCGGTTCTGAAATGAGCTGTTGACAATTAATCATCGGCTCGTATAATGTGTGG
  1    ---------+---------+---------+---------+---------+---------+ 60
       CCTAGGGCGCCAAGACTTTACTCGACAACTGTTAATTAGTAGCCGAGCATATTACACACC

|→Transcription start site
       |                     BglII
       | lac operator         |        g10-L fragment
       AATTGTGAGCGGATAACAATTTCACACAGATCTGGGCCCTTCGAAATTAATACGACTCAC
 61    ---------+---------+---------+---------+---------+---------+ 120
       TTAACACTCGCCTATTGTTAAAGTGTGTCTAGACCCGGGAAGCTTTAATTATGCTGAGTG XbaI                       Shine-
                                    |                         Dalgarno
       TATAGGGAGACCACAACGGTTTCCCTCTAGAAATAATTTTGTTTAACTTTAAGAAGGAGA
121    ---------+---------+---------+---------+---------+---------+ 180
       ATATCCCTCTGGTGTTGCCAAAGGGAGATCTTTATTAAAACAAATTGAAATTCTTCCTCT NcoI
           |  → Met-Ala-TFPI gene N terminus
       TATATCCATGGCTGATTCTGAAGAAGATGAAGAACATACTATTATCACTGATACTGAACT
181    ---------+---------+---------+---------+---------+---------+ 240
       ATATAGGTACCGACTAAGACTTCTTCTACTTCTTGTATGATAATAGTGACTATGACTTGA MetAlaAspSerGluGluAspGluGluHisThrIleIleThrAspThrGluLeu   -

NsiI
                    |                            T  T     A   T
       GCCACCGCTGAAACTGATGCATTCATTTTGTGCATTCAAGGCGGACGACGGCCCGTGCAA
241    ---------+---------+---------+---------+---------+---------+ 300
       CGGTGGCGACTTTGACTACGTAAGTAAAACACGTAAGTTCCGCCTGCTGCCGGGCACGTT

ProProLeuLysLeuMetHisSerPheCysAlaPheLysAlaAspAspGlyProCysLys  -

A        AA  A    T          T   T       A
       AGCCATCATGAAGCGCTTCTTCTTCAACATCTTCACTCGTCAGTGCGAAGAATTTATATA
301    ---------+---------+---------+---------+---------+---------+ 360
       TCGGTAGTACTTCGCGAAGAAGAAGTTGTAGAAGTGAGCAGTCACGCTTCTTAAATATAT

AlaIleMetLysArgPhePhePheAsnIlePheThrArgGlnCysGluGluPheIleTyr  -
                  39
```

FIG. 15 CONTINUED

```
                                  ClaI
                                   |           AAGT  G      G     A  A
     TGGGGGATGTGAAGGAAATCAGAATCGATTTGAGTCCCTCGAAGAATGCAAGAAGATGTG
361  ---------+---------+---------+---------+---------+---------+  420
     ACCCCCTACACTTCCTTTAGTCTTAGCTAAACTCAGGGAGCTTCTTACGTTCTTCTACAC

GlyGlyCysGluGlyAsnGlnAsnArgPheGluSerLeuGluGluCysLysLysMetCys  -
                                                                 75

T  AA A  T  T
     CACCCGCGACAACGCAAACAGGATTATAAAGACAACATTGCAACAAGAAAAGCCAGATTT
421  ---------+---------+---------+---------+---------+---------+  480
     GTGGGCGCTGTTGCGTTTGTCCTAATATTTCTGTTGTAACGTTGTTCTTTTCGGTCTAAA

ThrArgAspAsnAlaAsnArgIleIleLysThrThrLeuGlnGlnGluLysProAspPhe  -

CTGCTTTTTGGAAGAAGATCCTGGAATATGTCGAGGTTATATTACCAGGTATTTTTATAA
481  ---------+---------+---------+---------+---------+---------+  540
     GACGAAAAACCTTCTTCTAGGACCTTATACAGCTCCAATATAATGGTCCATAAAAATATT

CysPheLeuGluGluAspProGlyIleCysArgGlyTyrIleThrArgTyrPheTyrAsn  -

CAATCAGACAAAACAGTGTGAACGTTTCAAGTATGGTGGATGCCTGGGCAATATGAACAA
541  ---------+---------+---------+---------+---------+---------+  600
     GTTAGTCTGTTTTGTCACACTTGCAAAGTTCATACCACCTACGGACCCGTTATACTTGTT

AsnGlnThrLysGlnCysGluArgPheLysTyrGlyGlyCysLeuGlyAsnMetAsnAsn  -

TTTTGAGACACTGGAAGAATGCAAGAACATTTGTGAAGATGGTCCGAATGGTTTCCAGGT
601  ---------+---------+---------+---------+---------+---------+  660
     AAAACTCTGTGACCTTCTTACGTTCTTGTAAACACTTCTACCAGGCTTACCAAAGGTCCA

PheGluThrLeuGluGluCysLysAsnIleCysGluAspGlyProAsnGlyPheGlnVal  -

GGATAATTATGGAACCCAGCTCAATGCTGTGAATAACTCCCTGACTCCGCAATCAACCAA
661  ---------+---------+---------+---------+---------+---------+  720
     CCTATTAATACCTTGGGTCGAGTTACGACACTTATTGAGGGACTGAGGCGTTAGTTGGTT

AspAsnTyrGlyThrGlnLeuAsnAlaValAsnAsnSerLeuThrProGlnSerThrLys  -

GGTTCCCAGCCTTTTTGAATTTCACGGTCCCTCATGGTGTCTCACTCCAGCAGACAGAGG
721  ---------+---------+---------+---------+---------+---------+  780
     CCAAGGGTCGGAAAAACTTAAAGTGCCAGGGAGTACCACAGAGTGAGGTCGTCTGTCTCC

ValProSerLeuPheGluPheHisGlyProSerTrpCysLeuThrProAlaAspArgGly  -

ATTGTGTCGTGCCAATGAGAACAGATTCTACTACAATTCAGTCATTGGGAAATGCCGCCC
781  ---------+---------+---------+---------+---------+---------+  840
     TAACACAGCACGGTTACTCTTGTCTAAGATGATGTTAAGTCAGTAACCCTTTACGGCGGG

LeuCysArgAlaAsnGluAsnArgPheTyrTyrAsnSerValIleGlyLysCysArgPro  -
```

FIG. 15 CONTINUED

```
      ATTTAAGTACAGTGGATGTGGGGAAATGAAAACAATTTTACTTCCAAACAAGAATGTCT
841   ---------+---------+---------+---------+---------+---------+  900
      TAAATTCATGTCACCTACACCCCCTTTACTTTTGTTAAAATGAAGGTTTGTTCTTACAGA

PheLysTyrSerGlyCysGlyGlyAsnGluAsnAsnPheThrSerLysGlnGluCysLeu  -

GAGGGCATGTAAAAAAGGTTTCATCCAAAGAATATCAAAAGGAGGCCTAATTAAAACCAA
901   ---------+---------+---------+---------+---------+---------+  960
      CTCCCGTACATTTTTTCCAAAGTAGGTTTCTTATAGTTTTCCTCCGGATTAATTTTGGTT

ArgAlaCysLysLysGlyPheIleGlnArgIleSerLysGlyGlyLeuIleLysThrLys -

C terminus of Ala-TFPI coding sequence
      AAGAAAAAGAAAGAAGCAGAGAGTGAAAATAGCATATGAAGAAATTTTTGTTAAAAATAT
961   ---------+---------+---------+---------+---------+---------+ 1020
      TTCTTTTTCTTTCTTCGTCTCTCACTTTTATCGTATACTTCTTTAAAAACAATTTTATA ArgLysArgLysLysGlnArgValLysIleAlaTyrGluGluIlePheValLysAsnMet -

Stop  HindIII
      TGA^^^AAGCTT (in pMON6655)
       | Translation Termination
       |  HindIII ClaI                              EcoRI   EcoRV  P22 term delta
       |    |      |                                  |       |      |
      GTAATAAAAGCTTATCGATGATAAGCTGTCAAACATGAGAATTCGATATCAACGCAACGA
1021  ---------+---------+---------+---------+---------+---------+ 1080
      CATTATTTTCGAATAGCTACTATTCGACAGTTTGTACTCTTAAGCTATAGTTGCGTTGCT EndEnd
                                       EcoRV  EcoRI
                                         |      |
      CCCAGCCGAAGCTGGGTCGTTGCGTTGATATCGAATTC
1081  ---------+---------+---------+-------   1118
      GGGTCGGCTTCGACCCAGCAACGCAACTATAGCTTAAG
```

METHOD OF PURIFYING TFPI AND TFPI ANALOGS

This application claims the benefit of and incorporates by reference provisional applications Ser. No. 60/494,546 filed Aug. 13, 2003, Ser. No. 60/509,277 filed Oct. 8, 2003, Ser. No. 60/512,199 filed Oct. 20, 2003.

FIELD OF THE INVENTION

The invention relates to the production of purified TFPI.

BACKGROUND OF THE INVENTION

Tissue factor pathway inhibitor (TFPI) is 276 amino acids in length and functions as an inhibitor of tissue factor-mediated blood coagulation. See U.S. Pat. No. 4,966,852. The amino terminal end of TFPI is negatively charged, and the carboxy terminal end is positively charged. The TFPI protein contains three Kunitz-type enzyme inhibitor domains. TFPI contains 18 cysteine residues and forms 9 disulfide bridges when correctly folded. The primary sequence contains three N-linked consensus glycosylation sites (Asn-X-Ser/Thr). The asparagine residues of the glycosylation sites are located at positions 145, 195 and 256. TFPI is also known as lipoprotein associated coagulation inhibitor (LACI), tissue factor inhibitor (TFI), and extrinsic pathway inhibitor (EPI).

Use of TFPI has been proposed for the treatment of various indications, including sepsis (U.S. Pat. No. 6,063,764 and WO 93/24143), deep vein thrombosis (U.S. Pat. No. 5,563,123, U.S. Pat. No. 5,589,359, and WO 96/04378), ischemia (U.S. Pat. No. 5,885,781, U.S. Pat. No. 6,242,414, and WO 96/40224), restenosis (U.S. Pat. No. 5,824,644 and WO 96/01649), and cancer (U.S. Pat. No. 5,902,582 and WO 97/09063). A TFPI variant, which differs from TFPI by the addition of an alanine residue at the amino terminus ("ala-TFPI"), has been shown to be efficacious in animal models for the treatment of sepsis. Carr et al., *Circ. Shock* 44(3), 126-37, 1994.

There is a continuing need in the art for biologically active, purified TFPI and methods of obtaining it.

SUMMARY OF THE INVENTION

The invention provides at least the following embodiments.

One embodiment of the invention provides a purified preparation comprising a plurality of TFPI or TFPI analog molecules. Less than about 12% of the TFPI or TFPI analog molecules are modified species. The modified species include one or more of the following: an oxidized TFPI or TFPI analog molecule, as detected by reverse phase chromatography; a carbamylated TFPI or TFPI analog molecule, as detected by cation exchange chromatography; a deamidated TFPI or TFPI analog molecule, as detected by a Promega ISOQUANT® kit; a TFPI or TFPI analog molecule that comprises a cysteine adduct, as determined by amino acid analysis; aggregated TFPI or TFPI analog molecules, as detected by size exclusion chromatography; and a misfolded TFPI or TFPI analog molecule, as detected by non-denaturing SDS-polyacrylamide gel electrophoresis.

Another embodiment of the invention is a pharmaceutical formulation comprising a plurality of TFPI or TFPI analog molecules. Less than about 12% of the TFPI or TFPI analog molecules are modified species. The modified species include one or more of the following: an oxidized TFPI or TFPI analog molecule, as detected by reverse phase chromatography; a carbamylated TFPI or TFPI analog molecule, as detected by cation exchange chromatography; a deamidated TFPI or TFPI analog molecule, as detected by a Promega ISOQUANT® kit; a TFPI or TFPI analog molecule that comprises a cysteine adduct, as determined by amino acid analysis; aggregated TFPI or TFPI analog molecules, as detected by size exclusion chromatography; and a misfolded TFPI or TFPI analog molecule, as detected by non-denaturing SDS-polyacrylamide gel electrophoresis.

Another embodiment of the invention provides a method of producing purified TFPI or TFPI analog. The method comprises the following steps: (1) expressing TFPI or TFPI analog in a rifampicin-resistant *E. coli* host cell, (2) isolating inclusion bodies containing the TFPI or TFPI analog from the *E. coli* host cell, (3) isolating the TFPI or the TFPI analog from the inclusion bodies to obtain isolated TFPI or TFPI analog, (4) refolding the isolated TFPI or TFPI analog to form refolded TFPI or TFPI analog, (5) purifying the refolded TFPI or TFPI analog by SP-Sepharose fast flow chromatography in the presence of $Mg^{++}$ to form a first preparation of purified TFPI or TFPI analog, (6) concentrating the first preparation of purified TFPI or TFPI analog to form a first concentrated preparation of purified TFPI or TFPI analog, (7) purifying the first concentrated preparation of purified TFPI or TFPI analog by Q-Sepharose HP chromatography to form a second preparation of purified TFPI or TFPI analog, (8) purifying the second preparation of purified TFPI or TFPI analog by butyl HIC chromatography to form a third preparation of purified TFPI or TFPI analog, (9) purifying the third preparation of purified TFPI or TFPI analog by SP-Sepharose HP chromatography to form a fourth preparation of purified TFPI or TFPI analog, and (10) concentrating the fourth preparation of purified TFPI or TFPI analog to form a second concentrated preparation of purified TFPI or TFPI analog molecules, wherein less than about 12% of the TFPI or TFPI analog molecules are modified species. The TFPI or TFPI analog is encoded on a plasmid comprising the following elements: (a) a transcription promoter; (b) a ribosome binding site adjacent to the transcription promoter; (c) a nucleotide coding sequence that encodes the TFPI or the TFPI analog adjacent to the ribosome binding site; (d) a transcription terminator adjacent to the nucleotide coding sequence; (e) a replicon; (f) an antibiotic resistance gene; and (g) a gene encoding an N-terminal methionine-removing enzyme.

Another embodiment of the invention is a method of producing purified TFPI or TFPI analog. The method comprises the following steps: (1) purifying the refolded TFPI or TFPI analog by SP-Sepharose fast flow chromatography to form a first preparation of purified TFPI or TFPI analog, (2) concentrating the first preparation of purified TFPI or TFPI analog to form a first concentrated preparation of purified TFPI or TFPI analog, (3) purifying the first concentrated preparation of purified TFPI or TFPI analog by Q-Sepharose HP chromatography to form a second preparation of purified TFPI or TFPI analog, (4) purifying the second preparation of purified TFPI or TFPI analog by butyl HIC chromatography to form a third preparation of purified TFPI or TFPI analog, (5) purifying the third preparation of purified TFPI or TFPI analog by SP-Sepharose HP chromatography to form a fourth preparation of purified TFPI or TFPI analog, and (6) concentrating the fourth preparation of purified TFPI or TFPI analog to form a second concentrated preparation of purified TFPI or TFPI analog molecules, wherein less than about 12% of the TFPI or TFPI analog molecules are modified species.

Yet another embodiment of the invention is a method of expressing TFPI or TFPI analog, comprising culturing a rifampicin-resistant *E. coli* host cell in a fermentation medium. The *E. coli* host cell comprises a plasmid having the following elements: (a) a transcription promoter; (b) a ribosome binding site adjacent to the reclac transcription promoter; (c) a nucleotide coding sequence that encodes TFPI or TFPI analog adjacent to the ribosome binding site; (d) a transcription terminator adjacent to the nucleotide coding sequence; (e) a replicon; (f) an antibiotic resistance gene; and (g) a gene encoding an N-terminal methionine-removing enzyme. One liter of the fermentation medium comprises 41 g dextrose, 2.5 g $(NH_4)_2SO_4$, 4.0 g sodium polyphosphate, 7.0 g $K_2SO_4$, 1.63 g $MgSO_4.7H_2O$, 2.0 g methionine, 2.0 g glycerol, 0.5 mg $H_3BO_4$, 0.5 g cobalt chloride, 0.13 g $CuSO_4.6H_2O$, 54.0 g $FeCl_3.6H_2O$, 11.0 g $MnSO_4.H_2O$, 0.5 g $Na_2MoO_4.2H_2O$, 0.02 $NaSeO_3.22.0$ g $ZnSO_4.7H_2O$, 0.01 ml concentrated $H_2SO_4$, and 0.55 ml UCON antifoam.

Still another embodiment of the invention is a pharmaceutical composition comprising a plurality of ala-TFPI molecules and 20 mM sodium citrate, 300 mM L-arginine, and 5 mM methionine, pH 5.5. Less than about 12% of the ala-TFPI molecules are modified species. The modified species include one or more of the following: an oxidized ala-TFPI molecule, as detected by reverse phase chromatography; a carbamylated ala-TFPI molecule, as detected by cation exchange chromatography; a deamidated ala-TFPI molecule, as detected by a Promega ISOQUANT® kit; an ala-TFPI molecule that comprises a cysteine adduct, as determined by amino acid analysis; aggregated ala-TFPI molecules, as detected by size exclusion chromatography; and a misfolded ala-TFPI molecule, as detected by non-denaturing SDS-polyacrylamide gel electrophoresis.

BRIEF DESCRIPTION OF THE FIGURES

FIG. 6A, rTFPI lot MAECM014 (prepared according to Process B). FIG. 6B, rTFPI lot PB5806 (prepared according to Process C). The observed masses of major component are consistent with the theoretical molecular mass 32,004 Da.

FIG. 9A, rTFPI lot MAECM014. FIG. 9B, rTFPI lot PB5806.

FIG. 11A, materials prepared according to Process B. FIG. 11B, materials prepared according to Process C. Ten μg samples were applied to a Zorbax 300SB-CN column and separated using a gradient containing acetonitrile and 0.2% trifluoroacetic acid. The column eluent was monitored by UV absorbance at 214 nm. The minor peaks are rTFPI containing an oxidized methionine residue (1), rTFPI containing a norvaline for leucine substitution (2) and rTFPI containing an acetylated or carbamylated residue (3).

FIG. 12A, solid arrows indicate norvaline-containing peptides, dashed arrow indicates corresponding normal peptide T(88-108). FIG. 12B, SIM Chromatogram for Peptide T(88-108) m/z 1293.6. FIG. 12C, SIM Chromatogram for Peptide T(88-108) with norvaline misincorporation m/z 1286.6 where nV90 and nV100 correspond to norvaline at residue positions 90 and 100, respectively.

FIG. 14A, lot MAECM014. FIG. 14B, lot PB5806. FIG. 14C, lot PB6096. FIG. 14D, lot PB6770. The shaded lines indicate the regions of the UV chromatograms that were characterized by deconvoluted mass spectra. The early eluting region was identified as rTFPI containing methionine sulfoxide in approximately equal proportions in materials prepared according to Process B and those prepared according to Process C. The late eluting region was identified as rTFPI containing acetylated residues in materials prepared according to Process B.

FIG. 15. Nucleotide sequence of the expression cassette in pMON9197 (the upper nucleotide sequence is shown in SEQ ID NO:43). This sequence includes the transcription promoter, the ribosome binding site, the ala-TFPI gene with reduced translation initiation at both Met39 and Met75, and the transcription terminator. The nucleotides above the line are those present in pMON6875 or pMON6655 at those positions. The substitutions were made to reduce internal translation initiations, and they do not affect the sequence of the ala-TFPI protein encoded. The nucleotides above the line near the translation termination codons are present in pMON6655 in that region. The stop codon used in pMON6655 is TAG. The symbols ^^^ following the TAG represent a deletion of 64 nucleotides which includes one recognition site for ClaI and EcoRI. The sequence in pMON6655 following the HindIII site is identical to that in pMON9197 (except for the insertion of the MAP gene into pMON9197).

DETAILED DESCRIPTION OF THE INVENTION

Figure 1:
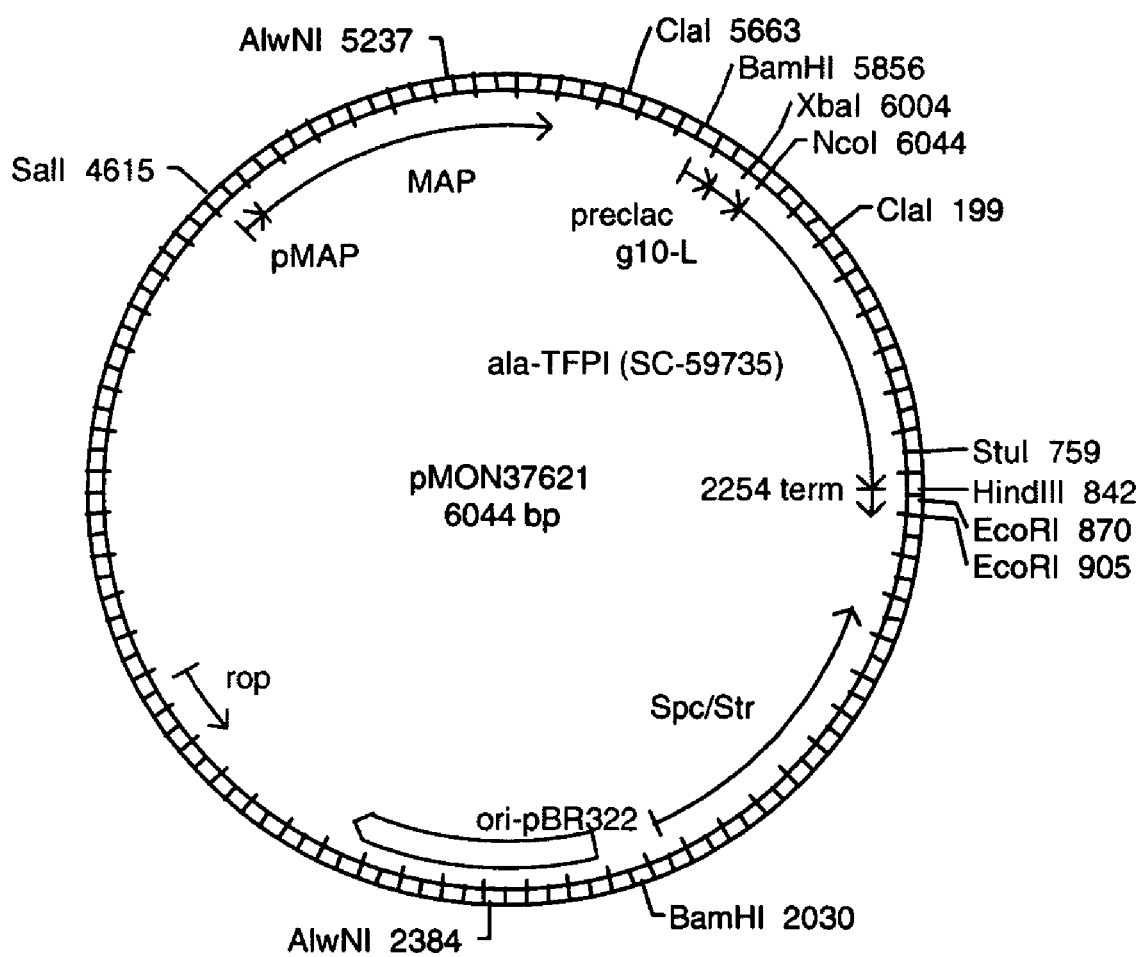
FIG. 1. Map of plasmid pMON37621.

The invention provides an improved method of purifying TFPI or a TFPI analog (defined below). The purification method is capable of producing preparations of TFPI or TFPI analog molecules in which less than about 12, 11, 10, 9, 8, 7, 6, 5, 4, 3, 2, 1, or 0.5% of the preparation consists of "modified species." "Modified species" are oxidized, carbamylated, deamidated, acetylated, aggregated, or misfolded TFPI or TFPI analogs.

The method is particularly suitable for preparing large-scale preparations of purified TFPI or TFPI analog, e.g., 200-300 g, 500 g, 400-600 g, 750 g, 600-900 g, 800 g, 800-1,200 g, 1.2 kg, or 2.4 kg of purified TFPI or TFPI analog as defined below.

TFPI or TFPI Analog

"TFPI" is non-glycosylated TFPI having the amino acid sequence shown in SEQ ID NO:1. "TFPI analogs" have a different primary amino acid structure than TFPI as shown in SEQ ID NO:1 (i.e., one or more amino acid substitutions, insertions, deletions, and/or additions) while retaining one or more of the biological activities of TFPI as discussed below. TFPI analogs have at least about 70%, preferably at least about 80%, more preferably at least about 90, 91, 92, 93, 94, 95, 96, 97, 98, or 99% amino acid sequence identity to the amino acid sequence of TFPI (SEQ ID NO:1). TFPI analogs include muteins, chimeric molecules, and fragments of TFPI. Any of these molecules may have one or more substitutions of norleucine for methionine or norvaline for leucine.

Percent homology between a TFPI analog and the amino acid sequence of TFPI (SEQ ID NO:1) is determined using the Blast2 alignment program (Blosum62, Expect 10, standard genetic codes, open gap 11, extension gap 1, gap x_dropoff 50, and low complexity filter off). Conservative substitutions, in which an amino acid is exchanged for another having similar properties, are preferred. Examples of conservative substitutions include, but are not limited to, Gly↔Ala, Val↔Ile↔Leu, Asp↔Glu, Lys↔Arg, Asn↔Gln, and Phe↔Trp↔Tyr. Conservative amino acid substitutions typically fall in the range of about 1 to 5 amino acids (i.e., 1, 2, 3, 4, or 5 amino acids). Additional amino acids can be added at any position in the molecule, particularly at the amino- or carboxy terminus. Amino acid additions can be 1, 2, 5, 10, 25, 100, or more additional amino acids. Fusion proteins are encompassed within the definition of analogs. Obviously, any alterations made in the DNA encoding a TFPI analog must not place the sequence out of reading frame and preferably will not create complementary regions that could produce secondary mRNA structure. Guidance in determining which amino acid residues can be substituted, inserted, or deleted without abolishing biological or immunological activity can be found using computer programs well known in the art, such as DNASTAR software, or in Dayhoff et al. (1978) in Atlas of Protein Sequence and Structure (Natl. Biomed. Res. Found., Washington, D.C.).

A preferred TFPI analog is N-L-alanyl-TFPI ("ala-TFPI"), which has an additional alanine residue at the amino terminal end of SEQ ID NO:1.

Analogs include "TFPI muteins" having 1-5 conservative amino acid substitutions relative to SEQ ID NO:1. Preferred muteins have substitutions that do not substantially change the conformation of the molecule. In some cases, TFPI muteins (1) have amino acid substitutions that eliminate one or more of the three sites for N-linked glycosylation, (2) have 1-5 amino acid substitutions that change a residue of TFPI (SEQ ID NO: 1) to a corresponding residue of TFPI-2, (3) have amino acid substitutions in $P_1$ reactive sites in one or more Kunitz-type domains, or (4) have amino acid substitutions at positions within 5 amino acids of the $P_1$ reactive sites in one or more Kunitz-type domains. In one TFPI mutein, the lysine residue in the $P_1$ reactive site of the first Kunitz-type domain of TFPI (SEQ ID NO:1) is replaced with arginine.

"Chimeric TFPI" molecules containing various portions of TFPI (SEQ ID NO:1) are described in U.S. Pat. No. 5,589,359.

Fragments are TFPI analogs that consist of portions of TFPI (SEQ ID NO:1). A fragment can be, for example, 20, 25, 30, 50, 100, 150, 200, 250, or 275 consecutive amino acids in length. Examples of fragments include Kunitz domains 1, 2, or 3; Kunitz domains 1 and 2 or 2 and 3; and deletions of the N-terminus, C-terminus, or both. Substantial guidance for making such analogs is found in U.S. Pat. No. 5,106,833.

Biological Activity of TFPI, TFPI Analogs, or Modified TFPI or TFPI Analogs

Biological activities of TFPI or modified TFPI (as defined below) include binding to and inhibiting the amidolytic activity of both factor VIIa/TF complex and factor Xa and anticoagulant activity, as measured in a prothrombin time (PT) assay. TFPI analogs, including modified TFPI analogs as defined below, preferably can bind either or both of the factor VIIa/TF complex and factor Xa. TFPI analogs, including modified TFPI analogs, preferably possess a substantial amount of anticoagulant activity, for example 10%, 30%, 50%, 60%, 80%, 90% or more of the anticoagulant activity of TFPI (SEQ ID NO:1) as measured in the PT assay described below.

Purified TFPI or TFPI Analog Preparations

Purified TFPI or TFPI analog preparations of the invention contain TFPI or TFPI analog molecules of which less than about 12% are modified species as detected by one or more of the assays described below. "Modified TFPI or TFPI analog species" are molecules with one or more of the following post-translational modifications: oxidation (oxidized methionine residues), cysteine adducts, amino acid modifications (residual N-terminal methionine, deamidation, acetylation, and carbamylation), aggregation (forming TFPI or TFPI analog oligomers), and misfolding.

Preferably, less than about 9, 8, 7, 6, 5, 4, 3, 2, or 1% of the TFPI or TFPI analog molecules in a purified preparation of the invention are oxidized, as detected by reversed phase chromatography (CN HPLC, described below). Preferably less than about 3, 2, 1, 0.5, 0.25, or 0.13% of the TFPI or TFPI analog molecules in a purified preparation of the invention are carbamylated, as detected by cation exchange chromatography (CEX HPLC, described below). In still other purified preparations, less than about 9, 8, 7, 6, 5, 4, 3, 2, 1, or 0.5% of the TFPI or TFPI analog molecules in a purified TFPI or TFPI analog preparation are deamidated as measured using a Promega ISOQUANT® kit. Preferably, less than about 2, 1, 0.5, 0.25, or 0.13% of the TFPI or TFPI analog molecules in a purified preparation of the invention have cysteine adducts as determined by amino acid analysis. In other preferred TFPI or TFPI analog preparations, less than about 3, 2, 1, 0.5, 0.25, or 0.13% of the TFPI or TFPI analog molecules are aggregated, as detected by size exclusion chromatograph (SEC HPLC) or are misfolded, as detected by SDS polyacrylamide gel electrophoresis (SDS-PAGE) under non-reducing conditions (as described below).

Preferably, purified TFPI or TFPI analog preparations do not contain levels of acetylated TFPI or TFPI analog species detectable by mass spectroscopy (as described below). Purified preparations of the invention also preferably are substantially free of E. coli proteins, i.e., less than 2 ng/mg of the protein in a purified TFPI or TFPI analog preparation detectable on a silver-stained SDS polyacrylamide gel is E. coli protein.

Other preferred purified TFPI or TFPI analog preparations contain less than about 4% oxidized TFPI or TFPI analog species, less than about 1% carbamylated TFPI or TFPI analog species, less than about 5% deamidated TFPI or TFPI analog species, and less than about 3% aggregated and/or misfolded TFPI or TFPI analog species.

Any of the purified TFPI preparations of the invention can contain one or more substitutions of norleucine for methionine or norvaline for leucine.

Assays

The assays described below are used to determine purity, stability, or biological activity of TFPI or TFPI analog preparations.

Purity by Reversed Phase Chromatography (CN HPLC)

A reversed phase high performance liquid chromatography method (CN HPLC) is used to detect modified TFPI or TFPI analog species, i.e., TFPI or TFPI analog molecules with modifications such as oxidized methionine residues, and amino acid modifications such as residual N-terminal methionine, carbamylation, deamidation, and acetylation. CN HPLC also can detect TFPI or TFPI analog species having substitutions of norleucine for methionine; as noted above, however, such species are not "modified TFPI or TFPI analog species" and can be present in purified preparations of the invention.

The CN HPLC method uses a stable bonded, cyano-reverse phased column and mobile phase containing acetonitrile and 0.2% trifluoroacetic acid. Elution is monitored for protein by detecting absorbance at 214 nm. Sample results are compared to a reference standard. Purity is assessed by area percent of the main peak.

As measured by CN HPLC, less than about 9, 8, 7, 6, 5, 4, 3, 2, or 1% of the TFPI or TFPI analog molecules in a purified TFPI or TFPI analog preparation have an oxidized methionine residue.

Quantitation of Free Cysteine by Amino Acid Analysis

Any method of amino acid analysis that permits quantitation of free cysteine can be used to quantitate TFPI or TFPI analog molecules that have a cysteine adduct. For example, see the methods disclosed in Barkholt & Jensen, Anal Biochem. 1989 March; 177(2):318-22; Hoogerheide & Campbell, Anal Biochem. 1992 Feb. 14; 201(1):146-51; Atherton et al., Anal Biochem. 1993 July; 212(1):98-105; Hale et al., Anal Biochem. 1994 January; 216(1):61-6; Manneberg et al., Anal Biochem. 1995 Nov. 1; 231(2):349-53; Thannhauser et al., J Protein Chem. 1998 January; 17(1):37-43; Yan et al., J Chromatogr A. 1998 Jul. 10; 813(1):187-200; U.S. Pat. No. 4,670,403; and U.S. Pat. No. 4,784,962. Typically, free cysteine released after reducing TFPI or TFPI analog molecules is quantitated.

As determined by amino acid analysis, less than about 2, 1, 0.5, 0.25, or 0.13% of the TFPI or TFPI analog molecules in a purified preparation of the invention have a cysteine adduct; most preferably, purified TFPI or TFPI analog preparations contain no detectable levels of cysteine adducts.

Deamidation Assay

The Promega ISOQUANT® kit (Promega Technical Bulletin No. TBI001 (ISOQUANT® Isoaspartate Detection Kit, revision 8/99) or its equivalent is used to determine TFPI or TFPI analog deamidation through the indirect measurement of isoaspartic acid. Briefly, the kit employs Protein Isoaspartyl Methyl Transferase (PIMT) which catalyzes the transfer of a methyl group from S-adenosyl-L-methionine (SAM) to isoaspartic acid. This reaction generates the byproduct S-adenosyl-homocysteine (SAH) that is subsequently analyzed by RP-HPLC (Carlson & Riggin, *Analytical Biochemistry* 278, 150-55, 2000) in order to quantitate the level of protein deamidation.

As measured by this assay, less than about 9, 8, 7, 6, 5, 4, 3, 2, 1, or 0.5% of the TFPI or TFPI analog molecules in a purified TFPI or TFPI analog preparation are deamidated.

Size Exclusion Chromatography (SEC HPLC)

Size exclusion chromatography (SEC HPLC) is used to detect TFPI or TFPI analog monomers from TFPI or TFPI analog oligomers (i.e., aggregated forms). The method uses a BioRad Bio-Sil SEC 250-5 and a mobile phase containing 40% acetonitrile and 0.75% trifluoroacetic acid. The elution is monitored for protein by absorbance at 214 nm. Monomers and oligomers are resolved based on their hydrodynamic radius. Purity is assessed by area percent.

Two methods of size exclusion chromatography can be used detect aggregated forms of TFPI or TFPI analogs. One method uses a 40% ACN, 0.75% TFA, 50 mM $MgCl_2$ buffer as the eluent and a UV detector set to 220 nm. The other method uses a formulation buffer (300 mM L-arginine, 20 mM sodium citrate, pH 5.5) as the eluent and a fluorescence detector set for excitation at 280 nm and emission at 320 nm; mass balance across the SEC column with this system is 85%.

As measured by SEC HPLC, less than about 3, 2, 1, 0.5, 0.25, or 0.13% of the TFPI or TFPI analog molecules in a purified TFPI or TFPI analog preparation are aggregated.

SDS-PAGE (Coomassie Blue Staining, Non-Reduced)

Sodium dodecyl sulfate polyacrylamide gel electrophoresis (SDS-PAGE) carried out under non-reducing conditions and with Coomassie Blue staining is used to detect misfolded TFPI or TFPI analog species. The method uses a 14% acrylamide gel and colloidal Coomassie staining. The reduced and non-reduced samples are compared to reference standard. Under non-reduced conditions, misfolded forms of TFPI or TFPI analog have a slightly greater electrophoretic mobility than TFPI or TFPI analog, whereas under reducing conditions there is no difference in the electrophoretic mobility. The results are compared to a reference standard to determine the percent of aggregated and/or misfolded species in a purified preparation.

As measured by SDS PAGE, less than about 3, 2, 1, 0.5, 0.25, or 0.13% of the TFPI or TFPI analog molecules in a purified preparation of the invention are misfolded.

SDS-Page (Silver Stain)

SDS PAGE carried out under denaturing conditions and using silver staining is used to identify *E. coli* proteins that were not removed during the purification process. The samples are reduced prior to application to a 14% acrylamide gel. Sample results are compared to a reference standard.

Purified TFPI or TFPI analog preparations are substantially free of *E. coli* proteins, i.e., less than 2 ng/mg of the protein in a purified preparation of the invention detectable on a silver-stained SDS polyacrylamide gel is *E. coli* protein.

CEX HPLC

Cation exchange chromatography (CEX HPLC) is used to detect the presence of carbamylated or charge-related TFPI or TFPI analog species. The CEX-HPLC method uses a Pharmacia Mono-S HR 5/5-glass column. The column is equilibrated in 80% buffer A (20 mM sodium acetate trihydrate:acetonitrile solution (70:30 v/v) at pH 5.4) and 20% buffer B (20 mM sodium acetate trihydrate-1.0 M ammonium chloride-acetonitrile solution (70:30 v/v) at pH 5.4). After a sample is injected, a gradient is applied to elute the TFPI at a flow rate of 0.7 ml/min from 20% buffer B to 85% buffer B in 21 minutes. Protein peaks are detected by absorbance at 280 nm or fluorescence using an excitation 280 nm and emission 320 nm.

As measured by CEX HPLC, less than about 3, 2, 1, 0.5, 0.25, or 0.13% of the TFPI or TFPI analog molecules in a purified preparation of the invention are carbamylated.

Mass Spectroscopy

Mass spectroscopy methods are described in the specific examples, below. Purified TFPI preparations of the invention preferably do not contain detectable levels of acetylated TFPI species as assayed by mass spectroscopy.

Prothrombin Time Assay

The PT assay is performed on a Coag-A-Mate MTX II instrument (Organon Teknika). TFPI or TFPI analog samples are first diluted to 150 µg/ml with buffer (2 M urea, 20 mM sodium phosphate, 250 mM NaCl, pH 7.2), then to 30 µg/ml with TBSA buffer (50 mM Tris, 100 mM NaCl, 1 mg/ml bovine serum albumin, pH 7.5) and finally to 12 to 15 µg/ml by TBSA buffer. For assay, 10 µl of diluted sample is first mixed with 90 µl of pooled Verify I (Organon Teknika, Cat. No. 59566), loaded on a test tray (Organon Teknika, Cat. No. 35014), and placed into the Coag-A-Mate. Then 200 II of Simplastin Excel (Organon Teknika, Cat. No. 52001) is added to initiate the clotting process. The clotting time is converted to the input TFPI or TFPI analog concentration by comparing with a standard plot of the log of the clotting time in seconds versus the log of the TFPI or TFPI analog concentration in the standards. Relative potency is calculated by comparing the inhibitory activity of TFPI or TFPI analog in the test samples to the inhibitory activity of the TFPI or TFPI analog control.

Overview of Purification Procedure

The purification method of the invention ("Process C") generally involves the following steps: (1) expression of TFPI or TFPI analog in *E. coli*, (2) isolation of refractile bodies, (3) dissolution of the refractile bodies and refolding of the expressed TFPI or TFPI analog, (4) SP-Sepharose fast flow (FF) chromatography, (5) a first concentration and diafiltration step, (6) Q-Sepharose high (HP) performance chromatography, (7) butyl hydrophobic interaction chromatography (HIC), (8) SP-Sepharose HP chromatography, and (9) a second concentration/diafiltration step. Optionally, a concentration/diafiltration step can be included between the butyl HIC and SP-Sepharose HP chromatography step. The purification method of the invention produces preparations of TFPI or TFPI analog molecules that contain fewer modified TFPI or TFPI analog species than previous purification methods described in Gustafson et al., *Protein Expression and Purification* 5, 233-41, 1994; WO 96/40784; U.S. Pat. No. 6,319,896; and U.S. Pat. No. 6,323,326 ("Process B").

The purification of TFPI or TFPI analog is largely achieved after the folding step by a sequence of chromatography operations. Aside from the SP sepharose capture column, which uses a step elution, the remaining chromatography steps all use fraction collection and analysis to determine which fractions should be pooled. From a practical manufacturing perspective, fractions should meet certain minimum requirements for pooling. However if desired, an increased level in purity can be obtained if only the peak fractions are collected and carried through the subsequent chromatography operation. By removing these modified forms of TFPI, this purification method is capable of producing preparations of TFPI or TFPI analog molecules in which less than about 12, 11, 10, 9, 8, 7, 6, 5, 4, 3, 2, 1, or 0.5% of the preparation consists of modified species.

Table 1 compares the purity of recombinant ala-TFPI produced using Process B and using the method of the invention. In addition, the expression system, fermentation control strategy, and refractile body isolation procedures described below result in a greater than five-fold increase in the amount of TFPI or TFPI analog produced compared with the previous production methods.

TABLE 1

| Characteristic | Process B 22 Lots | Process C 6 Lots |
|---|---|---|
| PT Activity, % control | 97-122 | 103-111 |
| purity by SDS PAGE (reduced), %[1] | >98% | >98 |
| purity by CEX HPLC, %[1] | >97 | >99 |
| purity by SEC HPLC, %[1] | >98 | >98 |
| purity by CN HPLC, %[1] | 75% | 90% |
| identity by ES-MS | 32,006 | 32,007 |
| norleucine, %[2] | <0.6% | <0.3% |
| N-terminal methionine, % | <2% | <2% |
| cysteine adduct, % | 1% | not detected |
| norvaline, %[3] | <0.2% | 2-3% |
| acetylation observed | Yes | No |
| carbamylation observed | Yes | Yes |
| methionine oxidation | Yes | Yes |

[1]Values expressed as % monomer (SDS PAGE) or main peak (HPLC).
[2]Expressed as % norleucine substitution per mole of methionine.
[3]Expressed as % norvaline substitution per mole of leucine.

Certain aspects of this procedure, such as the butyl HIC step, use of the DTPA chelator during cell harvesting, SP-Sepharose fast flow chromatography (particularly in the presence of $Mg^{++}$), and improved fermentation methods, are generally suitable for proteins other than TFPI or TFPI analogs.

A preferred embodiment of this purification method suitable for commercial scale production of TFPI or TFPI analogs is described below.

Expression of TFPI or TFPI Analogs

TFPI or TFPI Analog Coding Sequences

The wild-type amino acid sequence of TFPI is shown in SEQ ID NO:1. Any nucleotide sequence that encodes TFPI or TFPI analog as defined above can be used to encode the TFPI or TFPI analog to be expressed. A preferred coding sequence for ala-TFPI is shown in FIG. 15.

Production of TFPI or TFPI Analogs

Recombinant TFPI or TFPI analogs can be produced in any suitable host cell, such as a yeast or a mammalian host cell (e.g., CHO, HepG2, Chang liver, or SK hepatoma cells), as is well known in the art. See, e.g., U.S. Pat. Nos. 5,212,091, 6,103,500, and 6,323,326. Such recombinantly produced TFPI or TFPI analogs can be purified using methods of the invention as described below.

*E. coli* Host Cell

TFPI or TFPI analogs preferably are produced in an *E. coli* host cell. The preferred *E. coli* strain used for the production of TFPI is designated "MON210," which was deposited at the American Type Culture Collection (ATCC), P.O. Box 1549, Manassas, Va. 20108, USA on Oct. 8, 2003 (Accession No. PTA-5564) under the provisions of the Budapest Treaty. MON210 was generated from the wild type *E. coli* strain W3110 (Bachman, *Bacteriological Reviews* 36, 525-57, 1996) through a multi-step process involving the sequence W3110→MON 105 LBB358→MON210.

*E. coli* strain MON210 was generated from strain LBB358 via several steps. The recA56 mutation was introduced into strain LBB358 by P1 transduction (Csonka and Clark, J. Bacteriol. 143, 529-530, 1980) to reduce concatemerization of the production plasmid, resulting in strain LBB358recA⁻. The tetracycline resistance gene residing in Tn10 was then eliminated from LBB358recA⁻ by fusaric acid selection, producing strain LBB358recA⁻ T10. To select for spontaneously occurring altered rates of transcription elongation associated with rifampicin resistance, plasmid pMON26335rop⁺ was introduced into strain LBB358recA⁻ T10 to produce strain LBB358recA⁻ T10/pMON26335rop⁺. One rifampicin resistant strain that demonstrated increased levels of TFPI production was selected and then cured of plasmid pMON26335rop⁺. The resulting culture was designated MON210.

Plasmid

Plasmids to be used for expressing TFPI or TFPI analog in an *E. coli* host cell have the following genetic elements: a transcription promoter, a ribosome binding site, a TFPI or TFPI analog coding sequence, a transcription terminator, a replicon, an antibiotic resistance gene, and an enzyme that removes an N-terminal methionine. Particular preferred elements are shown in Table 2.

TABLE 2

| Genetic element | Preferred element |
| --- | --- |
| Transcription Promoter | reclac (U.S. Pat. No. 5,212,091), a synthetic promoter composed of the recA promoter with two base changes positioned upstream of the lac operator. Transcription of genes under the control of reclac promoter can be induced by the addition of IPTG to the culture. |

TABLE 2-continued

| Genetic element | Preferred element |
| --- | --- |
| Ribosome Binding Site | ribosome-binding site (RBS) from gene 10 of bacteriophage T7 (Olins et al., Gene 73, 227-35, 1988). |
| TFPI or TFPI analog coding sequence | see FIG. 15 |
| Transcription Terminator | canonical transcription terminator designated 2254 (AGCGTCGACA CTCCCGTTCT GGATAATGTT; SEQ ID NO: 42; see U.S. Ser. No. 09/044,369) |
| Replicon | origin of replication (ori) from pBR322 (Covarrubias et al., 1981) and rop, the copy number control gene from pBR322 (Polisky, Cell 55, 929-32, 1988). |
| Antibiotic Resistance Gene | streptomycin adenyltransferase gene, which encodes a protein that confers resistance to streptomycin and spectinomycin (Fling et al., Nucl. Acid. Res. 13, 7095, 1985). |
| N-terminal methionine-removing enzyme | gene encoding *E. coli* methionine aminopeptidase (MAP) (Ben-Bassat et al., J. Bacteriol. 169, 751-57, 1987) |

The plasmid "pMON37621" contains each of the preferred elements. The plasmid map of pMON37621 is shown in FIG. 1. The plasmid contains an optimized structural gene encoding ala-TFPI and the regulatory elements useful for high level production of proteins in *E. coli*. The pMON37621 plasmid was generated from pMON9197 without alteration of the ala-TFPI coding region.

Construction of pMON37621

Plasmid pMON37621 was constructed starting with plasmid pMON9197. pMON9197 contained the optimized gene encoding ala-TFPI as well as the gene 10 ribosome binding site (Olins et al., *Gene* 73, 227-35, 1988), the spectinomycin resistance gene (Fling et al., *Nucleic Acid Research* 13, 7095, 1985), the MAP gene (Ben-Bassat, *J. Bacteriol.* 169, 751-57, 1987), and the pBR327 origin of replication (Bolivar, *Gene* 2, 95-113, 1977). The reclac promoter (see U.S. Pat. No. 5,212, 091) was inserted into pMON9197 to replace the original tac promoter to yield plasmid pMON26335.

The reclac promoter (U.S. Pat. No. 5,212,091) is used to direct transcription of the ala-TFPI gene. The ribosome binding site is derived from gene 10 of bacteriophage T7. The transcription terminator is based on a canonical terminator sequence and is designated 2254. The origin of replication is from pBR322. To better control the copy number of the production plasmid, the rop gene from pBR322 (Polisky, *Cell* 55, 929-32, 1988) was inserted into pMON26335, which resulted in plasmid pMON26335rop⁺. The final step in the construction of pMON37621 was to substitute the transcription terminator designated 2254 (SEQ ID NO:42; see SEQ ID NO:3 of U.S. Ser. No. 09/044,369) for the bacteriophage P22 terminator. Plasmid pMON37621 also carries the aminoglycoside nucleotidyltransferase gene which confers on the host resistance to streptomycin and spectinomycin, and the *E. coli* methionine amino peptidase (MAP) gene to enhance removal of N-terminal methionine.

Preparation of the Production Strain MON210/pMON37621

The production strain MON210/pMON37621 is produced by transforming MON210 with pMON37621. Transformation can be accomplished by any means known in the art. Glycerol stocks of transformed MON210/pMON37621 can be prepared and used to establish Master and Working Cell Banks.

Preparation of the Master and Working Cell Bank

Master and Working Cell Banks are prepared from production strains as follows. To prepare a Master Cell Bank, a frozen vial of parent MON210/pMON37621 cells is thawed and grown in a shake flask for approximately 9 generations in the defined production seed medium with spectinomycin. Vials of cells with 10% glycerol can then be frozen and maintained at −70° C. Working Cell Banks can be prepared by thawing a master stock vial and growing the cells as described for the Master Cell Bank.

Fermentation Conditions

The manufacturing fermentation process comprises three stages: (1) Seed 1 shake flask, (2) Seed 2 fermentor, and (3) 10,000 L production fermentor. The composition of the media used during the fermentation process are listed in Table 3. KOH and $H_2SO_4$ are used to adjust the medium pH of the Seed 1 and Seed 2 media. $NH_4OH$ and $H_2SO_4$ are used to adjust pH of Fermentor medium. $NH_4OH$ also is used to control pH during the fermentation.

USP purified water is used throughout the fermentation process. The selective antibiotic spectinomycin is used during the preparation of the Working Cell Bank and is not used during the inoculum preparation or fermentation process.

TABLE 3

Fermentation Media Composition and Concentration

| Component | Seed 1 | Seed 2 | Fermentor[1] |
|---|---|---|---|
| | g/L | g/L | g/L |
| Dextrose | 4.0 | 4.0 | 41[2] |
| $(NH_4)_2SO_4$ | 2.5 | 2.5 | 2.5 |
| sodium polyphosphate | 6.5 | 6.5 | 4.0 |
| $K_2SO_4$ | 3.5 | 3.5 | 7.0 |
| $MgSO_4 \cdot 7H_2O$ | 1.23 | 1.23 | 1.63 |
| methionine | NA | NA | 2.0 |
| glycerol | NA | NA | 2.0 |
| | mg/L | mg/L | mg/L |
| $H_3BO_4$ | 0.5 | 0.5 | 0.5 |
| $CoCl_2 \cdot 6H_2O$ | 0.5 | 0.5 | 0.5 |
| $CuSO_4 \cdot 6H_2O$ | 0.13 | 0.13 | 0.13 |
| $FeCl_3 \cdot 6H_2O$ | 54.0 | 54.0 | 54.0 |
| $MnSO_4 \cdot H_2O$ | 11.0 | 11.0 | 11.0 |
| $Na_2MoO_4 \cdot 2H_2O$ | 0.5 | 0.5 | 0.5 |
| $NaSeO_3$ | 0.02 | 0.02 | 0.02 |
| $ZnSO_4 \cdot 7H_2O$ | 22.0 | 22.0 | 22.0 |
| $H_2SO_4$ (concentrated) | 0.01 mL/L | 0.01 mL/L | 0.01 mL/L |
| UCON (antifoam)[3] | NA | 0.3 mL/L | 0.55 mL/L |

[1]The initial volume in the fermentor is 6400 L.
[2]Actual glucose concentration at start is 34-42 g/L due to moisture content (<9%) of Cerelose.
[3]3.5 L of Ucon antifoam added at start. Additional antifoam (up to 12.5 L) may be added during the fermentation.

Seed 1—Shake Flask

The fermentation process begins by thawing a frozen vial of a Working Cell Bank. The contents of this vial (1 mL) is used to inoculate 0.5 L of seed 1 medium in a seed 1 shake flask. The flask is incubated at 37±2° C. and mixed at 200 RPM. The culture is grown for approximately 9 generations until a cell density of 0.9-1.7 OD is reached. The Seed 1 culture is then transferred to the Seed 2 fermentor.

Seed 2-30 L Fermentor

The 30 L of Seed 2 medium is inoculated with the 0.5 L contents of the seed 1 culture. The seed 2 medium is essentially the same as the Seed 1 medium, except for the addition of 0.1 mL/L Ucon antifoam. The Seed 2 fermentation preferably is carried out at a temperature of 37±2° C., with an air sparge of 6±2 LPM. The initial pH of the medium preferably is 7.2±0.2.

When the cells have grown approximately 6 generations to a density of 0.9-1.7 OD, the Seed 2 culture is transferred to the 10,000 L fermentor.

10,000 L Production Fermentor

The entire contents of the Seed 2 fermentor are transferred to the 10,000 L fermentor containing approximately 6,400 L of production medium. The production medium composition is shown in Table 3. The production fermentor is controlled for the following parameters. The temperature of the growth phase preferably is 37±2° C. The temperature set point is changed from 37° C. to 30° C. approximately 0.5 hours before the induction of TFPI or TFPI analog expression, and the temperature of the expression phase preferably is 30±2° C. pH is controlled by the addition of concentrated $NH_4OH$ and preferably is maintained at 6.9±0.2. A temporary pH spike to approximately pH 7.4±0.2 occurs when the initial supply of glucose is depleted and just prior to the start of the nutrient feed. Finally, dissolved oxygen (preferably 0.1-0.5 atm) is controlled by adjusting agitation rate, sparge rate, and the proportion of oxygen in the sparge gas.

Cell growth in the 10,000 L production fermentation begins as a simple batch culture, using the glucose of the starting medium. Glucose is depleted when the cell density reaches approximately 40 OD, as indicated by a pH increase to 7.4±0.2. At that time, a glucose/nutrient feed is started. The nutrient feed contains 550 g/L glucose, 18 g/L sodium polyphosphate, 6.65 g/L magnesium sulfate, and 4 g/L methionine. The nutrient feed rate is increased exponentially.

When the cell density reaches approximately 100 OD, the culture is induced to produce TFPI or TFPI analog by the addition of IPTG (e.g., 187+/−3 g of IPTG per fermentation, nominal volume=9500 L) and the glucose/nutrient feed rate is reduced to limit the glucose level during the expression phase. The temperature set point is changed so that the culture reaches 30±2° C. within one hour after induction. The culture is harvested approximately 12 hours after induction. The TFPI or TFPI analog concentration at harvest is approximately 5 g/L TFPI as determined by SDS-PAGE analysis.

Cell Harvest, Dissolution of Refractile Bodies, and Refolding of the Expressed TFPI Cell Harvest For cell harvest, the fermentation broth is adjusted to pH 5.5-6 and the delivery of oxygen and glucose are discontinued. Agitation is reduced, and the broth temperature is decreased to 5-10° C. The chelator DTPA is added to a final concentration of 1 mM. The DTPA addition is made using a stock solution that has been pH adjusted to 5.5-6.0 with citric acid. The harvest culture is fed to a BTUX-510 centrifuge operated at a flow rate to minimize loss of solids in the supernatant. Solids containing the harvested cells are continually pumped to a tank until the fermentor is empty. Purified water is added to the collected cells to a volume of ~10,000 liters, DTPA is added to a final concentration of 1 mM and processed through the BTUX-510 centrifuge as previously described. This wash step is repeated a total of two times.

Refractile Body (RB) Isolation

After the cell wash step, the recovery of refractile bodies (RB, also known as inclusion bodies) is started. Recovery comprises steps of repeated homogenization, centrifugation, and volume addition to the solids until they are essentially clean refractile bodies free of host cell debris. The homogenizer is operated at a constant pressure of approximately 9000 psig, and a BTUX-510 centrifuge or the equivalent is operated at a flow rate to minimize loss of solids in the supernatant.

Volume Reduction

During the first stage of the continuous centrifugation and volume addition process (diacentrifugation), the volume is reduced from approximately 5000 L to 2500 L. The supernatant from the centrifuge is discarded, and the solids are collected. The DTPA concentration for this and subsequent steps is 10 mM.

Batch Diacentrifugation 1

The next step in the RB isolation process is a batch diacentrifugation. During this step, the crude RB slurry prepared in the previous step is repeatedly homogenized (in a continuous mode) and centrifuged (in a batch mode) until the final RB slurry is largely free of contaminating cell material. Typically, three batch steps using a BTUX-510 centrifuge or the equivalent are used to achieve the desired RB purity. The centrifugation parameters for batch diacentrifugation are the same as those indicated for volume reduction.

Batch Diacentrifugation 2

At the end of the second batch diacentrifugation step, a sodium citrate buffer wash is used to remove undesired fermentation impurities such as nucleic acids and metals. At the end of this step, sodium citrate is added to a final concentration of 150 mM at a pH of approximately 5.5-6.0.

Batch Diacentrifugation 3

An SC-35 centrifuge or its equivalent is used for a third batch diacentrifugation step. Batch diacentrifugation 3 starts with an RB slurry volume of approximately 2500 L. The supernatant is discarded, and the solids are collected separately. During this step, the volume of collected solids is minimized so that the final volume is not greater than 500 L before host cell inactivation.

Host Cell Inactivation

The RB slurry collected in the previous step contains residual recombinant bacterial cells ($\sim 10^3$-$10^5$ cells/ml). These viable cells are inactivated before the RB slurry can be dispensed into containers. Residual *E. coli* cells are inactivated by contact with 1-octanol (0.2% v/w for a slurry that contains approximately 50% solids) for 30 minutes at 5-10° C.

RB Slurry Dispensing and Storage

After inactivation, the RB slurry ("RB intermediate") is dispensed into equal portions and frozen. For example, the inactivated RB slurry is conveniently frozen at <-20° C. in aliquots of 7.5 L each.

Dissolution and Refolding

The refolding reaction described below can be completed in one day, even at a commercial scale of 10,000 L. The amount of TFPI or TFPI analog in the refolding step is 20,000 g. The concentration of TFPI or TFPI analog is 2 g/L during the refolding reaction. The refolding chemistry includes cystine-coupled and copper-catalyzed oxidation to form correct disulfide bonds.

Thawed RB intermediate is transferred into a tank containing 6 M urea, 2 g/L polyphosphate, 50 mM Tris, 50 mM glycine, pH 10, homogenized using a shear mixer, and reduced by the addition of a stock DTT solution. The reduced, homogenized RB solution is transferred into a folding tank which, after transfer, contains approximately 3.5 M urea, 50 mM Tris, 50 mM glycine, 2 g/L polyphosphate, and 1 mM DTT, pH 10.2. Folding is initiated by the addition of 0.2 µM cupric chloride and 0.6 mM cystine. After approximately 24 hr, 10 µM cupric chloride is added. After approximately 1 hour, magnesium chloride is added to a final concentration of 50 mM, and the pH of the folded pool is adjusted to 5.5 using a 47.5% acetic acid solution. If desired, the adjusted folded pool can be held for approximately two days, which permits portions of the pool to be removed and processed in sublots through the next purification steps.

SP-Sepharose Fast Flow Chromatography

Cation exchange chromatography using SP-Sepharose FF resin is used for an initial capture step. The column load capacity is 40 g/L of total protein. The column is equilibrated with 20 mM sodium citrate, 3 M urea, pH 6. The adjusted folded pool is filtered through a depth filter and a 0.45 µM filter and applied to the column. After loading, the column is washed with equilibration buffer followed by an intermediate salt wash (~150 mM sodium citrate). The protein is eluted using approximately 190 mM sodium citrate. An increase in the $A_{280}$ trace during the elution step initiates pooling. The pooling continues for approximately 3 column volumes or until the $A_{280}$ trace returns to baseline. After elution, the column is regenerated with a 0.5 N NaOH solution and re-equilibrated to process additional sublots or washed with 0.1 N NaOH for storage. The absorbance of the pool is measured at 278 nm to determine the protein concentration and column recovery.

First Concentration/Diafiltration

The SP pool is adjusted to pH 4.5-5.0 using 6N acetic acid, concentrated to 12-14 g/L, and diafiltered using a 10 kDa membrane with 8 volumes of diafiltration buffer containing 20 mM acetic acid, 15 mM NaCl, 3 M urea, pH 4.25. The diafiltered solution is drained from the system, and the concentration is determined at 278 nm (typical range 10-12 g/L) to determine step recovery. The diafiltered pool is then filtered through a 0.2 µm filter into a sterile bag and can be maintained at 2-8° C. for at least 3 months until the Q-Sepharose HP chromatography step is carried out.

Q-Sepharose HP Chromatography

The concentrated, diafiltered SP pool is adjusted to a final concentration of approximately 4 M urea, 20 mM NaCl, 20 mM Tris, pH 7.6-8.5 and loaded unto a Q-Sepharose HP column. column is equilibrated with buffer containing 4 M urea, 20 mM sodium chloride, 20 mM Tris, pH 8. After loading, the column is washed with equilibration buffer, followed by equilibration buffer containing 50 mM sodium chloride. TFPI is eluted using a 10 CV gradient of 50-80 mM sodium chloride in buffer. Fractions containing TFPI can be pooled based on fraction analysis by SDS PAGE and HPLC analysis to verify inclusion of the appropriate fractions.

After the TFPI or TFPI analog has eluted, the column is washed with 150 mM sodium chloride buffer, then regenerated with a solution containing 0.5 N NaOH and 1 M NaCl. Sublots can be processed after equilibrating the column as described above. Columns can be stored in 0.1 N NaOH. The absorbance of the pool at 278 nm is used to determine the protein concentration and column recovery.

Butyl HIC Chromatography

The pool from the Q-Sepharose HP chromatography step is adjusted to 2.5M NaCl, 2 M urea, 100 mM sodium citrate, pH 6 and loaded to a Butyl 650 M column. After loading, the column is washed with 3 CV of 1.7 M NaCl, 2 M urea, 100 mM sodium citrate, pH 6. Product is eluted with a 10 CV gradient from 1.7 M NaCl to 0 M NaCl in a buffer containing 2 M urea and 100 mM sodium citrate, pH 6. The column is operated in a "bind and elute" mode. Fractions are collected and analyzed by HPLC analysis to verify inclusion of the appropriate fractions in the pool. After elution, the column is washed with buffer containing no salt. Column regeneration is performed using 0.5 N NaOH. The column can either be re-equilibrated if additional sublots are to be processed or washed in 0.1 N NaOH for storage. The absorbance of the pool is measured at 278 nm to determine the protein concentration and column recovery.

SP-Sepharose HP Chromatography

A high performance cation exchange chromatography step is used as a polishing step to remove carbamylated TFPI or misfolded TFPI species. The butyl pool is diluted approximately 5× with a buffer containing 3.9M urea at pH 5.5 to a conductivity of approximately 15.6 at 2-8' C. The adjusted butyl pool is loaded to a SP-Sepharose HP column equilibrated with 20 mM sodium citrate, 3 M urea, pH 5.5. After loading, the column is washed with 1.5 CV of buffer containing 400 mM NaCl, 3M urea, 20 mM sodium citrate, pH 5.5. Protein is eluted using a 17 CV gradient of 400-650 mM NaCl in 3 M urea, 20 mM sodium citrate, pH 5.5.

Fractions are collected when an increase in the UV absorbance occurs. Carbamylated and misfolded material elutes on the ascending portion of the elution peak. After the protein has eluted, the column is regenerated with 1 M sodium chloride in 3 M urea, 20 mM sodium citrate, pH 5.5 followed by a solution containing 0.5 N NaOH. The column is then washed and stored in 0.1 N NaOH. The fractions are analyzed by CEX HPLC and SDS PAGE to determine purity.

Fractions that contain greater than 95% of their material as the main TFPI- or TFPI analog-containing peak can be combined to produce an SP-Sepharose HP pool. Preferably, the fractions contain greater than 91, 92, 93, 94, 95, 96, 97, 98, or 99% TFPI or TFPI analog. An additional in-process assay (protein concentration by absorbance at 278 nm) can be performed to determine the yield of this purification step.

Second Concentration/Diafiltration

The second (final) concentration/diafiltration step also uses a 10 kDa membrane. The SP-Sepharose HP pool is concentrated to approximately 12 g/L protein and diafiltered with 8 volumes of a buffer containing 300 mM L-arginine and 20 mM sodium citrate, pH 5.5. The diafiltered solution is recovered, and the protein concentration is measured at 278 nm to determine the yield of this step. Typically, the final protein concentration is approximately 10 mg/mL after flushing the unit.

The drug substance can be filtered through a 0.2 μm sterile filter and stored, preferably at <60° C. for at least 24 months.

Drug Formulation

TFPI or TFPI analog produced according to the method described above is suitable for therapeutic administration. In a preferred embodiment, a pharmaceutical formulation contains 0.15 mg ala-TFPI/mL in 20 mM sodium citrate, 300 mM L-arginine, and 5 mM L-methionine pH 5.5. See also the formulations disclosed in Ser. Nos. 60/438,519, 60/494,577, 60/509,260, 60/512,090, 60/438,524, 60/494,547, 60/509, 276, and 60/512,092.

All patents, patent applications, and references cited in this disclosure are expressly incorporated herein by reference in their entireties. The above disclosure generally describes the present invention. The specific examples in this disclosure are provided for purposes of illustration only and are not intended to limit the scope of the invention.

Example 1

Amino Acid Analysis and Determination of Amino Acid Composition

Three replicate aliquots of each lot of recombinant ala-TFPI (rTFPI) drug substance, each containing approximately 600 picomoles (~20 μg) of protein, were hydrolyzed in vacuo at 110° C. for 22 hours in 100 μL of constant boiling HCl containing 1% phenol. Samples of the preparations obtained after reduction and carboxymethylation of cysteine residues were treated in the same way. The free amino acids were separated by ion-exchange chromatography using a Beckman Model 6300 amino acid analyzer, operated with the manufacturer's program for analysis of protein hydrolysates with sodium buffers. After post column derivatization with ninhydrin, the amino acids were quantified at 570 nm for primary amines or 440 nm for proline. Calibration of the system was achieved through the use of a Beckman amino acid standard mixture. All samples were "spiked" with norleucine (Nle) as an internal standard.

Quantitation of Norvaline and Homocitrulline by an Ion-Exchange Method

Norvaline and homocitrulline were quantified by use of a Beckman 6300 amino acid analyzer, employing sodium buffer elution protocol modifications to facilitate the resolution of norvaline and homocitrulline from valine. Two buffers were employed in the resolution protocol: Beckman buffer Na—F, which was titrated to pH 3.75 with 6 N HCl, and Beckman buffer Na-D, which was not altered in pH or concentration. The program employed Na—F as the first eluent and the column temperature was 25° C. Flow was maintained for 40 minutes with a column temperature increase to 75° C. after 30 minutes of isocratic elution. At forty minutes post-injection, Na-D was employed for another 15 minutes of isocratic elution. This program yielded baseline separation of norvaline, valine and homocitrulline and maintained separation of the basic amino acids.

Protein hydrolysis was performed as described above. Calibration of the system was achieved through the use of a Beckman amino acid standard mixture. Norvaline was quantified in relation to a gravimetric standard obtained from Sigma. Homocitrulline was purchased from ICN Biomedicals of Ohio and a gravimetric standard was prepared for system calibration (see below). Samples were "overloaded" on the column and histidine, an amino acid of low incidence in rTFPI (three moles per mole of protein) was quantified to define the number of moles of rTFPI present in the sample for the calculation of incorporation level based on the leucine (norvaline) and lysine (homocitrulline) content of the protein.

Quantitation of Homocitrulline by an RP-HPLC Method

Homocitrulline was quantified by use of the Waters AccQ•Tag amino acid analysis method. Proteins were hydrolyzed in 6 N HCl containing 1% phenol for 22-24 hours at 110° C.; the free amino acids were derivatized with 6-aminoquinolyl-N-hydroxysuccinimidyl carbamate (AQC) at high pH in the presence of borate buffer. Both primary and secondary amines were thus converted to stable fluorescent derivatives, which were resolved by reversed-phase (RP) high performance liquid chromatography (HPLC). Control experiments indicate that 25% of the amino acid analogue is converted to lysine during acid hydrolysis. A correction factor was applied to the data to account for this reaction. As in the case of the norvaline quantitation, histidine was quantified to define the number of moles of rTFPI present in the sample for calculation of the modification level based on the lysine content of the protein.

N-Terminal Amino Acid Sequence Analysis by Edman Degradation

N-terminal sequence analysis of lots of bulk rTFPI product was performed by Edman degradation. During each cycle of the sequence analysis, the protein sample was exposed to a volatile base, coupling reagent (phenylisothiocyanate), and anhydrous acid to release the phenylthiohydantoin (PTH) derivative of the N-terminal amino acid residue, which produces a protein with one less residue at the N-terminus. The free PTH-amino acid derivatives were identified by reversed-phase HPLC.

Sequence analysis was accomplished with a Perkin-Elmer Biosystems (PEB) Procise 494 protein sequencer. A 1.5-μL aliquot of each lot of rTFPI at a 1:10 dilution, containing approximately 50 picomoles of protein, was diluted into water and loaded directly onto a polyvinylidene difluoride (PVDF) membrane, using the ProSorb system (PEB) to remove excipients. Programs, protocols, and reagents were provided by the instrument manufacturer.

Reduction and Carboxymethylation (RCM) of Sulfhydryl Groups

Samples were transferred to 1.5 mL microfuge tubes with o-ring caps and dried by vacuum centrifugation on a Savant Speed-Vac concentrator. Each sample was dissolved in 250 μL of reduction and carboxymethylation (RCM) buffer containing 0.2 M tris(hydroxymethyl)aminomethane (Tris), 6.0 M guanidine hydrochloride, 0.003 M ethylenediaminetetraacetic acid, pH 8.5, and 15 μL of 1.0 M DTT were added to reduce disulfide bonds. The tubes were flushed with argon gas and capped tightly to exclude oxygen. The samples were incubated at 60° C. for one hour in a Thermomixer. Fresh sodium iodoacetate (IAA) solution was prepared (0.25 g/mL, 1.2 M) in a four-fold dilute aliquot of the RCM buffer, and 26 μL of the IAA solution were added to each rTFPI sample. The tubes were flushed with argon gas and capped tightly to exclude oxygen. The carboxymethylation reaction was carried out at room temperature in the dark for 30 minutes. The reaction mixture was desalted on NAP-5 columns. Aliquots of the final product of each reaction were quantitated by amino acid analysis for protein concentration.

Protein Desalting

In some cases the protein was desalted prior to analysis or enzymatic digestion. A Vydac C4 guard cartridge (4.6×20 mm; 5 micron particle size) was employed to separate protein from excipients, such as urea, arginine, or guanidine hydrochloride, which might interfere with analyses of a number of types. Samples of one to two milligrams of protein were injected onto the column equilibrated in 0.1% trifluoroacetic acid (TFA) in water (buffer A). The protein was eluted from the cartridge at a flow rate of 1.0 mL per minute with the following gradient (endpoints) with buffer B (80% acetonitrile:0.1% TFA in water): 0 minutes=0% B; 5 minutes=0% B; 15 minutes=90% B; 18 minutes=90% B; 20 minutes=0% B. The eluate was monitored at a wavelength of 220 nm at a range of 2.0 absorbance units full scale (AUFS). All excipients eluted in the first 5 minutes of elution. The rTFPI peak was collected manually, and volatile solvents were removed by vacuum concentration.

Endoproteinase Digestion; Generation of Non-Reduced Peptide Fragments

Ten microliters of rTFPI from lot MAECM014 was digested in 150 μL 100 mM Tris-HCl, pH 6.8, with 0.8 μg of Asp-N (Boehringer Mannheim). Ten microliters of rTFPI was digested in 150 μL 100 mM Tris-HCl, pH 6.8, with 1.8 mM zinc acetate. The Asp-N digestion was carried out at 37° C. for 18 hours. Digestion was terminated by the addition of 150 μL of 8 M guanidine hydrochloride solution, and samples were stored at −80° C. before analysis.

Trypsin Digestion; Generation of RCM Peptide Fragments

Aliquots of 80 μL each of rTFPI after RCM were transferred to 1.5 mL microfuge tubes for trypsin digestion. Promega porcine trypsin (20 μg) was dissolved in 0.05 M acetic acid (40 μL) and 1.6 μL of the trypsin solution (0.5 mg/mL) were added to each rTFPI sample. The final rTFPI concentration was 0.4 mg/mL in 35 mM Tris (pH 8) with a trypsin/TFPI ratio of 1/50 (w/w). The trypsin digestion was carried out at 37° C. for 18 hours. Digestion was terminated by freezing the samples, which were stored at −80° C. before analysis.

Glu-C Endoproteinase Sub-Digestion of Non-Reduced Asp-N +42/43 Da Peptide

Peptides isolated from HPLC were dried by vacuum centrifugation. Each sample was re-dissolved in 50 microliters of 30 mM ammonium acetate solution, at pH 4. Approximately half a microgram of endoproteinase Glu-C was added to each peptide sample. The digestion was allowed to proceed at room temperature overnight. The pH was adjusted to 8 by addition of 1 M Tris-HCl buffer at pH 8; it was then reduced with 0.5 μL of 1 M DTT for 30 minutes at 60° C. prior to analysis by LC-MS.

Arg-C Endoproteinase Sub-Digestion of Glu-C Peptides under Reducing Conditions

Peptides isolated by HPLC were dried by vacuum centrifugation. Digestion buffer was 150 mM Tris-HCl and 15 mM calcium chloride at pH 7.5. Enzyme activation buffer was made immediately before the digestion by adding 300 μL of water to the lyophilized material supplied in the kit (Boehringer Mannheim). Endoproteinase Arg-C enzyme solution was prepared by reconstitution of 5 μg lyophilized enzyme in 250 μL of water. Each sample was re-dissolved in 7 μL of digestion buffer, in addition to 3 μL of activation buffer and 1 μL of Arg-C enzyme solution. The digestion was allowed to proceed at 37° C. for 2 hours, prior to analysis by MALDI-TOF-MS.

Fast Gradient LC-MS; Measurement of Intact rTFPI Molecular Mass

Measurements of the molecular masses of intact rTFPI were performed using a Michrom Ultrafast Microprotein Analyzer (UMA) HPLC system interfaced to a Perkin-Elmer Sciex API 100 mass spectrometer (LC-MS). Samples (approximately 2 μg each) were injected onto a reversed-phase (RP) column (Zorbax Cyano, 1 mm×150 mm). Solvent A was 5% acetonitrile in water and 0.1% TFA, and solvent B was acetonitrile containing 0.09% TFA. Gradient elution was performed from 5% B to 95% B in 10 minutes at a flow rate of 50 μL/minute. The effluent was split at a ratio of 10:1 after the flow cell, with approximately 5 μL/minute directed into the electrospray ion source of the API 100 mass spectrometer. The ion spray voltage was set at 4.5 kV, and the orifice voltage was at 50 volts. The instrument was calibrated with ions generated from a polypropylene glycol (PPG) mixture supplied by the manufacturer.

During electrospray ionization, peptides or proteins are introduced into the mass spectrometer ion source at low pH. The basic sites in proteins and peptides (nitrogen atoms in the side chains of arginine, lysine and histidine residues, as well as the alpha-amino groups of the N-terminal residues) are protonated to varying degrees, which results in molecular ions of multiple charge states (e.g., $[M+H]^+$ and $[M+2H]^{2+}$), depending on the number of sites accessible for protonation. The detector records the mass-to-charge ratio (m/z) of the molecular ions from which the molecular mass can be calculated by a software algorithm. The mass accuracy of the measurements in this mode was 0.01% of the molecular mass of rTFPI (+/−3 Da).

Slow Gradient LC-MS; Measurement of Intact Molecular Mass of Individual rTFPI Components Five μg samples were analyzed by a reversed-phase (RP) column (Zorbax Cyano, 1 mm×150 mm). Solvent A was 5% acetonitrile in water and 0.1% trifluoroacetic acid (TFA), and solvent B was acetonitrile containing 0.09% TFA. Gradient elution was performed from 27% B to 32% B in 30 minutes at a flow rate of 50 μL/minute. The electrospray ionization mass spectrometer operation was performed as described above.

LC-MS of Non-Reduced Peptide Digests; Mass Measurement of Peptides

Ten microliter aliquots of the Asp-N digest were subjected to LC-MS analysis using a Michrom Ultrafast Microprotein Analyzer (UMA) HPLC system interfaced to a Perkin-Elmer Sciex API 100 mass spectrometer. Samples were injected onto a reversed-phase (RP) column for LC-MS using a Vydac C18, Reliasisl C18 or Zorbax Cyano column (1 mm×150 mm, 5 μm particle size and 300 Angstrom pore size). Solvent A was 5% acetonitrile in water with 0.1% trifluoroacetic acid (TFA), and solvent B was acetonitrile containing 0.09% TFA. Gradient elution was performed from 5 to 25% solvent B in 25 minutes and from 25% to 36% B in 30 minutes at a flow rate of 50 μL/minute. For trypsin digest, gradient elution was performed from 5% to 45% B in 80 minutes. The effluent was split at a ratio of 10:1 after the flow cell, with approximately 5 μL/minute directed into the electrospray ion source of the API 100 mass spectrometer. The ion spray voltage was set at 4.5 kV, and the orifice voltage was set at 50 volts. The instrument was calibrated with ions generated from a polypropylene glycol (PPG) mixture supplied by the manufacturer. The mass accuracy of molecular mass measurement by LC-MS was ±1 Da in the mass range of the rTFPI peptides.

MALDI-TOF MS; Accurate Mass Measurement of Peptides

MALDI-TOF mass spectra were acquired on a Bruker Reflex instrument equipped with a nitrogen laser (337 nanometers, 4 nanosecond pulse) and a delayed-extraction ion source. Samples for analysis were prepared by adding 1 μL to 1 μL of a saturated solution of alpha-cyano-4-hydroxycinnamic acid. The mixture was vortexed, and 1 μL was loaded onto the sample target. The air-dried sample/matrix mixture was introduced into the mass spectrometer by means of a vacuum lock. Spectra were recorded using an accelerating voltage of 20 kV and a reflectron voltage of 21.5 kV. For delayed-ion extraction, a 6 kV potential difference was applied between the sample probe and the extraction lens. Spectra were calibrated using a mixture of known peptides as an external calibration standard. The mass accuracy of molecular weight measurement by delayed extraction MALDI-TOF MS was ±0.5 Da using external calibration. In some cases spectra were calibrated using a known peptide in the sample. In this case the mass accuracy was ±0.02 Da at peptide masses of 2,000 Da or less (approximately 10 ppm).

NanoES MS and MS/MS; Identification of Peptide Modifications

Experiments were performed on a Perkin Elmer Sciex API-III triple quadrupole instrument equipped with a custom ion source (Wilm and Mann, EMBL, Heidelberg, Germany) and an updated high pressure collision cell. Approximately 1 μL of each sample was loaded into a gold-coated glass capillary needle and positioned in the mass spectrometer source with the aid of a stereo microscope. Mass spectra were recorded over the m/z range appropriate for the peptide under analysis, at 8 seconds/scan, using a step size of 0.1 Da. The instrument was calibrated with ions generated from a PPG mixture, supplied by the manufacturer.

Low energy collision-induced dissociation tandem mass spectra (CID-MS/MS) were acquired in the positive ion mode. Samples were introduced into the MS ion source as above. The second quadrupole was scanned over an m/z range of 50 to the parent ion m/z at 5-10 seconds/scan using a step size of 1 Da. The orifice potential was set at 40 volts, and the collision energy was approximately 60 electron volts. In tandem mass spectrometry, the molecular ion of interest, in a mixture of peptides, can be selectively introduced into the collision cell. Bombardment with an inert gas in the collision cell results in fragmentation of the peptide at the amide bonds. The fragments produced in the collision cell are analyzed by the second mass spectrometer. The tandem mass spectrum provides amino acid sequence information including the position of any covalent modifications.

Mass Assignments; Monoisotopic Masses

In the analysis of peptides by delayed ion extraction MALDI-TOF MS, the mass spectrum of a pure peptide will possess a number of peaks at high resolution, with each peak corresponding to the peptide with a specific isotope abundance. The monoisotopic mass of a compound is the sum of the masses of the lightest stable isotopes for the elements in the compound (e.g., carbon is 12.0000 Da; 98.90% abundance). Because there is a stable isotope of carbon with a mass of 13.0034 Da at a natural abundance of 1.10%, any organic compound with 100 carbon atoms or more will possess one or more carbon-13 isomers. The major ions in the mass spectrum of a peptide result from the simple acquisition of one proton; use of the calibration software yields a monoisotopic mass for the components of the spectrum, using assignments for the carbon-12 isomers. The monoisotopic molecular mass is obtained by MS analysis when the isotopic peaks can be resolved at the isomer level, e.g., at lower mass values or through the use of a high-resolution instrument.

Mass Assignments; Average Values

The average molecular mass of a peptide or protein is the sum of the chemical average masses of each element in the molecule. The average chemical mass of an element is the sum of the masses of all of the stable isotopes (e.g., carbon is 12.0111 Da), weighted for relative abundance. The average molecular mass is obtained by MS analysis when the monoisotopic peaks cannot be resolved (e.g., at high mass values).

Example 2

Drug Substance Release Testing of Reference Materials

Figure 2:
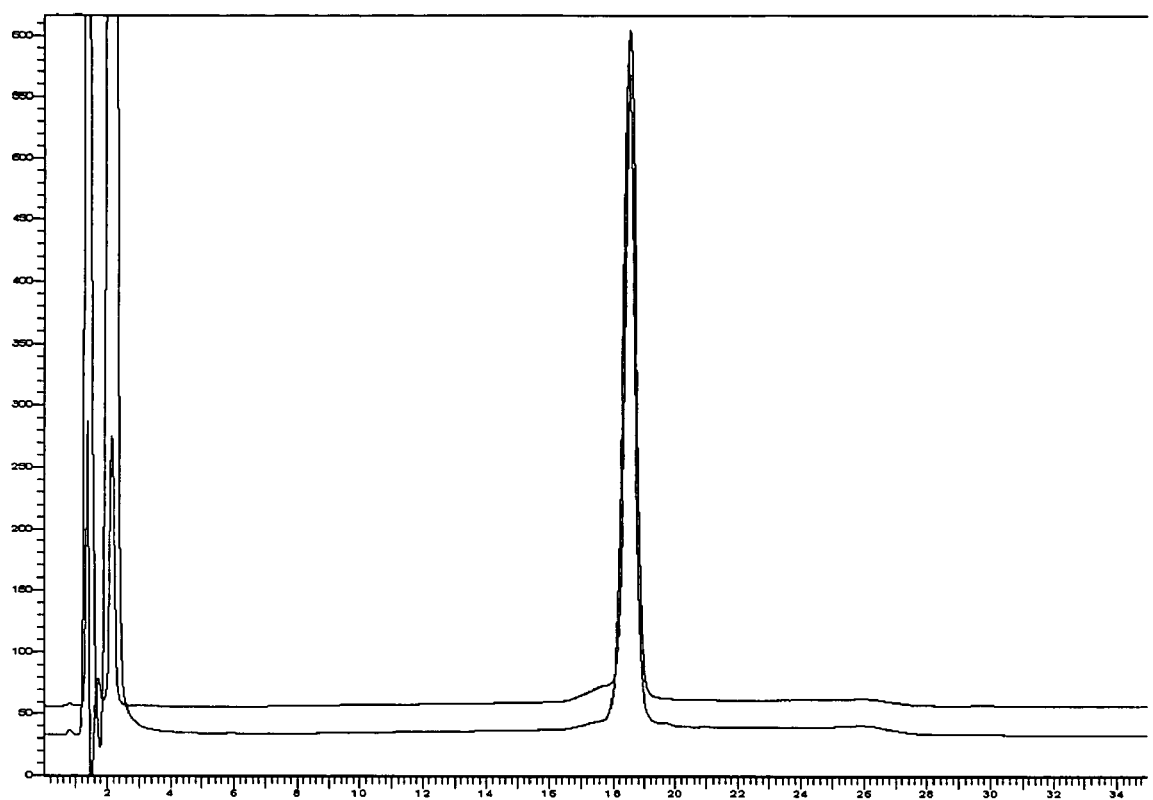
FIG. 2. Comparison of two lots of recombinant ala-TFPI (rTFPI) preparations by cation exchange chromatography (CEX HPLC). Ten μg of sample were applied to a Pharmacia Mono S 5/5 cation exchange column and separated using a linear 0.2-0.85 M ammonium chloride gradient in 30% acetonitrile and 0.02 M sodium acetate. The column eluent was monitored by UV absorbance at 214 nm. The top chromatogram is from lot PB5806 (prepared according to Process C, defined below); the lower chromatogram is from lot MAECM014 (prepared according to methods described in Process B, defined below).
Figure 3:
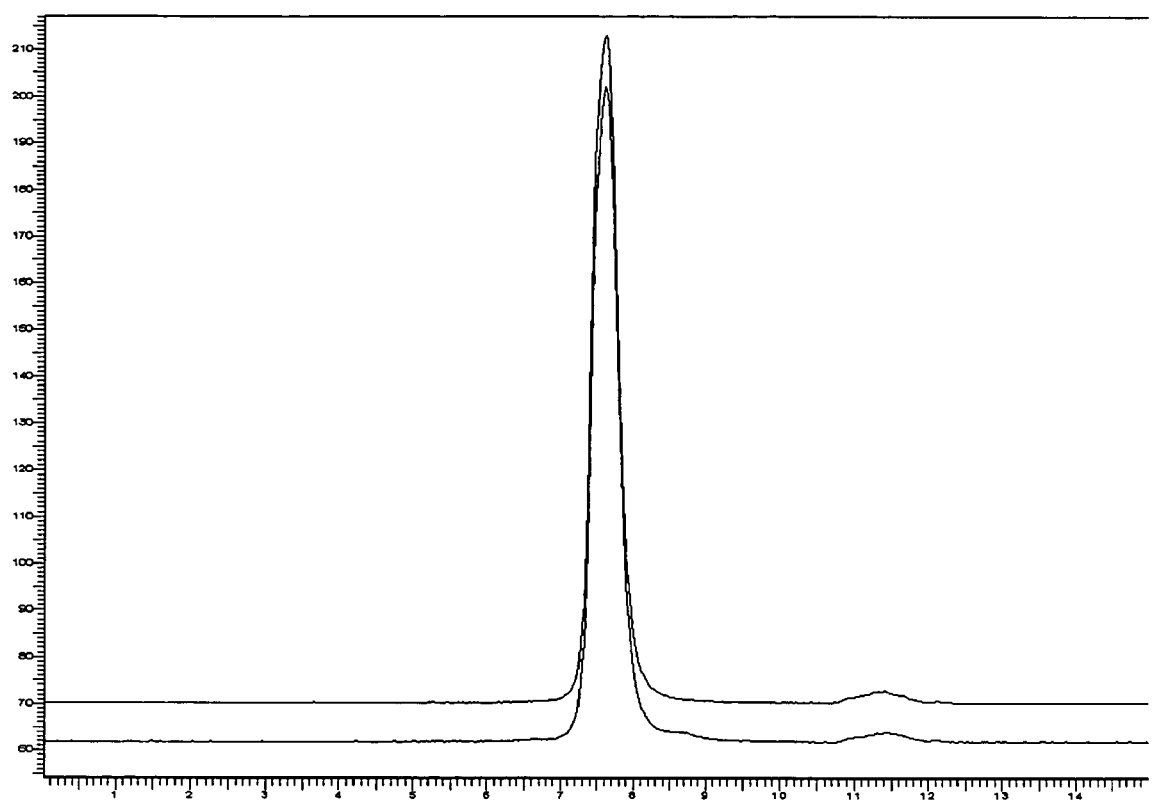
FIG. 3. Comparison of two lots of rTFPI preparations by size exclusion chromatography (SEC HPLC). Ten μg of sample were applied to a BioRad Bio-Sil SEC 250-5 column and separated using an isocratic eluent containing 40% acetonitrile and 0.75% trifluoroacetic acid. The column eluent was monitored by UV absorbance at 280 nm. The upper chromatogram is from lot PB5806 (prepared according to Process C); the lower chromatogram is from lot NA0182 (prepared according to Process B).
Figure 4:
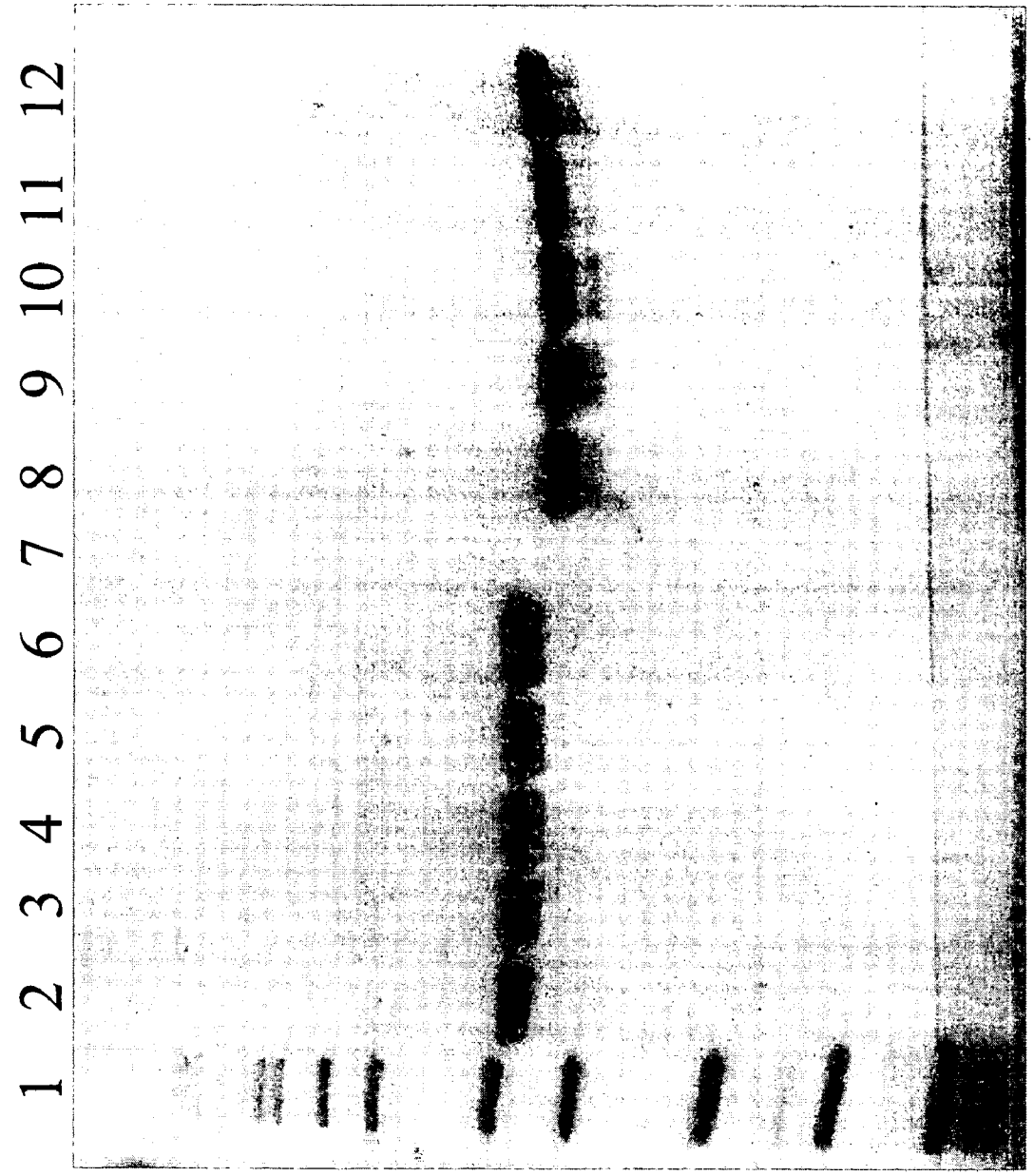
FIG. 4. SDS PAGE of reduced and non-reduced rTFPI samples. Samples were analyzed using a 14% Tris-glycine gel and visualized using Coomassie staining. Approximately 3 μg of sample was applied to each lane. Electrophoresis of samples in lanes 1-6 was performed under reducing conditions; that of samples in lanes 8-12 was performed under non-reducing conditions. The samples were loaded as follows: lane 1, molecular weight standards; lanes 2 and 8, sample of lot NA0182 (prepared according to Process B, defined below); lanes 3 and 9, samples of lot MAECM014 (prepared according to Process B); and lanes 4 and 10, 5 and 11, and 6 and 12, samples of lots PB5666, PB5806, and PB6096, respectively (prepared according to Process C).
Figure 5:
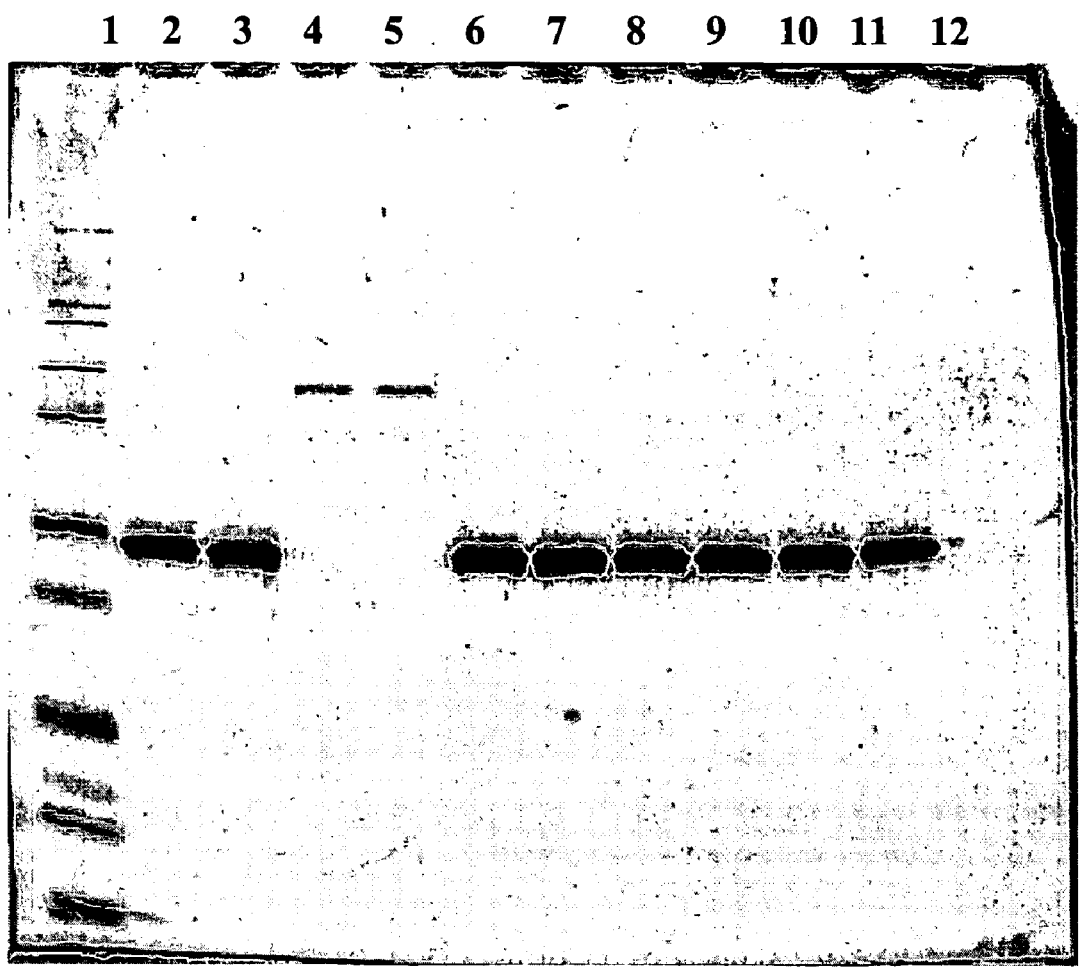
FIG. 5. SDS PAGE using silver stain analysis. Samples were reduced with DTT and analyzed using a 14% Tris-glycine gel. Approximately 0.5 mg of rTFPI sample (prepared according to Process C) was applied to each lane. The samples included molecular weight standards (lane 1), sample from reference lot PB5806, prepared according to Process C) (lanes 2 and 3), 2 ng bovine serum albumin (66 KDa) and 0.25 ng carbonic anhydrase (31 KDa) (lane 4), 5 ng bovine serum albumin (66 KDa) and 0.25 ng carbonic anhydrase (31 KDa) (lane 5), and triplicate samples from lot PB6636 (lanes 6-8) and from lot PB6770 (lanes 9-11) (prepared according to Process C). Lane 12 is blank.
Figure 11:
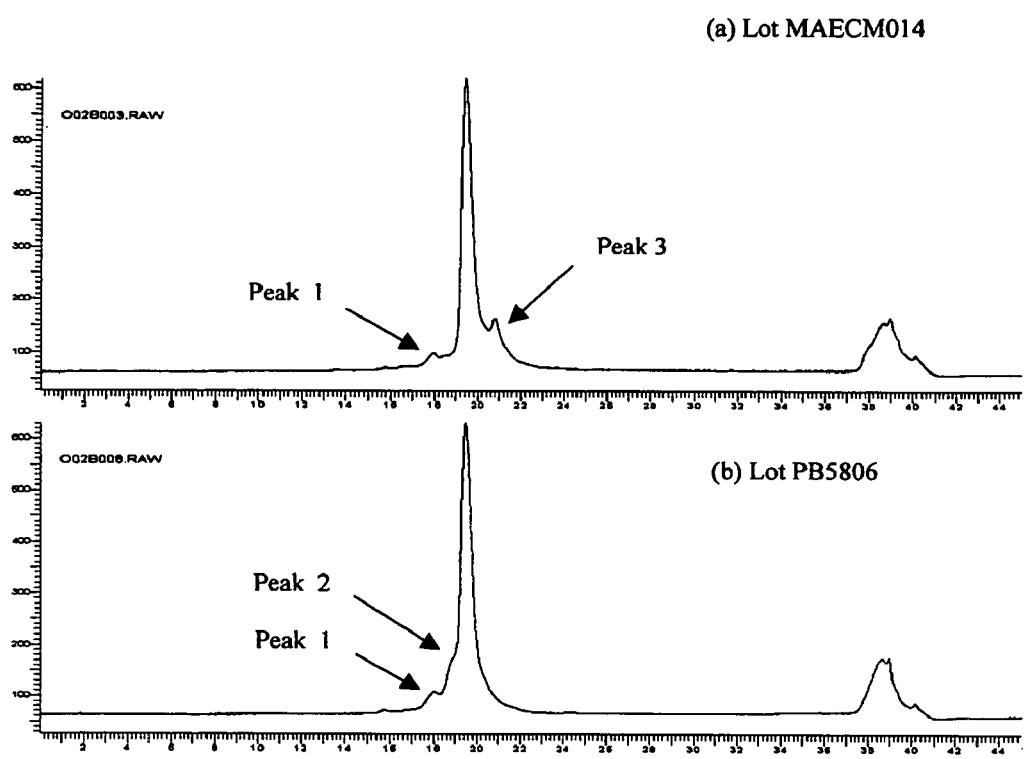
FIG. 11. CN HPLC of rTFPI drug substance.

Comparison of the purity of rTFPI prepared according to Process B and those prepared according to Process C as assessed by CEX HPLC and SEC HPLC are shown in FIGS. 2 and 3, respectively. SDS PAGE analysis using Coomassie staining or silver staining is shown in FIGS. 4 and 5, respectively. These data show the comparability between the Process B and Process C drug substances by these release assays. Comparison of the same materials by CN HPLC is shown in FIG. 11.

Physical Characterization of the Major Components Amino Acid Composition

The amino acid composition determined for rTFPI prepared according to Process C is shown in Table 4. Amino acid recoveries were normalized to residues per molecule. The theoretical values were predicted from the nucleotide sequence of the rTFPI gene. Aspartic acid and asparagine residues were recovered as aspartic acid (Asx); glutamic acid and glutamine residues were recovered as glutamic acid (Glx—all amide linkages are hydrolyzed by the acid treatment). Values for cysteine were determined by quantitation of the carboxymethyl-cysteine in the RCM protein preparations. Tryptophan was not determined (ND) because it is destroyed under the standard hydrolysis conditions. Isoleucine recoveries were low because bonds formed by this residue are only partially hydrolyzed in 22-24 hours. The cysteine values indicate full reactivity with the iodoacetic acid reagent, within the error of the method. The amino acid composition of the protein in the two reference lots is consistent with the predicted sequence of the protein.

TABLE 4

Amino Acid Compositions of rTFPI Preparations

| Amino Acid | Theory | Process B reference | Process C reference |
|---|---|---|---|
| Asx | 34 | 34.2 | 34.5 |
| Thr | 16 | 15.1 | 15.3 |
| Ser | 11 | 10.6 | 10.1 |
| Glx | 37 | 36.5 | 35.8 |
| Pro | 11 | 11.1 | 11.7 |
| Gly | 21 | 22.0 | 21.2 |
| Ala | 10 | 9.8 | 10.0 |
| Val | 6 | 6.4 | 6.5 |
| Met | 5 | 4.7 | 5.2 |
| Ile | 16 | 14.0 | 14.1 |
| Leu | 15 | 15.6 | 15.3 |
| Tyr | 10 | 10.0 | 10.0 |
| Phe | 21 | 20.8 | 21.2 |
| His | 3 | 3.1 | 3.0 |
| Lys | 25 | 24.8 | 25.1 |
| Arg | 17 | 16.9 | 19.5 |
| Cys | 18 | 17.4 | 17.2 |

Samples were reduced and carboxymethlyated.
Results expressed as moles of amino acid residue per mole of protein.
No Trp Determination
Asx = Asp + Asn; Glx = Glu + Gln N-terminus The results of N-terminal sequence analysis by Edman degradation are presented in Table 5. The yields shown are gross recoveries of the corresponding PTH-amino acid derivatives in each cycle of degradation. The identities were deduced from the relative recoveries in each cycle: the greatest increase in the case of non-repeating residues; a sustained high yield (without large increases of other derivatives) in the case of repeating residues. The differences in cycle yield reflect a disparity in the recovery of the protein from the two lots on the PVDF membrane during sample deposition. Each lot yielded equivalent results: a predominant fifteen-residue sequence that was in exact agreement with that predicted from the nucleotide sequence of the rTFPI gene.

TABLE 5

Sequence Analysis of Reference Lots

| | | Raw Cycle Yield* | |
|---|---|---|---|
| Cycle | Residue | MAECM014 | BP5806 |
| 1 | Ala | 28 | 17 |
| 2 | Asp | 16 | 10 |
| 3 | Ser | 10 | 5 |
| 4 | Glu | 11 | 5 |
| 5 | Glu | 17 | 7 |
| 6 | Asp | 9 | 3 |
| 7 | Glu | 12 | 7 |
| 8 | Glu | 12 | 7 |
| 9 | His | 4 | 1 |
| 10 | Thr | 5 | 2 |
| 11 | Ile | 5 | 2 |
| 12 | Ile | 9 | 5 |
| 13 | Thr | 6 | 4 |
| 14 | Asp | 4 | 2 |
| 15 | Thr | 7 | 4 |

*Cycle yield in picomoles of PTH-amino acid

Molecular Mass

Figure 6:
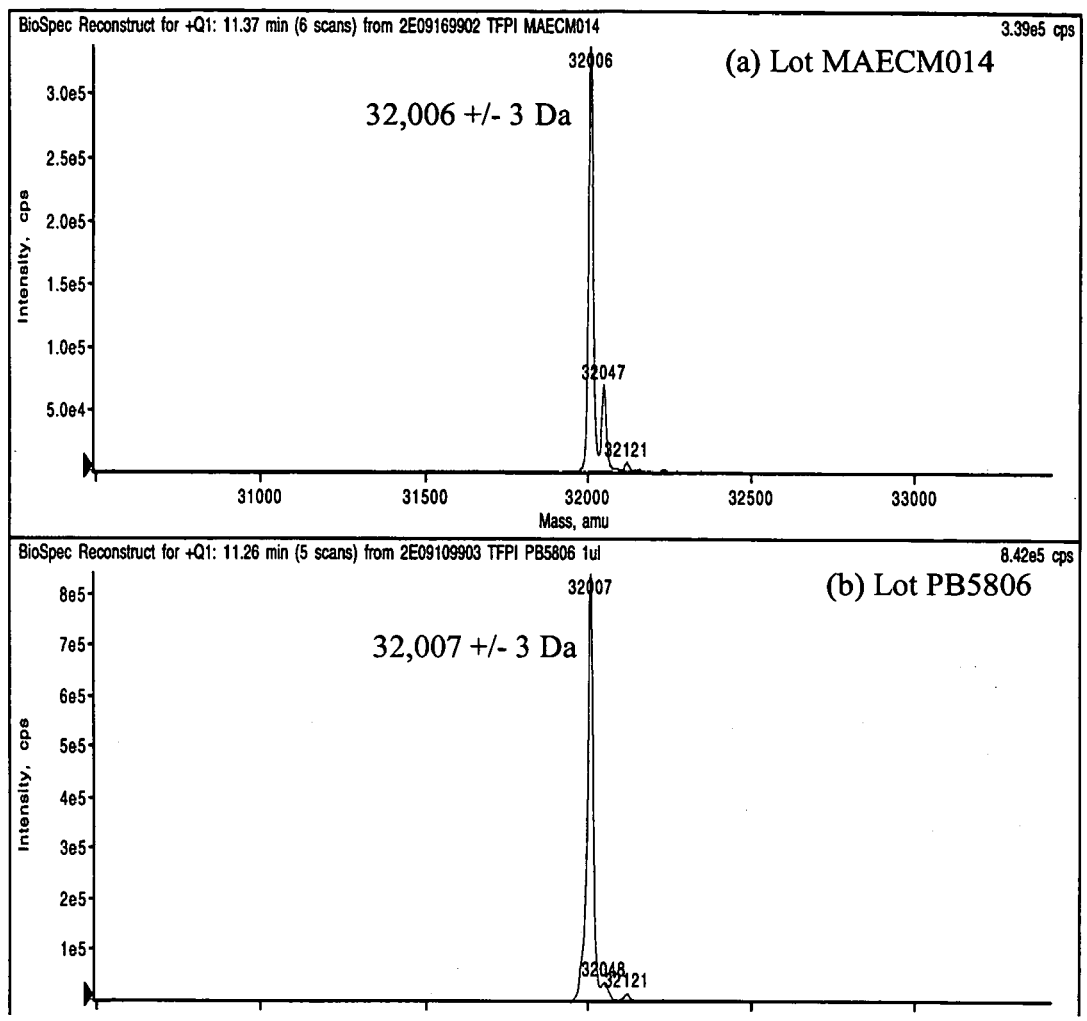
FIG. 6. Deconvoluted electrospray mass spectra showing intact protein molecular masses.

Analysis of intact rTFPI by LC-MS showed that the major component in each lot possesses the molecular mass predicted by the sequence of the gene (theoretical molecular mass 34,004 Da with nine disulfide bonds), indicating that the entire protein is expressed by the recombinant cell line. FIG. 6 shows the deconvoluted electrospray mass spectra of an rTFPI lot prepared according to Process B (MAECM014) and of an rTFPI lot prepared according to Process C (PB5806). Minor RTFPI components were also observed and further details of these structures are presented elsewhere. Table 6 lists the masses of the major rTFPI molecular ions observed during LC-MS analysis.

TABLE 6

Intact Average Molecular Masses of rTFPI measured by LC-MS

| Lot Number | Process | Observed Molecular Mass (Da)[1] | Theoretical Molecular Mass (Da) |
|---|---|---|---|
| MAECM014 | Process B | 32,006 | 32,004 |
| PB5806 | Process C | 32,007 | 32,004 |
| PB5666 | Process C | 32,005 | 32,004 |
| PB6096 | Process C | 32,007 | 32,004 |
| PB6376 | Process C | 32,006 | 32,004 |

[1]Mass accuracy approximately +/−3 Da

Primary Structure

Figure 7:
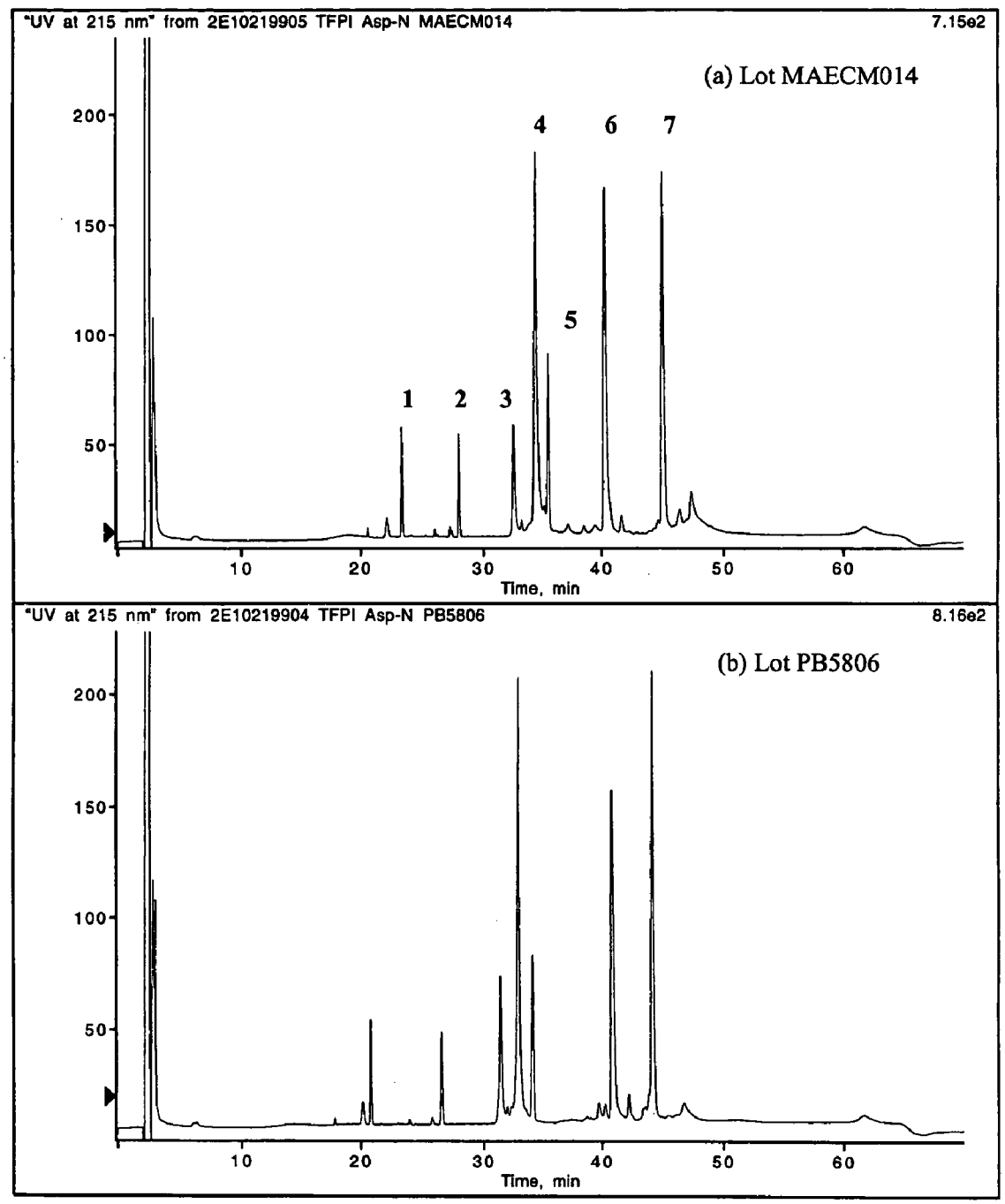
FIG. 7. UV chromatograms recorded during LC-MS analysis of non-reduced Asp-N peptides. Non-reduced samples from lots MAECM014 (FIG. 7A) and PB5806 (FIG. 7B) were subjected to Asp-N digestion and LC-MS analysis. The molecular masses of the identified peaks are shown in Table 8.
Figure 8:
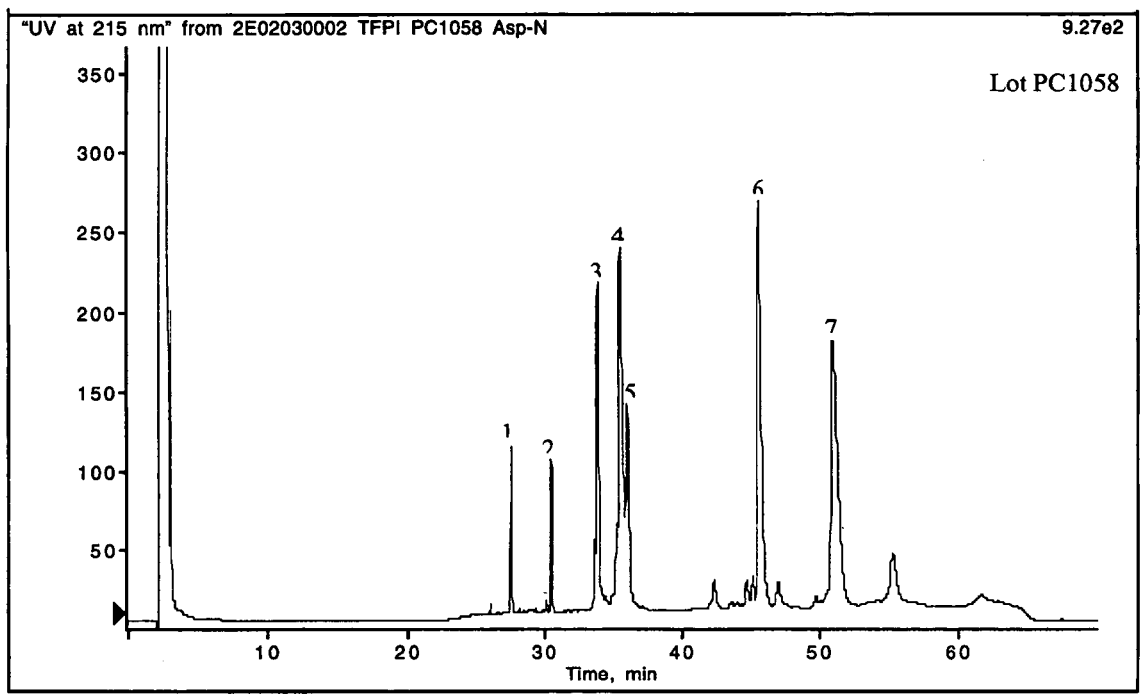
FIG. 8. UV chromatograms recorded during LC-MS analysis of non-reduced Asp-NpPeptides. A non-reduced sample from lot PC1058 was subjected to Asp-N digestion and LC-MS analysis.

The entire sequence of rTFPI was confirmed by a combination of analyses of an Asp-N endoproteinase peptide map of the non-reduced (native) protein and a tryptic peptide map of the RCM protein by LC-MS for lots MAECM014 and PB5806. Using LC-MS, both a conventional peptide map and the molecular masses of the peptides in the chromatogram are obtained in a single experiment. The Asp-N and tryptic peptide maps provided information about overlapping regions of the protein sequence for confirmation of the primary structure. FIG. 7 shows the UV chromatograms, recorded during LC-MS analysis, of Asp-N peptides for non-reduced rTFPI lots MAECM014 and PB5806. Table 7 lists the peptides identified in the Asp-N peptide maps by comparison of the measured m/z of the molecular ions with the theoretically predicted m/z values for Asp-N peptides. FIG. 8 shows the UV chromatograms, recorded during LC-MS analysis, of tryptic peptides for RCM rTFPI lots MAECM014 and PB5806. Table 8 lists the peptides identified in the tryptic peptide maps by comparison of the measured m/z of the molecular ions with the theoretically predicted m/z values for rTFPI tryptic peptides. The combination of the LC-MS results from the Asp-N and tryptic peptide maps accounts for 100% of the protein sequence (277 of 277 residues) and confirms the primary structure of the protein in both lots.

The peptide mapping results confirm not only the primary structure of rTFPI produced according to Process C, but also the removal of carbamylated rTFPI impurities. The +42 Da modification to rTFPI that occurs when the method of Process B is used was identified as being in the region of the protein associated with the third Kunitz domain (residues 206-258).

Analysis of Asp N and tryptic digests of rTFPI prepared according to Process C shows that the peptides corresponding to this domain have masses that are consistent with the theoretical mass of unmodified rTFPI, indicating that the rTFPI produced in the revised process has been purified of carbamylated species. In addition, there were no detectable levels of homocitrulline found during this analysis, consistent with the lack of carbamylated lysine residues in the rTFPI sample.

TABLE 7

Peptides identified by LC-MS from Asp-N digestion of non-denatured rTFPI Lots MAECM014 and PB5806

| HPLC Peak | Observed Mass MAECM014 | Observed Mass PB5806 | Theory Mass* | Residue Span | Amino Acid Sequence | |
|---|---|---|---|---|---|---|
| 1 | 956.4 | 956.6 | 956.5 | 6-13 | DEEHTIIT | (SEQ ID NO:2) |
| 2 | 1008.6 | 1008.6 | 1008.5 | 270-277 | EEIFVKNM | (SEQ ID NO:3) |
| 3 | 10031.8 | 10032.5 | 10031.7 | 183-269 Kunitz 3 | EFHGPSWCLTPADRGLC RANENRFYYNSVIGKCR PFKYSGCGGNENNFTSK QECLRACKKGFIQRISK GGLIKTKRKRKKQRVKI AY | (SEQ ID NO:4) |
| 4 | 10049.8 | 10050.5 | 10049.7 (+H$_2$O) | 183-269 Kunitz 3 clipped | EFHGPSWCLTPA/DRGL CRANENRFYYNSVIGKC RPFKYSGCGGNENNFTS KQECLRACKKGFIQRIS KGGLIKTKRKRKKQRVK IAY | (SEQ ID NO:5) |
| 5 | 2708.7 | 2709.1 | 2709.0 | 158-182 | DNYGTQLNAVNNSLTPQ STKVPSLF | (SEQ ID NO:6) |
| 6 | 9110.4 | 9111.0 | 9109.2 | 80-157 Kunitz 2 | DNANRIIKTTLQQEKPD FCFLEEDPGICRGYITR YFYNNQTKQCERFKYGG CLGNMNNFETLEECKNI CEDGPNGFQV | (SEQ ID NO:7) |
| 7 | 7764.1 | 7764.3 | 7764.0 (+H$_2$O) | 14-79 Kunitz 1 clipped | DTELPPLKLMHSFCAFK A/DDGPCKAIMKRFFFN IFTRQCEEFIYGGCEGN QNRFESLEECKKMCTR | (SEQ ID NO:8) |

*Monoisotopic masses below 1500 Da, average molecular masses above 1500 Da.
HPLC peaks 4 and peak 7 each contained two peptides held together by the disulfide bonds in the Kunitz region.

TABLE 8

Peptides identified by LC-MS from Trypsin Digestion of RCM rTFPI Lots MAECM014 and PB5806

| HPLC Peak | Observed Mass MAECM044 | Observed Mass PB5806 | Theory Mass* | Residue Span | Amino Acid Sequence | |
|---|---|---|---|---|---|---|
| 1 | 588.4 | 588.4 | 588.26 | 80-84 | R <DNANR> I | (SEQ ID NO:9) |
| 2 | 592.2 | 592.2 | 592.23 | 122-125 | K <QCER> F | (SEQ ID NO:10) |
| 3 | 567.4 | 567.2 | 567.21 | 76-79 | K <MCTR> D | (SEQ ID NO:11) |
| 4 | 461.2 | 461.2 | 461.27 | 38-41 | K <AIMK> R | (SEQ ID NO:12) |
| 5 | 705.6 | 705.4 | 705.31 | 234-238 | K <QECLR> A | (SEQ ID NO:13) |
| 6 | 608.4 | 608.2 | 608.33 | 109-113 | R <GYITR> Y | (SEQ ID NO:14) |
| 7 | 486.4 | 486.4 | 486.32 | 251-255 | K <GGLIK> T | (SEQ ID NO:15) |
| 8 | 707.6 | 707.4 | 707.34 | 215-219 | K <CRPFK> Y | (SEQ ID NO:16) |

TABLE 8-continued

Peptides identified by LC-MS from Trypsin Digestion of RCM rTFPI Lots MAECM014 and PB5806

| HPLC Peak | Observed Mass MAECM044 | Observed Mass PB5806 | Theory Mass* | Residue Span | Amino Acid Sequence | |
|---|---|---|---|---|---|---|
| 9 | 1535.3 | 1535.2 | 1535.56 | 220-233 | K <YSGCGGNENNFTSK> Q | (SEQ ID NO:17) |
| 10 | 619.4 | 619.4 | 619.34 | 243-247 | K <GFIQR> I | (SEQ ID NO:18) |
| 11 | 747.4 | 747.4 | 747.44 | 242-247 | K <KGFIQR> I | (SEQ ID NO:19) |
| 12 | 1076.7 | 1076.6 | 1076.49 | 114-121 | R <YFYNNQTK> Q | (SEQ ID NO:20) |
| 13 | 1169.6 | 1169.6 | 1169.53 | 67-75 | K <FESLEECKK> M | (SEQ ID NO:21) |
| 14 | 1041.8 | 1041.6 | 1041.43 | 67-74 | R <FESLEECK> K | (SEQ ID NO:22) |
| 15 | 1962.1 | 1962.4 | 1963.05 | 51-66 | R <QCEEFIYGGCEGNQNR> F | (SEQ ID NO:23) |
| 16 | 1089.6 | 1089.6 | 1089.55 | 206-214 | R <FYYNSVIGK> C | (SEQ ID NO:24) |
| 17 | 1140.6 | 1140.5 | 1140.51 | 22-30 | K <LMHSFCAFK> A | (SEQ ID NO:25) |
| 18 | 1110.6 | 1110.5 | 1110.60 | 267-275 | K <IAYEEIFVK> N | (SEQ ID NO:26) |
| 19 | 3498.0 | 3497.8 | 3497.72 | 146-177 | K <NICEDGPNGFQVDNYGTQLNAVNNSLTPQSTK> V | (SEQ ID NO:27) |
| 20 | 2138.8 | 2138.0 | 2138.34 | 128-145 | K <YGGCLGNMNNFETLEECK> N | (SEQ ID NO:28) |
| 21 | 2381.8 | 2382.3 | 2382.52 | 1-21 | <ADSEEDEEHTIITDTELPPLK> L | (SEQ ID NO:29) |
| 22 | 2585.8 | 2585.0 | 2585.86 | 88-108 | K <TTLQQEKPDFCFLEEDPGICR> G | (SEQ ID NO:30) |
| 23 | 5618.1 | 5618.9 | 5618.04 | 128-177 | K <YGGCLGNMNNFETLEECKNICEDGPNGFQVDNYGTQLNAVNNSLTPQSTK> V | (SEQ ID NO:31) |
| 24 | 2216.9 | 2216.8 | 2217.5 | 178-196 | K <VPSLFEFHGPSWCLTPADR> G | (SEQ ID NO:32) |
| 25 | 1090.7 | 1090.6 | 1090.56 | 43-50 | R <FFFNIFTR> Q | (SEQ ID NO:33) |

*Monoisotopic masses below 1500 Da; average molecular masses above 1500 Da.

Secondary/Tertiary Structure

Figure 9:
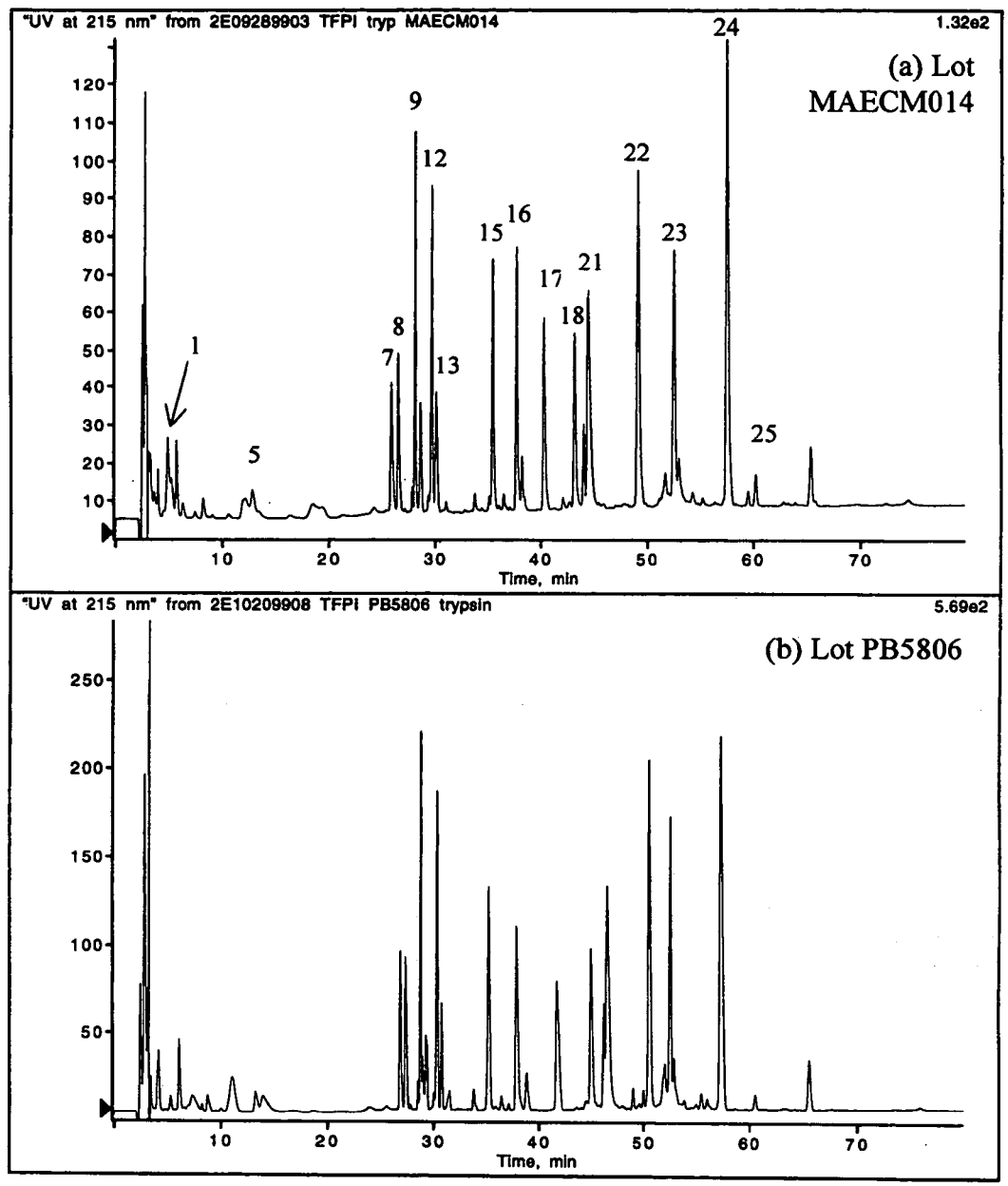
FIG. 9. UV chromatograms recorded during LC-MS analysis of RCM tryptic peptides.

The secondary/tertiary structure of rTFPI was confirmed by the analyses of Asp-N endoproteinase peptide map of lots MAECM014 and PB5806, where intact Kunitz domains were observed (FIG. 11 and Table 8). FIG. 9 illustrates the rTFPI structure, indicating the three Kunitz domains and the Asp-N cleavage sites. Under non-denaturing conditions, seven peptides are observed resulting from Asp-N cleavage between the Kunitz domains. Two of these peptides are also cleaved internally, but the resulting peptides are held together by disulfide bonds (FIG. 9). The data are consistent with the presence of disulfide bonds within the Kunitz domains and the absence of disulfide bonds between the Kunitz domains, as predicted for the secondary/tertiary structure of the native protein.

Example 3

Identification and Characterization of Minor Components

Purity Assessment by CN HPLC

Figure 10:
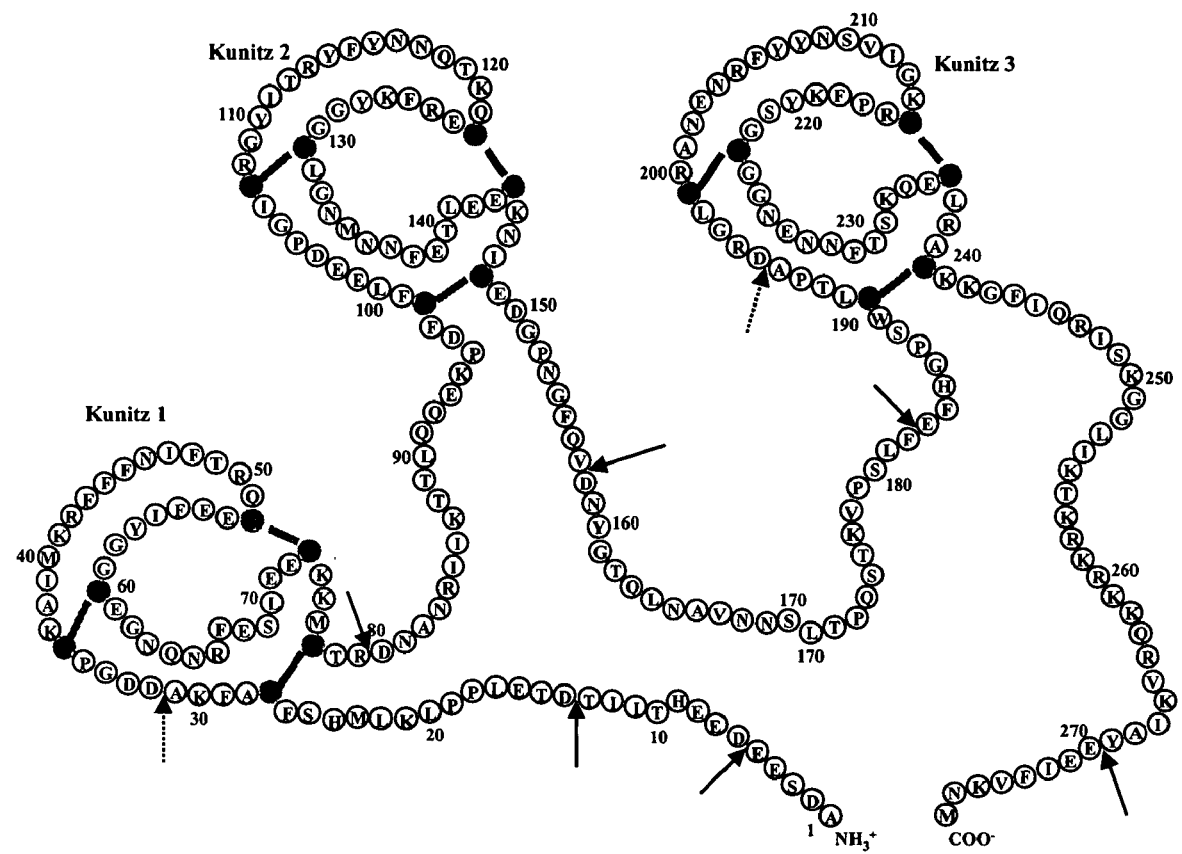
FIG. 10. Amino acid sequence of rTFPI depicting the three Kunitz regions and predicted disulfide bonds. Arrows indicate the cleavage sites resulting from digestion of rTFPI prepared according to Process C with Asp-N under non-denaturing conditions. Cleavage was observed at Asp-N sites indicated by solid arrows between the Kunitz regions, resulting in seven major peptides. Cleavage in the Kunitz regions, indicated by dashed arrows, resulted in peptides that were held together by the disulfide bonds. The addition of a water molecule at the cleavage sites in the internally cleaved peptides resulted in molecular masses that were 18 Da higher than the predicted non-cleaved peptides. The specific sites of internal cleavage, shown by dashed arrows, are based on previous work. The Asp-N peptides observed are consistent with the predicted secondary/tertiary structure of rTFPI.

A comparison of the CN HPLC chromatograms of rTFPI prepared according to Process B (A) and prepared according to Process C (B) is shown in FIG. 10. Process C produces material with an increase in purity by CN HPLC. All of the peaks that are separated by this assay contain rTFPI. Analysis of the peaks using ES-MS has determined that the Process B material contained approximately 75% rTFPI that has the theoretical mass, 5-10% rTFPI that has a mass which is increased by 16 amu and is believed to contain an oxidized methionine residue (peak 1), and approximately 15% rTFPI that has a mass which is increased by 42 or 43 amu and is believed to contain an acetylated lysine residue (peak 3). Material prepared according to Process C contains approximately 90% rTFPI main peak and 5-10% rTFPI containing an oxidized methionine residue (peak 1). Unlike the prior process, the process of the invention does not appear to produce appreciable levels of acetylated rTFPI. The reference standard for the process of the invention (peak 2, FIG. 10) shows a small shoulder, which elutes immediately before the rTFPI main peak and was identified as rTFPI containing substitutions of norvaline for leucine as described in the following sections.

Identification of Norvaline Misincorporation

A norvaline for leucine substitution has been identified in heterologous proteins expressed in E. coli and is believed to occur through misincorporation at the tRNA level (Apostol et al., J. Biol. Chem. 272, 28980-88, 1997). rTFPI contains 15 leucine residues and incorporation of norvaline instead of leucine was identified at four residue positions 90, 100, 181 and 191. The level of misincorporation at specific sites rTFPI lots prepared according to Process B (MAECM014) and according to Process C (PB5806) was estimated by comparison of the UV peak areas, recorded during LC-MS, of normal RCM rTFPI tryptic peptides with the corresponding norvaline-containing tryptic peptides. The total amount of norvaline was quantified by amino acid analysis.

Identification of Norvaline in the Collected CN HPLC Shoulder

The average molecular mass of rTFPI in the shoulder of the CN HPLC assay was identified as 31,989 Da by LC-MS. This value is 15 Da+/−3 Da lower than the molecular mass predicted for rTFPI (32,004 Da). To identify the nature of the modification, the protein in peak 2 (FIG. 10) was reduced and carboxymethylated, and then digested with trypsin. The tryptic peptides were analyzed by LC-MS and collected for accurate mass measurement by MALDI-TOF MS. Four of the six fractions collected showed monoisotopic molecular masses that were 14 Da lower than predicted peptides (Table 9). The peptides were sequenced by nanoES MS/MS and by Edman degradation. The modification was identified as norvaline incorporation at predicted leucine residue positions 90, 100, 181 and 191 and confirmed by the retention time of the PTH-amino acid during the Edman sequence analysis.

the UV detector and detection in the mass spectrometer during LC-MS, due to the time taken for the eluent to travel between the two detectors. The minor peaks eluting at approximately 48 minutes and 49 minutes were identified as peptide T(88-108) with norvaline misincorporation at residue position 100 (peptide nV100) and residue position 90 (peptide nV90), respectively (average molecular mass 2571.2 Da; theoretical mass 2571.2 Da). The norvaline incorporation sites were based on comparison with the peptides from the RP HPLC shoulder in rTFPI lot PB6096 identified above by Edman degradation and nanoES MS/MS analysis.

Figure 12:
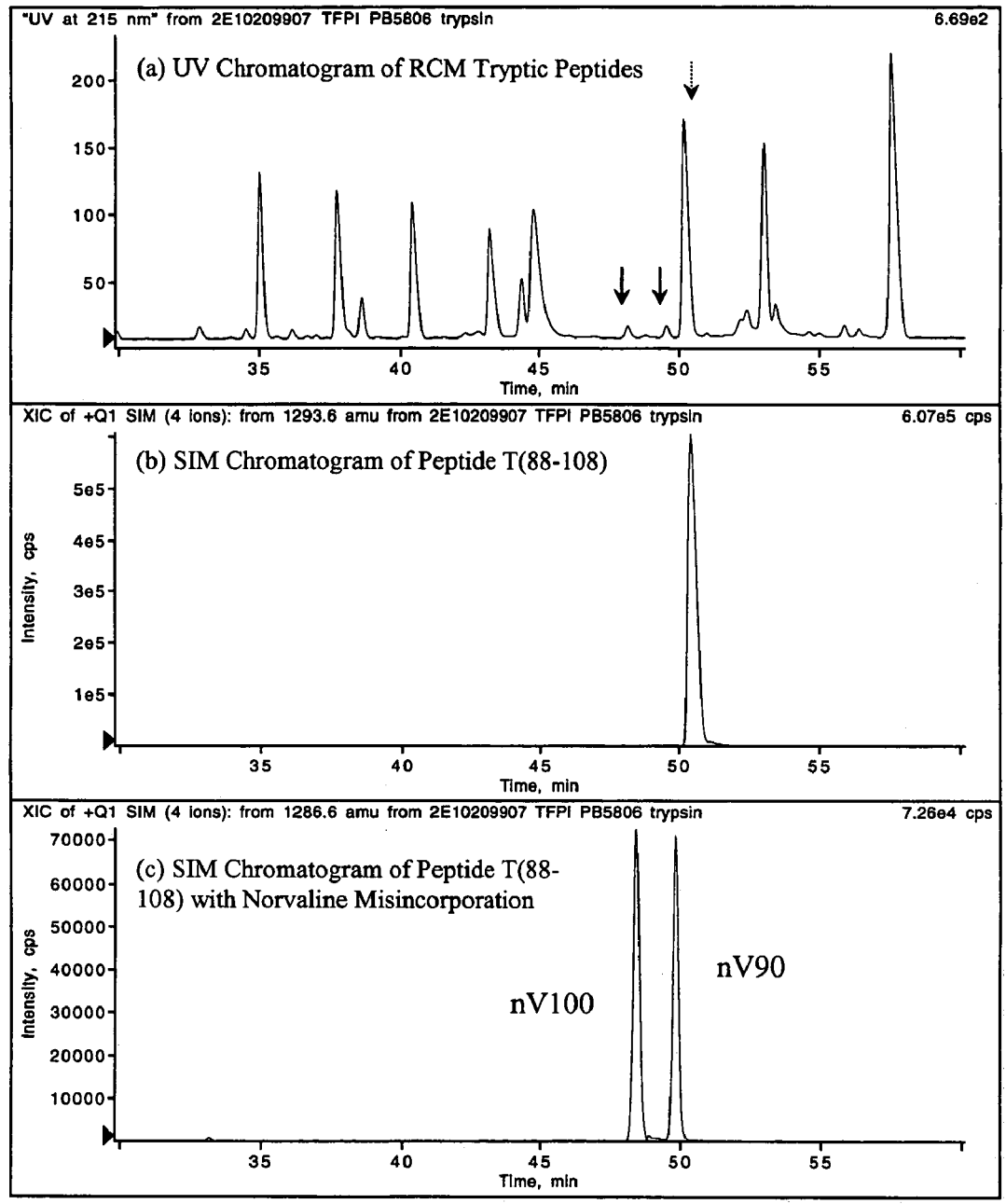
FIG. 12. Partial UV chromatogram of RCM tryptic peptides from lot PB5806.

FIG. 12C shows the SIM chromatogram for peptides nV100 and nV90 where the two peptides are clearly observed. The ratio of peptides T(88-108), nV100 and nV90 were calculated from the peak areas in the UV chromatogram (FIG. 12A) and the values obtained from four separate analyses. A similar approach was used to quantitate the degree of norvaline substitution in the tryptic peptides containing residues 178-196.

Table 10 shows the quantitation of norvaline misincorporation at residue positions 90, 100, 181 and 191 in four replicate LC-MS analyses. Peak areas at 215 nm were integrated

TABLE 9

Norvaline-containing RCM Tryptic Peptides identified by Accurate Mass MALDI-TOF MS, NanoES MS/MS and Edman Sequence Analysis

| Fraction | Observed Mass | Theory Mass | Residue Span | Amino Acid Sequence | |
|---|---|---|---|---|---|
| 1 | 2571.1 | 2585.2 | 88-108; nV100 | TTLQQEKPDFCFnVEEDPGICR | (SEQ ID NO:34) |
| 2 | 2571.0 | 2585.2 | 88-108; nV90 | TTnVQQEKPDFCFLEEDPGICR | (SEQ ID NO:35) |
| 3 | 2585.1 | 2585.2 | 88-108 | TTLQQEKPDFCFLEEDPGICR | (SEQ ID NO:36) |
| 4 | 2203.0 | 2117.0 | 178-196; nV181 | VPSnVFEFHGPSWCLTPADR | (SEQ ID NO:37) |
| 5 | 2202.8 | 2117.0 | 178-196; nV191 | VPSLFEFHGPSWCnVTPADR | (SEQ ID NO:38) |
| 6 | 2216.8 | 2117.0 | 178-196 | VPSLFEFHGPSWCLTPADR | (SEQ ID NO:39) |

Tryptic peptides from the CN HPLC peak 2 of lot PB6096 were isolated by LC-MS.
Norvaline is abbreviated as nV, and shown in bold fonts in the peptide sequences.
nV100, nV90, nV181 and nV191 indicate misincorporation at positions 190, 90, 181 and 191, respectively.

Quantitation of Norvaline Misincorporation at Specific Sites by LC-MS

Because the RP HPLC shoulder might only contain a fraction of rTFPI with norvaline misincorporation, unfractionated reference material prepared according to Process C was analyzed for quantitation of the norvaline-containing peptides. Lot PB5806 was reduced, alkylated, and then digested with trypsin. Four replicate LC-MS analyses were performed for quantitation of norvaline-containing peptides. Data were acquired using the full scan mode for molecular mass identification and selected ion monitoring (SIM) for increased sensitivity detection of norvaline-containing peptides.

FIG. 12A shows the UV chromatogram recorded between 30 and 60 minutes during LC-MS. The peak eluting at approximately 51 minutes was identified as tryptic peptide T(88-108) with average molecular mass 2585.2 Da. The SIM chromatogram for peptide T(88-108) is shown in FIG. 12B. Note, there is a slight delay between detection of peptides by for the peptides shown in SEQ ID NOS:34-39. Peak areas were summed for peptides 1, 2 and 3 and ratio of each peak over the sum was calculated and is shown in the table. The same was done for peptide 4, peptide 5 and peptide 6. Norvaline is abbreviated as nV, and shown in bold font in the peptide sequences. Relative amounts of misincorporation were calculated by comparison of UV peak areas of norvaline-containing peptides with the corresponding non-substituted peptide.

These composite results show that a norvaline substitution occurred in the reference lot PB5806 (prepared according to Process C) at residue positions 90, 100, 181 and 191. The level of incorporation at these sites is 3.3%, 4.3%, 2.8% and 1.4% respectively, corresponding to a molar level of misincorporation in PB5806 of at least 11.8%. In contrast, norvaline misincorporation in the reference lot prepared according to Process B (MAECM014) was only detected at minimal level, possibly at residue 100, and was estimated at <0.2%.

TABLE 10

| HPLC Run | Peptide | Peptide | Peptide | Peptide | Peptide | Peptide |
|---|---|---|---|---|---|---|
| 1 | 4.4% | 3.1% | 92.5% | 3.0% | 1.5% | 95.5% |
| 2 | 4.2% | 3.8% | 92.0% | 2.8% | 1.4% | 95.8% |
| 3 | 4.1% | 2.9% | 93.0% | 2.8% | 1.3% | 95.8% |
| 4 | 4.4% | 3.4% | 92.1% | 2.8% | 1.3% | 95.9% |
| Average of 4 | 4.3% | 3.3% | 92.4% | 2.8% | 1.4% | 95.8% |

*Peptide identity shown below:
```
Peptide 1:   88-108    TTLQQEKPDFCFnVEEDPGICR    (SEQ ID NO:34)
Peptide 2:   88-108    TTnVQQEKPDFCFLEEDPGICR    (SEQ ID NO:35)
Peptide 3:   88-108    TTLQQEKPDFCFLEEDPGICR     (SEQ ID NO:36)
Peptide 4:  178-196    VPSnVFEFHGPSWCLTPADR      (SEQ ID NO:37)
Peptide 5:  178-196    VPSLFEFHGPSWCnVTPADR      (SEQ ID NO:38)
Peptide 6:  178-196    VPSLFEFHGPSWCLTPADR       (SEQ ID NO:39)
```

Quantitation of Total Norvaline Misincorporation by Amino Acid Analysis

Table 11 summarizes the results of norvaline quantitation in the rTFPI preparations by ion-exchange amino acid analysis. The results are expressed as the percentage of leucine misincorporated as norvaline on a molar basis. With this method of analysis, there is no detectable amount of norvaline in rTFPI lot MAECM014 (Process B reference). However, the Process C reference (PB5806) and the other lots prepared by the new process contain an average of 2.64% norvaline per mole of leucine. If the misincorporation of norvaline for leucine occurs randomly, and there is an average of one norvaline per rTFPI molecule, this indicates that up to 40% of the rTFPI molecules would have a norvaline substitution. These results confirm the predictions of relative content generated from the LC-MS data.

TABLE 11

| Lot | Norvaline Content (%) |
|---|---|
| MAECM014 | Not detected |
| PB5806 | 2.52 |
| PB6376 | 2.45 |
| PB5666 | 3.03 |
| PB6096 | 2.54 |

Impact of Norvaline Substitution on in vitro Activity

Table 12 summarizes the in vitro PT bioactivity for materials prepared according to Process B and those prepared according to Process C. The presence of norvaline does not adversely effect rTFPI in vitro biological activity. PT activity remains constant even though the CN HPLC purity has increased substantially, indicating that this heterogeneity has minimal impact on activity.

TABLE 12

| Drug Product Lots | Drug Substance Process | Norvaline Substitution (%) | CN HPLC Purity (% Main Peak) | PT Activity (%) |
|---|---|---|---|---|
| MAJPN002 | Process B | ND | 76 | 102 |
| NA1246 | Process B | ND | 78 | 74 |
| NA4721 | Process B | ND | 78 | 117 |
| NA0182 | Process B | ND | 77 | 104 |
| PA1408 | Process B | ND | 80 | 108 |
| PB6095 | Process C | 2.5% | 92 | 98 |

ND, not determined.
PT activity is expressed as % control; release specification is 50-150%.

Example 4

Minor Components in Purity Assessment by Cation Exchange HPLC

Figure 13:
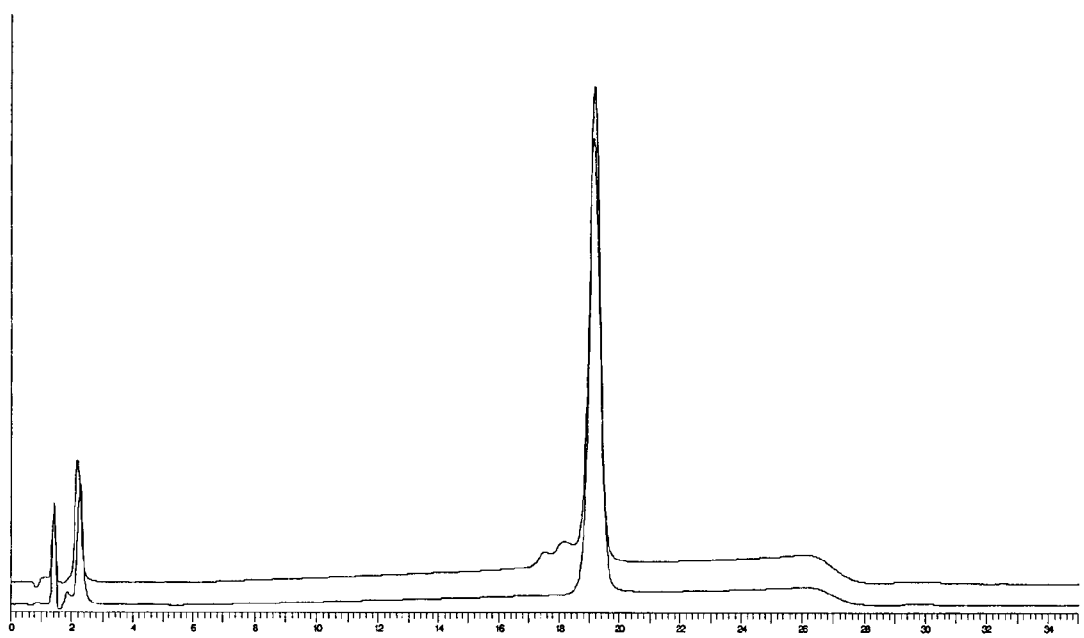
FIG. 13. In-process assay of SP-Sepharose HP samples using CEX-HPLC. Top sample represents the column load and the bottom sample represents the column pool after performing chromatography using SP-Sepharose FF.

FIG. 13 shows a comparison of rTFPI before and after performing SP-Sepharose HP chromatography. Purity of the main peak increases from 89% (load) to 100% (pool) after the SP-Sepharose HP chromatography step.

Example 5

Analysis of Intact Unfractionated rTFPI Drug Substance

Analysis of intact rTFPI by LC-MS was performed to demonstrate identity of the material produced according to Process C. The observed mass of the major component is 32,007 Da, which is consistent with the theoretical mass of 32,004 Da for rTFPI. These results indicate that the complete protein is expressed by the recombinant cell line.

Slow Gradient LC-MS

Unfractionated rTFPI lots MAECM014 (prepared according to Process B) and PB5806, PB6096, and PB6770 (prepared according to Process C) were analyzed by slow gradient LC-MS to confirm the assignment of early and late eluting peaks.

Figure 14:
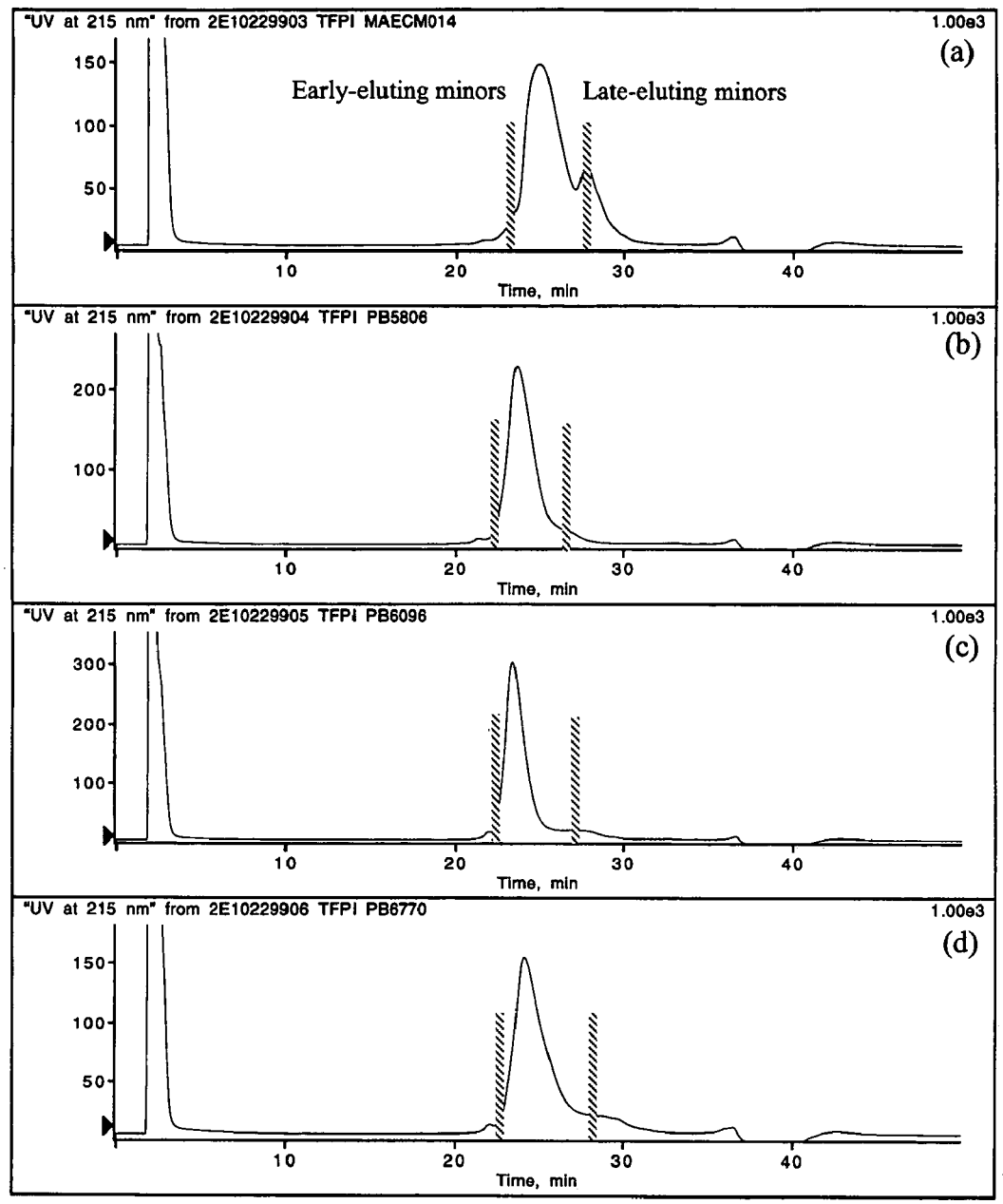
FIG. 14. UV chromatograms recorded during slow gradient reversed phase LC-MS analysis.

FIG. 14 shows the UV chromatograms, recorded during LC-MS, where the early eluting peak is observed in all the rTFPI lots, but the late eluting peak is only observed in the MAECM014 reference lot. The chromatograms are similar to those observed by the purity assessment assay, except the peaks are less resolved by LC-MS because of the use of a microbore column method in this analysis. The deconvoluted mass spectra of the early eluting peak in all the samples determined that the major molecular ion observed in all the spectra is consistent with rTFPI containing methionine sulfoxide.

The materials prepared according to Process C also contain a molecular ion with a molecular mass 28 Da lower than normal TFPI. This is consistent with TFPI molecules containing two sites of norvaline incorporation per molecule at predicted leucine residues. The deconvoluted mass spectrum for the late-eluting peak in lot MAECM014 was determined to contain a component is a +42/43 Da species. The deconvoluted mass spectra from the same region in the UV chromatograms of the new lots show significantly lower amounts of the +42/43 Da component. This observation is consistent with the identification of acetylated rTFPI in the reference material prepared according to Process B but not in the material prepared according to Process C.

Fast Gradient LC-MS

The mass spectrum of the Process B reference shows a minor component with a molecular mass +42/43 Da higher than normal rTFPI (approximately 15% relative abundance). Two minor peptides isolated from rTFPI lot MAECM014 by sequential digestion with Asp-N and Arg-C were identified as acetylated peptides, based on accurate mass measurement by MALDI-TOF MS and sequence analysis by nanoES MS/MS (DTELPPLKLMHSFCAFKA, SEQ ID NO:40 and FES-LEECKKMCTR, SEQ ID NO:41). The isolated peptides do not identify the proportion of the +42/43 Da species in intact rTFPI lot MAECM014 that possess the +42 Da (acetylated) modification. However, taken together with the data from CEX-HPLC and slow gradient LC-MS above, it is likely that the +42/43 Da minor component detected in the Process B reference lot by CN HPLC is mainly acetylated rTFPI.

Example 6

Removal of *E. coli* Proteins

For comparison of the relative amounts of *E. coli* proteins in rTFPI preparations produced according to Process B and in rTFPI preparations produced according to Process C, samples from the latter method were analyzed using an antibody ELISA assay with antibodies generated *E. coli* proteins.

The results in Table 13 show that the purification process is efficient in removing the putative *E. coli* impurities below the level of detection in this assay.

TABLE 13

| Lot Number | Process | ECP (ng/mg) |
|---|---|---|
| MAECM014 | 2 | <2 |
| PB5666 | 3 | <2 |
| PB5806 | 3 | <2 |
| PB6096 | 3 | <2 |

Example 7

Norleucine Substitution

It is well documented that the methionine analog norleucine can substitute for methionine in bacterial proteins. This substitution can be especially prevalent in *E. coli* cells that are stressed to overproduce a recombinant protein. Recombinant ala-TFPI has five methionyl residues, including one at the carboxyl terminus. The method described herein improves the expression level without increasing the amount of amino acid substitution.

Three lots of rTFPI were prepared according to Process C and tested for norleucine substitution. The results are shown in Table 14, where norleucine is expressed as a percentage of total methionine.

TABLE 14

Detection of Norleucine in rTFPI Isolated from Inclusion Bodies Produced by Process B and Process C

| Lot Number | Process | Norleucine |
|---|---|---|
| XAEFL012 | Process B | 0.6% |
| BNA078 | Process C | 0.3% |
| BNA079 | Process C | 0.2% |
| BNA086 | Process C | 0.3% |

The level of norleucine in these materials was slightly lower than the level present in materials prepared according to Process B. The limit of quantitation is 1%; thus, both levels are below the level of accurate quantitation by this assay.

Example 8

Measurement of Deamidation

Calibration Standard Preparation. S-adenosyl-homocysteine (SAH) standards were prepared for HPLC analysis by diluting Promega SAH Stock Standard (15.1 µM) to concentrations of 0.625, 1.25, 2.50, and 3.75 µM using Milli-Q water. Samples were kept at 2-8° C. prior to analysis by HPLC.

rTFPI Sample Preparation. Prior to sample preparation rTFPI Bulk Drug Substance samples (10.0 mg/ml) were diluted to 0.15 mg/ml using rTFPI Formulation Buffer. Each rTFPI sample was then prepared for incubation by adding 87 µl of TFPI to a reaction mixture containing 30 µl of 5× Promega Reaction Buffer, 3 µl of S-adenosyl-L-methionine, and 30 µl of PIMT. After brief vortexing, samples were incubated for 30 minutes in a water bath maintained at 30° C. After incubation, 30 µl of Promega Stop Solution NR was added to each sample followed by brief vortexing. Samples were kept at 2-8° C. prior to analysis by HPLC.

RP-HPLC. Measurement of SAH was performed using a modified RP-HPLC procedure developed by Carlson and Riggin[2]. Sample analysis was performed using a Waters Alliance HPLC system fitted with a YMC ODS-AQ 5 µm, 120 A, 4.6×250 mm column (Waters P/N AQ12S052546WT). Eluent A consisted of 25 mM $KH_2PO_4$, 10 mM 1-octanesulfonic acid, and 10% methanol while Eluent B was 100% methanol.

of 5.8% (Table 15). The level of deamidation was very similar to TFPI Drug Product (5.2%) stored at equivalent conditions.

Clinical Return Samples. As Table 15 reveals, analysis of three clinical return lots stored at +5° C. for ~2 years showed deamidation levels that averaged 15.9%. These results were very similar to the AnOps retain samples stored at identical conditions (15.4% deamidation).

TABLE 15

Results for the measurement of isoaspartic acid in rTFPI Drug Product and rTFPI Bulk Drug Substance samples.

| AID | Sample Info | Lot | Orientation | Temp | Months | % Deamidation |
|---|---|---|---|---|---|---|
| 41731 | Clinical Return ID#202008 | PC0895A | Upright | +5° C. | 24.8 | 14.5 |
| 41728 | Clinical Return ID#227085 | QA4321C | Upright | +5° C. | 20.5 | 15.3 |
| 41734 | Clinical Return ID#228782 | QA4322B | Upright | +5° C. | 20.4 | 18.0 |
| 41737 | AnOps Retain | PC0895 | Upright | +5° C. | 24.8 | 16.2 |
| 41743 | AnOps Retain | QA4321 | Upright | +5° C. | 20.5 | 15.3 |
| 41740 | AnOps Retain | QA4322 | Upright | +5° C. | 20.4 | 14.6 |
| 41716 | TFPI Drug Product | QA0477 | Upright | −60° C. | 22.3 | 5.2 |
| 41704 | TFPI Drug Product | QA0477 | Inverted | +8° C. | 6.0 | 8.2 |
| 41707 | TFPI Drug Product | QA0477 | Inverted | +8° C. | 12.0 | 15.3 |
| 41710 | TFPI Drug Product | QA0477 | Inverted | +8° C. | 18.0 | 20.2 |
| 41713 | TFPI Drug Product | QA0477 | Inverted | +8° C. | 24.0 | 26.1 |
| 41719 | TFPI Drug Product | QA0477 | Inverted | +25° C. | 3.0 | 33.7 |
| 41722 | TFPI Drug Product | QA0477 | Inverted | +25° C. | 4.5 | 46.2 |
| 41725 | TFPI Drug Product | QA0477 | Inverted | +25° C. | 6.1 | 57.3 |
| 41750 | TFPI Bulk Drug Substance | PC0522 | Upright | −60° C. | 26.0 | 4.6 |
| 41759 | TFPI Bulk Drug Substance | PC0788 | Upright | −60° C. | 25.8 | 5.3 |
| 41756 | TFPI Bulk Drug Substance | PC1058 | Upright | −60° C. | 25.6 | 5.6 |
| 41753 | TFPI Bulk Drug Substance | PC1611 | Upright | −60° C. | 24.8 | 7.6 |

The system was equilibrated at 10% Eluent B with a flow rate of 1.0 ml/nm. The column was maintained at ambient temperature with detection monitored at 260 nm. After sample injection (40 µl for SAH standards and 100 µl for TFPI samples), separation was achieved using a gradient from 10-60% Eluent B over 15 minutes followed by a column wash at 90% Eluent B for 3 minutes. The column was then re-equilibrated with the initial conditions (10% Eluent B) for 9 minutes prior to the next injection.

Data Analysis. After generating a calibration curve for the SAH standard set, the level of SAH in pmol was determined for each TFPI sample. Deamidation levels for each TFPI sample were then determined using the following formula:

$$Deamidation\ (\%) = \frac{pmol\ of\ SAH}{pmol\ of\ TFPI\ injected} \times 100$$

rTFPI Drug Product Stability. As Table 15 indicates, relative deamidation levels increase as a function of storage time and temperature. The stability sample set for lot QA0477 showed the following end-point deamidation levels: 5.2% (−60° C., 22 months), 26% (+8° C., 24 months), and 57% (+25° C., 6 months).

rTFPI Bulk Drug Substance Stability. Analysis of the four Bulk drug lots stored at −60° C. for ~24 months revealed deamidation levels that varied from 4.6% to 7.6% with a mean Thus, the Promega ISOQUANT® procedure is a simple and relatively quick means of measuring relative deamidation levels in rTFPI samples. The results showed that relative deamidation in rTFPI increases as a function of storage time and temperature; rTFPI clinical return and AnOps retain samples showed similar deamidation levels; and rTFPI Bulk Drug Substance and Drug Product both showed similar levels of deamidation.

Example 9

Description of Prolongation of Prothrombin Time by TFPI—The prothrombin time assay is a plasma based clotting assay in which coagulation is initiated by the addition of TF and calcium (Innovin) to plasma. TFPI prolongs prothrombin time in a dose dependent manner. Test samples of TFPI or TFPI analogs can be compared to TFPI or TFPI analog standards in this assay.

Protocol: The full Prothrombin Time assay (PT) program was run on the MLA Electra 9000 coagulometer. Reaction was initiated by the instrument with the addition of µl Innovin to the plasma samples. Time to clot formation was recorded. Ten µl of arg/phosphate buffer, added to 100 µl of plasma, gave a similar clotting time as plasma with no additions, 10.9 and 11.0 seconds, respectively. The activities of test samples were compared to a rTFPI standard using a standard curve from 0-4.5 µg/ml of rTFPI. Average values from triplicate analysis are shown in Table 16.

TABLE 16

Percent Functional Activity Relative to Standard As Determined by Prolongation of Prothrombin Time

| AID | Description | Lot No | Temp, °C | Time, m | | | | Ave | StdDev |
|---|---|---|---|---|---|---|---|---|---|
| 41598 | DP Stability | QA0477 | 8 | 6 | 120 | 145 | 130 | 131.7 | 12.6 |
| 41618 | DP Stability | QA0477 | 8 | 12 | 99 | 108 | 110 | 105.7 | 5.9 |
| 41623 | DP Stability | QA0477 | 8 | 18 | 115 | 130 | 135 | 126.7 | 10.4 |
| 41633 | DP Stability | QA0477 | 8 | 24 | 113 | 121 | 125 | 119.7 | 6.1 |
| 41638 | DP Frozen | QA0477 | <−60 | 22 | 126 | 141 | 121 | 129.3 | 10.4 |
| 41593 | DP Accel. Stability | QA0477 | 25 | 3 | 109 | 119 | 112 | 113.3 | 5.1 |
| 41603 | DP Accel. Stability | QA0477 | 25 | 4.5 | 102 | 100 | 108 | 103.3 | 4.2 |
| 41608 | DP Accel. Stability | QA0477 | 25 | 6.1 | 108 | 114 | 111 | 111.0 | 3.0 |
| 41646 | DP Clinic Return | QA4321C | 5 | 20.5 | 112 | 130 | 123 | 121.7 | 9.1 |
| 41651 | DP Clinic Return | PC0895A | 5 | 24.8 | 119 | 132 | 132 | 127.7 | 7.5 |
| 41656 | DP Clinic Return | QA4322B | 5 | 20.4 | 128 | 141 | 129 | 132.7 | 7.2 |
| 41675 | DP AnOps Retain | PC0895 | 5 | 24.8 | 121 | 119 | 135 | 125.0 | 8.7 |
| 41681 | DP AnOps Retain | QA4322 | 5 | 20.4 | 121 | 134 | 133 | 129.3 | 7.2 |
| 41687 | DP AnOps Retain | QA4321 | 5 | 20.5 | 120 | 125 | 119 | 121.3 | 3.2 |
| 41660 | DS Frozen | PC0789 | <−60 | 25 | 105 | 110 | 111 | 108.7 | 3.2 |
| 41665 | DP aliquot from AMD | QA4322 | 5 | 20 | 110 | 117 | 125 | 117.3 | 7.5 |
| 41669 | DP aliquot from AMD | PC0891 | 5 | 25 | 133 | 112 | 116 | 120.3 | 11.2 |

Example 10

Survival Studies

A murine cecal ligation and puncture study was conducted to compare a freshly prepared, clinical grade lot of rTFPI (TFPI 92) with clinical grade material that was partially deamidated and oxidized (TFPI 78). This model induces a polymicrobial intraperitoneal and systemic infection by direct fecal contamination and cecal necrosis, closely mimicking human intra-abdominal sepsis. Opal et al., *Critical Care Medicine* 29, 13-18, 2001.

Both preparations of TFPI were prepared according to Process C. Either rTFPI 78, rTFPI 92 or diluent control was given in a blinded fashion over 48 hours (SQ q12 hours×four doses). Prior to and 48 hours after the surgical procedure, blood was drawn to determine the level of quantitative bacteremia, endotoxin and cytokines (tumor necrosis factor-alpha and interleukin-6). The animals were observed daily and deaths were recorded as they occurred. All animals underwent necropsy evaluation for histological evidence of organ injury and quantitative bacteriology at the end of the experimental period.

Figure 16:
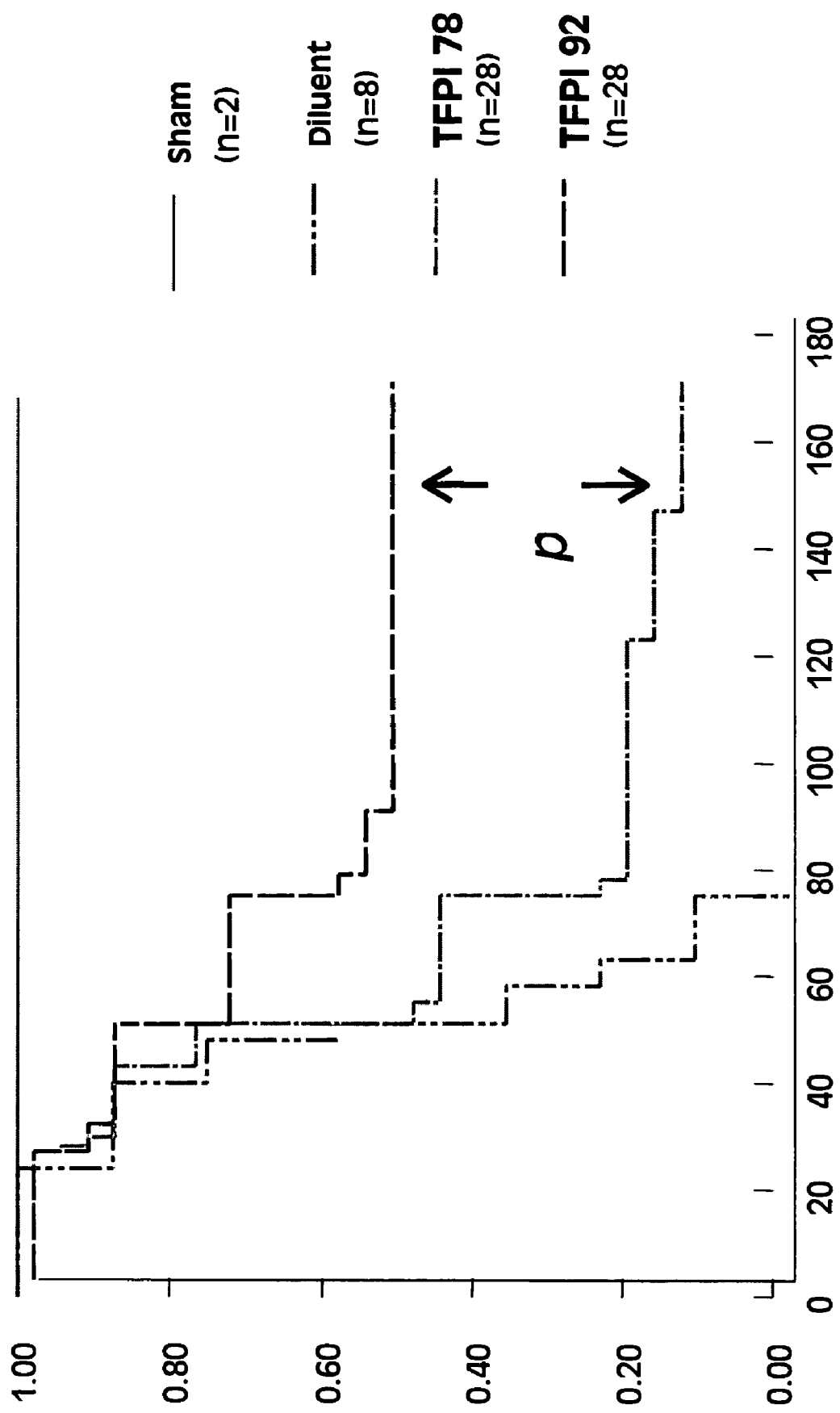
FIG. 16. Kaplan-Meier survival plots. X-axis, survival; Y-axis, time (hours).

The Kaplan-Meier survival plots are depicted in FIG. 16. There was a significant survival advantage for the mice who received the freshly prepared rTFPI as compared with the partially oxidized, deamidated form of rTFPI. Both rTFPI groups fared better than those mice that received diluent in the control group. As expected the sham-operated mice (surgical intervention with identification of the cecum but no ligation and puncture) survived the seven-day study period. There were no significant differences in the secondary endpoints of bacteremia, endotoxemia, or cytokine production between the two rTFPI-treated groups.

This study demonstrates that TFPI seems to offer a survival advantage through a mechanism not explained by blood levels of bacteria, endotoxin, or cytokines. Deamidated, oxidized TFPI offered less protection than freshly prepared TFPI.

---

The invention claimed is:

1. A purified preparation comprising tissue factor pathway inhibitor (TFPI) or TFPI analog molecules, wherein less than 2% of the TFPI or TFPI analog molecules are a carbamylated TFPI or TFPI analog molecule, as detected by cation exchange chromatography.

2. The purified preparation of claim 1, wherein less than about 1% of the TFPI or TFPI analog molecules are carbamylated.

3. The purified preparation of claim 1, wherein the TFPI molecules have the amino acid sequence shown in SEQ ID NO:1.

4. The purified preparation of claim 1, wherein the TFPI analog molecules are ala-TFPI molecules.

5. The purified preparation of claim 1 comprising 200 grams to 2.4 kilograms of tissue factor pathway inhibitor (TFPI) or TFPI analog.

6. The purified preparation of claim 5 comprising 200-300 grams of tissue factor pathway inhibitor (TFPI) or TFPI analog.

7. The purified preparation of claim 5 comprising 400-600 grams of tissue factor pathway inhibitor (TFPI) or TFPI analog.

8. The purified preparation of claim 5 comprising 600-900 grams of tissue factor pathway inhibitor (TFPI) or TFPI analog.

9. The purified preparation of claim 5 comprising 800-1200 grams of tissue factor pathway inhibitor (TFPI) or TFPI analog.

10. A pharmaceutical formulation comprising factor pathway inhibitor (TFPI) or TFPI analog molecules, wherein less than 2% of the TFPI or TFPI analog molecules are a carbamylated TFPI or TFPI analog molecule, as detected by cation exchange chromatography.

11. The pharmaceutical formulation of claim 10, wherein less than about 1% of the TFPI or TFPI analog molecules are carbamylated.

12. The pharmaceutical formulation of claim 10, wherein the TFPI molecules have the amino acid sequence shown in SEQ ID NO:1.

13. The pharmaceutical formulation of claim 10, wherein the TFPI analog molecules are ala-TFPI molecules.

14. A pharmaceutical formulation comprising:
tissue factor pathway inhibitor molecules having an additional amino terminal alanine residue (ala-TFPI), wherein less than 2% of the TFPI or TFPI analog molecules are a carbamylated ala-TFPI molecule, as detected by cation exchange chromatography,
wherein the pharmaceutical formulation comprises 20 mM sodium citrate, 300 mM L-arginine, and 5 mM methionine, pH 5.5.

15. A method of producing the purified preparation of claim 1, comprising the steps of:
  (1) expressing TFPI or a TFPI analog in a rifampicin-resistant *E. coli* host cell, wherein the TFPI or the TFPI analog is encoded on a plasmid comprising the following elements:
    (a) a transcription promoter;
    (b) a ribosome binding site adjacent to the reclac transcription promoter;
    (c) a nucleotide coding sequence that encodes the TFPI or the TFPI analog adjacent to the ribosome binding site;
    (d) a transcription terminator adjacent to the nucleotide coding sequence;
    (e) a replicon;
    (f) an antibiotic resistance gene; and
    (g) a gene encoding an N-terminal methionine-removing enzyme;
  (2) isolating inclusion bodies containing the TFPI or the TFPI analog from the *E. coli* host cell;
  (3) isolating the TFPI or the TFPI analog from the inclusion bodies to obtain isolated TFPI or TFPI analog;
  (4) refolding the isolated TFPI or TFPI analog to form refolded TFPI or TFPI analog;
  (5) purifying the refolded TFPI or TFPI analog by SP-Sepharose fast flow chromatography in the presence of $Mg^{++}$ to form a first preparation of purified TFPI or TFPI analog;
  (6) concentrating the first preparation of purified TFPI or TFPI analog to form a first concentrated preparation of purified TFPI or TFPI analog;
  (7) purifying the first concentrated preparation of purified TFPI or TFPI analog by Q-Sepharose HP chromatography to form a second preparation of purified TFPI or TFPI analog;
  (8) purifying the second preparation of purified TFPI or TFPI analog by butyl HIC chromatography to form a third preparation of purified TFPI or TFPI analog;
  (9) purifying the third preparation of purified TFPI or TFPI analog by SP-Sepharose HP chromatography to form a fourth preparation of purified TFPI or TFPI analog;
  (10) concentrating the fourth preparation of purified TFPI or TFPI analog to form a second concentrated preparation of purified TFPI or TFPI analog molecules.

16. The method of claim 15 wherein the transcription promoter is a reclac promoter.

17. The method of claim 15 wherein the ribosome binding site is the ribosome binding site from gene 10 of bacteriophage T7.

18. The method of claim 15 wherein the nucleotide coding sequence encodes ala-TFPI.

19. The method of claim 18 wherein the nucleotide coding sequence is SEQ ID NO:44.

20. The method of claim 15 wherein the transcription terminator comprises the nucleotide sequence shown in SEQ ID NO:42.

21. The method of claim 15 wherein the replicon comprises a pBR322 origin of replication.

22. The method of claim 15 wherein the replicon comprises a rop copy number control gene from pBR322.

23. The method of claim 15 wherein the antibiotic resistance gene is streptomycin adenyltransferase.

24. The method of claim 15 wherein the N-terminal methionine-removing enzyme is *E. coli* methionine aminopeptidase.

25. The method of claim 15 wherein the *E. coli* host cell is MON210 (ATCC Accession No. PTA-5564).

26. A method of purifying tissue factor pathway inhibitor (TFPI) or TFPI analog molecules to provide the purified preparation of claim 1, comprising the steps of:
  (1) purifying recombinantly produced TFPI or TFPI analog molecules by SP-Sepharose fast flow chromatography to form a first preparation of purified TFPI or TFPI analog;
  (2) concentrating the first preparation of purified TFPI or TFPI analog to form a first concentrated preparation of purified TFPI or TFPI analog;
  (3) purifying the first concentrated preparation of purified TFPI or TFPI analog by Q-Sepharose HP chromatography to form a second preparation of purified TFPI or TFPI analog;
  (4) purifying the second preparation of purified TFPI or TFPI analog by butyl HIC chromatography to form a third preparation of purified TFPI or TFPI analog;
  (5) purifying the third preparation of purified TFPI or TFPI analog by SP-Sepharose HP chromatography to form a fourth preparation of purified TFPI or TFPI analog;
  (6) concentrating the fourth preparation of purified TFPI or TFPI analog to form a second concentrated preparation of purified TFPI or TFPI analog molecules.

27. The method of claim 26 wherein the SP-Sepharose fast flow chromatography is performed in the presence of $Mg^{++}$.

28. The method of claim 26 wherein the TFPI or TFPI analog molecules are produced in yeast cells.

29. The method of claim 26 wherein the TFPI or TFPI analog molecules are produced in mammalian cells.

30. The method of claim 29 wherein the mammalian cells are CHO cells.

31. The method of claim 29 wherein the mammalian cells are HepG2 cells.

32. The method of claim 29 wherein the mammalian cells are Chang liver cells.

33. The method of claim 29 wherein the mammalian cells are SK hepatoma cells.

34. A method of expressing tissue factor pathway inhibitor (TFPI) or TFPI analog to provide the purified preparation of claim 1, comprising:
(1) culturing a rifampicin-resistant *E. coli* host cell in a fermentation medium, wherein the *E. coli* host cell comprises a plasmid having the following elements:
  (a) a transcription promoter;
  (b) a ribosome binding site adjacent to the reclac transcription promoter;
  (c) a nucleotide coding sequence that encodes TFPI or TFPI analog adjacent to the ribosome binding site;
  (d) a transcription terminator adjacent to the nucleotide coding sequence;
  (e) a replicon;
  (f) an antibiotic resistance gene; and
  (g) a gene encoding an N-terminal methionine-removing enzyme;
wherein one liter of the fermentation medium comprises 41 g dextrose, 2.5 g $(NH_4)_2SO_4$, 4.0 g sodium polyphosphate, 7.0 g $K_2SO_4$, 1.63 g $MgSO_4.7H_2O$, 2.0 g methionine, 2.0 g glycerol, 0.5 mg $H_3BO_4$, 0.5 g cobalt chloride, 0.13 g $CuSO_4.6H_2O$, 54.0 g $FeCl_3.6H_2O$, 11.0 g $MnSO_4.H_2O$, 0.5 g $Na_2MoO_4.2H_2O$, 0.02 $NaSeO_3$, 22.0 g $ZnSO_4.7H_2O$, 0.01 ml concentrated $H_2SO_4$, and 0.55 ml UCON antifoam.

35. The method of claim 34 wherein the transcription promoter is a reclac promoter.

36. The method of claim 34 wherein the ribosome binding site is the ribosome binding site from gene 10 of bacteriophage T7.

37. The method of claim 34 wherein the nucleotide coding sequence encodes ala-TFPI.

38. The method of claim 37 wherein the nucleotide coding sequence is SEQ ID NO:44.

39. The method of claim 34 wherein the transcription terminator comprises the nucleotide sequence shown in SEQ ID NO:42.

40. The method of claim 34 wherein the replicon comprises a pBR322 origin of replication.

41. The method of claim 34 wherein the replicon comprises a rop copy number control gene from pBR322.

42. The method of claim 34 wherein the antibiotic resistance gene is streptomycin adenyltransferase.

43. The method of claim 34 wherein the N-terminal methionine-removing enzyme is *E. coli* methionine aminopeptidase.

44. The method of claim 34 wherein the *E. coli* host cell is MON210 (ATCC Accession No. PTA-5564).

45. A method of preparing a pharmaceutical composition comprising tissue factor pathway inhibitor (TFPI) or ala-TFPI molecules, wherein less than 2% of the TFPI or ala-TFPI molecules are carbamylated molecules, as detected by cation exchange chromatography, the method comprising:
  (a) purifying refolded TFPI or ala-TFPI, which has been isolated from inclusion bodies following expression in a host cell, with a sequence of chromatography operations to provide a purified, refolded TFPI or ala-TFPI preparation,
  (b) concentrating and diafiltering the purified, refolded TFPI or ala-TFPI preparation to provide a TFPI or ala-TFPI drug substance, and
  (c) formulating the TFPI or ala-TFPI drug substance into the pharmaceutical composition,
  wherein the sequence of chromatography operations comprises two cation exchange chromatography operations, an anion exchange chromatography operation, and a hydrophobic interaction chromatography operation.

46. The method of claim 45, wherein the sequence of chromatography operations comprises, in order, a first cation exchange chromatography operation, an anion exchange chromatography operation, a hydrophobic interaction chromatography operation, and a second cation exchange chromatography operation.

47. The method of claim 46, wherein the first cation exchange operation is performed using a sodium citrate elution buffer.

48. The method of claim 46, wherein the first cation exchange operation is performed in the presence of urea.

49. The method of claim 45, wherein the TFPI or ala-TFPI drug substance has a protein concentration of about 10 mg/ml.

50. The method of claim 45, wherein the pharmaceutical composition contains 0.15 mg/ml ala-TFPI, 20 mM sodium citrate, 300 mM L-arginine, and 5 mM methionine and has a pH of 5.5.

51. The method of claim 45, wherein, in step (b), the purified, refolded TFPI or ala-TFPI preparation is concentrated and diafiltered into a buffer to provide the TFPI or ala-TFPI drug substance.

52. The method of claim 51, wherein the buffer comprises 300 mM L-arginine and 20 mM sodium citrate and has a pH of 5.5.

53. The method of claim 51, wherein the TFPI or ala-TFPI drug substance is storage stable at <60° C. for at least 24 months.

54. The method of claim 45, wherein step (a) comprises:
  (a1) purifying the refolded TFPI or ala-TFPI by SP-Sepharose fast flow chromatography to form a first preparation of purified TFPI or ala-TFPI,
  (a2) concentrating the first preparation of purified TFPI or ala-TFPI to form a first concentrated preparation of purified TFPI or ala-TFPI,
  (a3) purifying the first concentrated preparation of purified TFPI or ala-TFPI by Q-Sepharose HP chromatography to form a second preparation of purified TFPI or ala-TFPI,
  (a4) purifying the second preparation of purified TFPI or ala-TFPI by butyl HIC chromatography to form a third preparation of purified TFPI or ala-TFPI, and
  (a5) purifying the third preparation of purified TFPI or ala-TFPI by SP-Sepharose HP chromatography to provide the purified, refolded TFPI or ala-TFPI preparation.

55. The method of claim 54 wherein the SP-Sepharose fast flow chromatography is performed in the presence of $Mg^{++}$.

56. The method of claim 45, wherein step (a) provides the purified, refolded TFPI or ala-TFPI preparation in an amount from 200 grams to 2.4 kilograms.

57. The method of claim 45, further comprising, prior to step (a),
  (1) expressing the TFPI or ala-TFPI in an *E. coli* host cell,
  (2) isolating inclusion bodies containing the TFPI or ala-TFPI from the *E. coli* host cell,
  (3) isolating the TFPI or ala-TFPI from the inclusion bodies to obtain isolated TFPI or ala-TFPI, and
  (4) refolding the isolated TFPI or ala-TFPI to provide the refolded TFPI or ala-TFPI.

58. The method of claim 57, wherein the *E. coli* host cell is rifampicin-resistant.

59. The method of claim 57, wherein the *E. coli* host cell comprises a plasmid comprising:
  (a) a reclac transcription promoter,
  (b) a nucleotide coding sequence that encodes the TFPI or ala-TFPI,
  (c) a transcription terminator adjacent to the nucleotide coding sequence, and
  (d) a plasmid copy number control rop gene.

60. The method of claim 59, wherein the plasmid further comprises an antibiotic resistance gene.

61. The method of claim 60, wherein the antibiotic resistance gene is an aminoglycoside nucleotidyltransferase gene that confers resistance to streptomycin and spectinomycin.

62. The method of claim 59, wherein the plasmid further comprises a gene encoding an N-terminal methionine-removing enzyme.

* * * * *

SEQUENCE LISTING

<160> NUMBER OF SEQ ID NOS: 44

<210> SEQ ID NO 1
<211> LENGTH: 276
<212> TYPE: PRT
<213> ORGANISM: Homo sapiens

<400> SEQUENCE: 1

Asp Ser Glu Glu Asp Glu Glu His Thr Ile Ile Thr Asp Thr Glu Leu
 1               5                  10                  15

Pro Pro Leu Lys Leu Met His Ser Phe Cys Ala Phe Lys Ala Asp Asp
                20                  25                  30

Gly Pro Cys Lys Ala Ile Met Lys Arg Phe Phe Asn Ile Phe Thr
            35                  40                  45

Arg Gln Cys Glu Glu Phe Ile Tyr Gly Gly Cys Glu Gly Asn Gln Asn
        50                  55                  60

-continued

```
Arg Phe Glu Ser Leu Glu Glu Cys Lys Lys Met Cys Thr Arg Asp Asn
 65                  70                  75                  80

Ala Asn Arg Ile Ile Lys Thr Thr Leu Gln Gln Glu Lys Pro Asp Phe
                 85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
    210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
            260                 265                 270

Val Lys Asn Met
        275

<210> SEQ ID NO 2
<211> LENGTH: 8
<212> TYPE: PRT
<213> ORGANISM: Homo sapiens

<400> SEQUENCE: 2

Asp Glu Glu His Thr Ile Ile Thr
 1               5

<210> SEQ ID NO 3
<211> LENGTH: 8
<212> TYPE: PRT
<213> ORGANISM: Homo sapiens

<400> SEQUENCE: 3

Glu Glu Ile Phe Val Lys Asn Met
 1               5

<210> SEQ ID NO 4
<211> LENGTH: 87
<212> TYPE: PRT
<213> ORGANISM: Homo sapiens

<400> SEQUENCE: 4

Glu Phe His Gly Pro Ser Trp Cys Leu Thr Pro Ala Asp Arg Gly Leu
 1               5                  10                  15

Cys Arg Ala Asn Glu Asn Arg Phe Tyr Tyr Asn Ser Val Ile Gly Lys
            20                  25                  30
```

```
Cys Arg Pro Phe Lys Tyr Ser Gly Cys Gly Gly Asn Glu Asn Asn Phe
            35                  40                  45

Thr Ser Lys Gln Glu Cys Leu Arg Ala Cys Lys Lys Gly Phe Ile Gln
 50                  55                  60

Arg Ile Ser Lys Gly Gly Leu Ile Lys Thr Lys Arg Lys Arg Lys Lys
 65                  70                  75                  80

Gln Arg Val Lys Ile Ala Tyr
                85

<210> SEQ ID NO 5
<211> LENGTH: 87
<212> TYPE: PRT
<213> ORGANISM: Homo sapiens

<400> SEQUENCE: 5

Glu Phe His Gly Pro Ser Trp Cys Leu Thr Pro Ala Asp Arg Gly Leu
 1               5                  10                  15

Cys Arg Ala Asn Glu Asn Arg Phe Tyr Tyr Asn Ser Val Ile Gly Lys
                20                  25                  30

Cys Arg Pro Phe Lys Tyr Ser Gly Cys Gly Gly Asn Glu Asn Asn Phe
            35                  40                  45

Thr Ser Lys Gln Glu Cys Leu Arg Ala Cys Lys Lys Gly Phe Ile Gln
 50                  55                  60

Arg Ile Ser Lys Gly Gly Leu Ile Lys Thr Lys Arg Lys Arg Lys Lys
 65                  70                  75                  80

Gln Arg Val Lys Ile Ala Tyr
                85

<210> SEQ ID NO 6
<211> LENGTH: 25
<212> TYPE: PRT
<213> ORGANISM: Homo sapiens

<400> SEQUENCE: 6

Asp Asn Tyr Gly Thr Gln Leu Asn Ala Val Asn Asn Ser Leu Thr Pro
 1               5                  10                  15

Gln Ser Thr Lys Val Pro Ser Leu Phe
                20                  25

<210> SEQ ID NO 7
<211> LENGTH: 78
<212> TYPE: PRT
<213> ORGANISM: Homo sapiens

<400> SEQUENCE: 7

Asp Asn Ala Asn Arg Ile Ile Lys Thr Thr Leu Gln Gln Glu Lys Pro
 1               5                  10                  15

Asp Phe Cys Phe Leu Glu Glu Asp Pro Gly Ile Cys Arg Gly Tyr Ile
                20                  25                  30

Thr Arg Tyr Phe Tyr Asn Asn Gln Thr Lys Gln Cys Glu Arg Phe Lys
            35                  40                  45

Tyr Gly Gly Cys Leu Gly Asn Met Asn Asn Phe Glu Thr Leu Glu Glu
 50                  55                  60

Cys Lys Asn Ile Cys Glu Asp Gly Pro Asn Gly Phe Gln Val
 65                  70                  75

<210> SEQ ID NO 8
<211> LENGTH: 66
<212> TYPE: PRT
```

<213> ORGANISM: Homo sapiens

<400> SEQUENCE: 8

Asp Thr Glu Leu Pro Pro Leu Lys Leu Met His Ser Phe Cys Ala Phe
1               5                   10                  15

Lys Ala Asp Asp Gly Pro Cys Lys Ala Ile Met Lys Arg Phe Phe Phe
                20                  25                  30

Asn Ile Phe Thr Arg Gln Cys Glu Glu Phe Ile Tyr Gly Gly Cys Glu
            35                  40                  45

Gly Asn Gln Asn Arg Phe Glu Ser Leu Glu Glu Cys Lys Lys Met Cys
50                  55                  60

Thr Arg
65

<210> SEQ ID NO 9
<211> LENGTH: 7
<212> TYPE: PRT
<213> ORGANISM: Homo sapiens

<400> SEQUENCE: 9

Arg Asp Asn Ala Asn Arg Ile
1               5

<210> SEQ ID NO 10
<211> LENGTH: 6
<212> TYPE: PRT
<213> ORGANISM: Homo sapiens

<400> SEQUENCE: 10

Lys Gln Cys Glu Arg Phe
1               5

<210> SEQ ID NO 11
<211> LENGTH: 6
<212> TYPE: PRT
<213> ORGANISM: Homo sapiens

<400> SEQUENCE: 11

Lys Met Cys Thr Arg Asp
1               5

<210> SEQ ID NO 12
<211> LENGTH: 6
<212> TYPE: PRT
<213> ORGANISM: Homo sapiens

<400> SEQUENCE: 12

Lys Ala Ile Met Lys Arg
1               5

<210> SEQ ID NO 13
<211> LENGTH: 7
<212> TYPE: PRT
<213> ORGANISM: Homo sapiens

<400> SEQUENCE: 13

Lys Gln Glu Cys Leu Arg Ala
1               5

<210> SEQ ID NO 14
<211> LENGTH: 7
<212> TYPE: PRT
<213> ORGANISM: Homo sapiens

```
<400> SEQUENCE: 14

Arg Gly Tyr Ile Thr Arg Tyr
1               5

<210> SEQ ID NO 15
<211> LENGTH: 7
<212> TYPE: PRT
<213> ORGANISM: Homo sapiens

<400> SEQUENCE: 15

Lys Gly Gly Leu Ile Lys Thr
1               5

<210> SEQ ID NO 16
<211> LENGTH: 7
<212> TYPE: PRT
<213> ORGANISM: Homo sapiens

<400> SEQUENCE: 16

Lys Cys Arg Pro Phe Lys Tyr
1               5

<210> SEQ ID NO 17
<211> LENGTH: 16
<212> TYPE: PRT
<213> ORGANISM: Homo sapiens

<400> SEQUENCE: 17

Lys Tyr Ser Gly Cys Gly Gly Asn Glu Asn Asn Phe Thr Ser Lys Gln
1               5                   10                  15

<210> SEQ ID NO 18
<211> LENGTH: 7
<212> TYPE: PRT
<213> ORGANISM: Homo sapiens

<400> SEQUENCE: 18

Lys Gly Phe Ile Gln Arg Ile
1               5

<210> SEQ ID NO 19
<211> LENGTH: 8
<212> TYPE: PRT
<213> ORGANISM: Homo sapiens

<400> SEQUENCE: 19

Lys Lys Gly Phe Ile Gln Arg Ile
1               5

<210> SEQ ID NO 20
<211> LENGTH: 10
<212> TYPE: PRT
<213> ORGANISM: Homo sapiens

<400> SEQUENCE: 20

Arg Tyr Phe Tyr Asn Asn Gln Thr Lys Gln
1               5                   10

<210> SEQ ID NO 21
<211> LENGTH: 11
<212> TYPE: PRT
<213> ORGANISM: Homo sapiens

<400> SEQUENCE: 21
```

-continued

Lys Phe Glu Ser Leu Glu Glu Cys Lys Lys Met
1               5                   10

<210> SEQ ID NO 22
<211> LENGTH: 10
<212> TYPE: PRT
<213> ORGANISM: Homo sapiens

<400> SEQUENCE: 22

Arg Phe Glu Ser Leu Glu Glu Cys Lys Lys
1               5                   10

<210> SEQ ID NO 23
<211> LENGTH: 18
<212> TYPE: PRT
<213> ORGANISM: Homo sapiens

<400> SEQUENCE: 23

Arg Gln Cys Glu Glu Phe Ile Tyr Gly Gly Cys Glu Gly Asn Gln Asn
1               5                   10                  15

Arg Phe

<210> SEQ ID NO 24
<211> LENGTH: 11
<212> TYPE: PRT
<213> ORGANISM: Homo sapiens

<400> SEQUENCE: 24

Arg Phe Tyr Tyr Asn Ser Val Ile Gly Lys Cys
1               5                   10

<210> SEQ ID NO 25
<211> LENGTH: 11
<212> TYPE: PRT
<213> ORGANISM: Homo sapiens

<400> SEQUENCE: 25

Lys Leu Met His Ser Phe Cys Ala Phe Lys Ala
1               5                   10

<210> SEQ ID NO 26
<211> LENGTH: 11
<212> TYPE: PRT
<213> ORGANISM: Homo sapiens

<400> SEQUENCE: 26

Lys Ile Ala Tyr Glu Glu Ile Phe Val Lys Asn
1               5                   10

<210> SEQ ID NO 27
<211> LENGTH: 34
<212> TYPE: PRT
<213> ORGANISM: Homo sapiens

<400> SEQUENCE: 27

Lys Asn Ile Cys Glu Asp Gly Pro Asn Gly Phe Gln Val Asp Asn Tyr
1               5                   10                  15

Gly Thr Gln Leu Asn Ala Val Asn Asn Ser Leu Thr Pro Gln Ser Thr
                20                  25                  30

Lys Val

<210> SEQ ID NO 28

```
<211> LENGTH: 20
<212> TYPE: PRT
<213> ORGANISM: Homo sapiens

<400> SEQUENCE: 28

Lys Tyr Gly Gly Cys Leu Gly Asn Met Asn Asn Phe Glu Thr Leu Glu
 1               5                  10                  15

Glu Cys Lys Asn
            20

<210> SEQ ID NO 29
<211> LENGTH: 22
<212> TYPE: PRT
<213> ORGANISM: Homo sapiens

<400> SEQUENCE: 29

Ala Asp Ser Glu Glu Asp Glu Glu His Thr Ile Ile Thr Asp Thr Glu
 1               5                  10                  15

Leu Pro Pro Leu Lys Leu
            20

<210> SEQ ID NO 30
<211> LENGTH: 23
<212> TYPE: PRT
<213> ORGANISM: Homo sapiens

<400> SEQUENCE: 30

Lys Thr Thr Leu Gln Gln Glu Lys Pro Asp Phe Cys Phe Leu Glu Glu
 1               5                  10                  15

Asp Pro Gly Ile Cys Arg Gly
            20

<210> SEQ ID NO 31
<211> LENGTH: 52
<212> TYPE: PRT
<213> ORGANISM: Homo sapiens

<400> SEQUENCE: 31

Lys Tyr Gly Gly Cys Leu Gly Asn Met Asn Asn Phe Glu Thr Leu Glu
 1               5                  10                  15

Glu Cys Lys Asn Ile Cys Glu Asp Gly Pro Asn Gly Phe Gln Val Asp
            20                  25                  30

Asn Tyr Gly Thr Gln Leu Asn Ala Val Asn Asn Ser Leu Thr Pro Gln
        35                  40                  45

Ser Thr Lys Val
    50

<210> SEQ ID NO 32
<211> LENGTH: 21
<212> TYPE: PRT
<213> ORGANISM: Homo sapiens

<400> SEQUENCE: 32

Lys Val Pro Ser Leu Phe Glu Phe His Gly Pro Ser Trp Cys Leu Thr
 1               5                  10                  15

Pro Ala Asp Arg Gly
            20

<210> SEQ ID NO 33
<211> LENGTH: 10
<212> TYPE: PRT
<213> ORGANISM: Homo sapiens
```

```
<400> SEQUENCE: 33

Arg Phe Phe Phe Asn Ile Phe Thr Arg Gln
1               5                   10

<210> SEQ ID NO 34
<211> LENGTH: 21
<212> TYPE: PRT
<213> ORGANISM: Homo sapiens
<220> FEATURE:
<221> NAME/KEY: VARIANT
<222> LOCATION: (1)...(21)
<223> OTHER INFORMATION: Xaa = norvaline

<400> SEQUENCE: 34

Thr Thr Leu Gln Gln Glu Lys Pro Asp Phe Cys Phe Xaa Glu Glu Asp
1               5                   10                  15

Pro Gly Ile Cys Arg
            20

<210> SEQ ID NO 35
<211> LENGTH: 21
<212> TYPE: PRT
<213> ORGANISM: Homo sapiens
<220> FEATURE:
<221> NAME/KEY: VARIANT
<222> LOCATION: (1)...(21)
<223> OTHER INFORMATION: Xaa = norvaline

<400> SEQUENCE: 35

Thr Thr Xaa Gln Gln Glu Lys Pro Asp Phe Cys Phe Leu Glu Glu Asp
1               5                   10                  15

Pro Gly Ile Cys Arg
            20

<210> SEQ ID NO 36
<211> LENGTH: 21
<212> TYPE: PRT
<213> ORGANISM: Homo sapiens

<400> SEQUENCE: 36

Thr Thr Leu Gln Gln Glu Lys Pro Asp Phe Cys Phe Leu Glu Glu Asp
1               5                   10                  15

Pro Gly Ile Cys Arg
            20

<210> SEQ ID NO 37
<211> LENGTH: 19
<212> TYPE: PRT
<213> ORGANISM: Homo sapiens
<220> FEATURE:
<221> NAME/KEY: VARIANT
<222> LOCATION: (1)...(19)
<223> OTHER INFORMATION: Xaa = norvaline

<400> SEQUENCE: 37

Val Pro Ser Xaa Phe Glu Phe His Gly Pro Ser Trp Cys Leu Thr Pro
1               5                   10                  15

Ala Asp Arg

<210> SEQ ID NO 38
<211> LENGTH: 19
<212> TYPE: PRT
<213> ORGANISM: Homo sapiens
<220> FEATURE:
```

```
<221> NAME/KEY: VARIANT
<222> LOCATION: (1)...(19)
<223> OTHER INFORMATION: Xaa = norvaline

<400> SEQUENCE: 38

Val Pro Ser Leu Phe Glu Phe His Gly Pro Ser Trp Cys Xaa Thr Pro
 1               5                  10                  15
Ala Asp Arg

<210> SEQ ID NO 39
<211> LENGTH: 19
<212> TYPE: PRT
<213> ORGANISM: Homo sapiens

<400> SEQUENCE: 39

Val Pro Ser Leu Phe Glu Phe His Gly Pro Ser Trp Cys Leu Thr Pro
 1               5                  10                  15
Ala Asp Arg

<210> SEQ ID NO 40
<211> LENGTH: 18
<212> TYPE: PRT
<213> ORGANISM: Homo sapiens

<400> SEQUENCE: 40

Asp Thr Glu Leu Pro Pro Leu Lys Leu Met His Ser Phe Cys Ala Phe
 1               5                  10                  15
Lys Ala

<210> SEQ ID NO 41
<211> LENGTH: 13
<212> TYPE: PRT
<213> ORGANISM: Homo sapiens

<400> SEQUENCE: 41

Phe Glu Ser Leu Glu Glu Cys Lys Lys Met Cys Thr Arg
 1               5                  10

<210> SEQ ID NO 42
<211> LENGTH: 30
<212> TYPE: DNA
<213> ORGANISM: Homo sapiens

<400> SEQUENCE: 42
agcgtcgaca ctcccgttct ggataatgtt                                        30

<210> SEQ ID NO 43
<211> LENGTH: 1118
<212> TYPE: DNA
<213> ORGANISM: Homo sapiens

<400> SEQUENCE: 43
ggatcccgcg gttctgaaat gagctgttga caattaatca tcggctcgta taatgtgtgg      60
aattgtgagc ggataacaat ttcacacaga tctgggccct tcgaaattaa tacgactcac     120
tataggagac cacaacggt ttccctctag aaataatttt gtttaacttt aagaaggaga      180
tatatccatg gctgattctg aagaagatga agaacatact attatcactg atactgaact     240
gccaccgctg aaactgatgc attcattttg tgcattcaag gcggacgacg gcccgtgcaa     300
agccatcatg aagcgcttct tcttcaacat cttcactcgt cagtgcgaag aatttatata     360
tgggggatgt gaaggaaatc agaatcgatt tgagtccctc gaagaatgca gaagatgtg     420
```

```
cacccgcgac aacgcaaaca ggattataaa gacaacattg caacaagaaa agccagattt    480 ctgcttttg gaagaagatc ctggaatatg tcgaggttat attaccaggt attttataa    540 caatcagaca aaacagtgtg aacgtttcaa gtatggtgga tgcctgggca atatgaacaa    600
ttttgagaca ctggaagaat gcaagaacat ttgtgaagat ggtccgaatg gtttccaggt    660
ggataattat ggaacccagc tcaatgctgt gaataactcc ctgactccgc aatcaaccaa    720
ggttcccagc cttttgaat tcacggtcc ctcatggtgt ctcactccag cagacagagg    780
attgtgtcgt gccaatgaga acagattcta ctacaattca gtcattggga atgccgccc    840 atttaagtac agtggatgtg ggggaaatga aaacaatttt acttccaaac aagaatgtct    900
gagggcatgt aaaaaaggtt tcatccaaag aatatcaaaa ggaggcctaa ttaaaaccaa    960
aagaaaaaga aagaagcaga gagtgaaaat agcatatgaa gaatttttg ttaaaaatat    1020 gtaataaaag cttatcgatg ataagctgtc aaacatgaga attcgatatc aacgcaacga    1080
cccagccgaa gctgggtcgt tgcgttgata tcgaattc                           1118

<210> SEQ ID NO 44
<211> LENGTH: 834
<212> TYPE: DNA
<213> ORGANISM: Homo sapiens

<400> SEQUENCE: 44
catggctgat tctgaagaag atgaagaaca tactattatc actgatactg aactgccacc     60
gctgaaactg atgcattcat tttgtgcatt caaggcggac gacggcccgt gcaaagccat    120
catgaagcgc ttcttcttca acatcttcac tcgtcagtgc gaagaattta tatatggggg    180
atgtgaagga aatcagaatc gatttgagtc cctcgaagaa tgcaagaaga tgtgcacccg    240
cgacaacgca aacaggatta taaagacaac attgcaacaa gaaaagccag atttctgctt    300
tttggaagaa gatcctggaa tatgtcgagg ttatattacc aggtattttt ataacaatca    360
gacaaaacag tgtgaacgtt tcaagtatgg tggatgcctg gcaatatga acaattttga    420 gacactggaa gaatgcaaga acatttgtga agatggtccg aatggtttcc aggtggataa    480
ttatggaacc cagctcaatg ctgtgaataa ctccctgact ccgcaatcaa ccaaggttcc    540
cagccttttt gaatttcacg gtccctcatg gtgtctcact ccagcagaca gaggattgtg    600
tcgtgccaat gagaacagat tctactacaa ttcagtcatt gggaatgcc gcccatttaa    660 gtacagtgga tgtgggggaa atgaaaacaa tttttacttcc aaacaagaat gtctgagggc    720
atgtaaaaaa ggtttcatcc aaagaatatc aaaggaggc ctaattaaaa ccaaaagaaa    780
aagaaagaag cagagagtga aaatagcata tgaagaaatt tttgttaaaa atat         834
```